(12) United States Patent
Berlin et al.

(10) Patent No.: US 10,123,535 B2
(45) Date of Patent: *Nov. 13, 2018

(54) COMPOSITIONS AND METHODS FOR IMPROVING POST-HARVEST PROPERTIES OF AGRICULTURAL CROPS

(71) Applicant: Novozymes A/S, Bagsvaerd (DK)

(72) Inventors: Alex Berlin, Davis, CA (US); Jason Quinlan, Davis, CA (US); Romil Benyamino, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/122,610

(22) PCT Filed: Mar. 5, 2015

(86) PCT No.: PCT/US2015/019011
§ 371 (c)(1),
(2) Date: Aug. 30, 2016

(87) PCT Pub. No.: WO2015/134776
PCT Pub. Date: Sep. 11, 2015

(65) Prior Publication Data
US 2017/0064951 A1    Mar. 9, 2017

Related U.S. Application Data

(60) Provisional application No. 61/948,232, filed on Mar. 5, 2014.

(51) Int. Cl.
*A01N 43/16* (2006.01)
*A01N 37/20* (2006.01)
*A23L 3/3544* (2006.01)

(52) U.S. Cl.
CPC ............ *A01N 43/16* (2013.01); *A01N 37/20* (2013.01); *A23L 3/3544* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,602,111 A * | 2/1997 | Misaki | A01N 43/16 514/54 |
| 5,968,813 A | 10/1999 | Kofod et al. | |
| 6,027,740 A | 2/2000 | Puterka et al. | |
| 6,069,112 A | 5/2000 | Glenn et al. | |
| 6,110,867 A | 8/2000 | Glenn et al. | |
| 6,156,327 A | 12/2000 | Sekutowski et al. | |
| 2009/0104222 A1 | 4/2009 | Freund | |
| 2010/0304975 A1 * | 12/2010 | Salvador | A01N 43/16 504/292 |

FOREIGN PATENT DOCUMENTS

WO    2005116215 A1    12/2005

OTHER PUBLICATIONS

Sonoma Grape Sales—2009.*
Blooming Branch Apricot.*
Nutmeg—Wikipedia.*
Farming for Quality—2012.*
Vegetable seeds per ounce.*
Zhou et al., "The influence of surface chemical composition on the adsorption of xyloglucan to chemical and mechanical pulps", Carbohydrate Polymers 63: 449-458 (2006).*
Kallas et al., "Enzymatic properties of native and deglycosylated hybrid aspen (*Populus tremula tremuloides*) xyloglucan endotransglycosylate 16A expressed in Pichia pastoris", Biochem J 390: 105-113 (2005).*
Carpita et al, 1993, Plant J 3, 1-30.
Chen Jian Bai et al,1988, Plant Physiol Comm 4, 30-32.
Cho et al, 2006, FEBS Lett 580(13), 3136-3144.
Hayashi et al, 1988, Carbohyd Res 181, 273-277.

* cited by examiner

*Primary Examiner* — Thor Nielsen
(74) *Attorney, Agent, or Firm* — Robert Starnes

(57) ABSTRACT

The present invention relates to methods for modifying an agricultural crop comprising treating the agricultural crop with a composition comprising a xyloglucan endotransglycosylase and (a) a polymeric xyloglucan and a functionalized xyloglucan oligomer comprising a chemical group; (b) a polymeric xyloglucan functionalized with a chemical group and a functionalized xyloglucan oligomer comprising a chemical group; (c) a polymeric xyloglucan functionalized with a chemical group and a xyloglucan oligomer; (d) a polymeric xyloglucan, and a xyloglucan oligomer; (e) a polymeric xyloglucan functionalized with a chemical group; (f) a polymeric xyloglucan; (g) a functionalized xyloglucan oligomer comprising a chemical group; or (h) a xyloglucan oligomer, or (a-h) without a xyloglucan endotransglycosylase, in a medium under conditions leading to a modified agricultural crop possessing an improved property compared to the unmodified agricultural crop. The present invention also relates to a modified agricultural crop obtained by such methods.

13 Claims, 16 Drawing Sheets

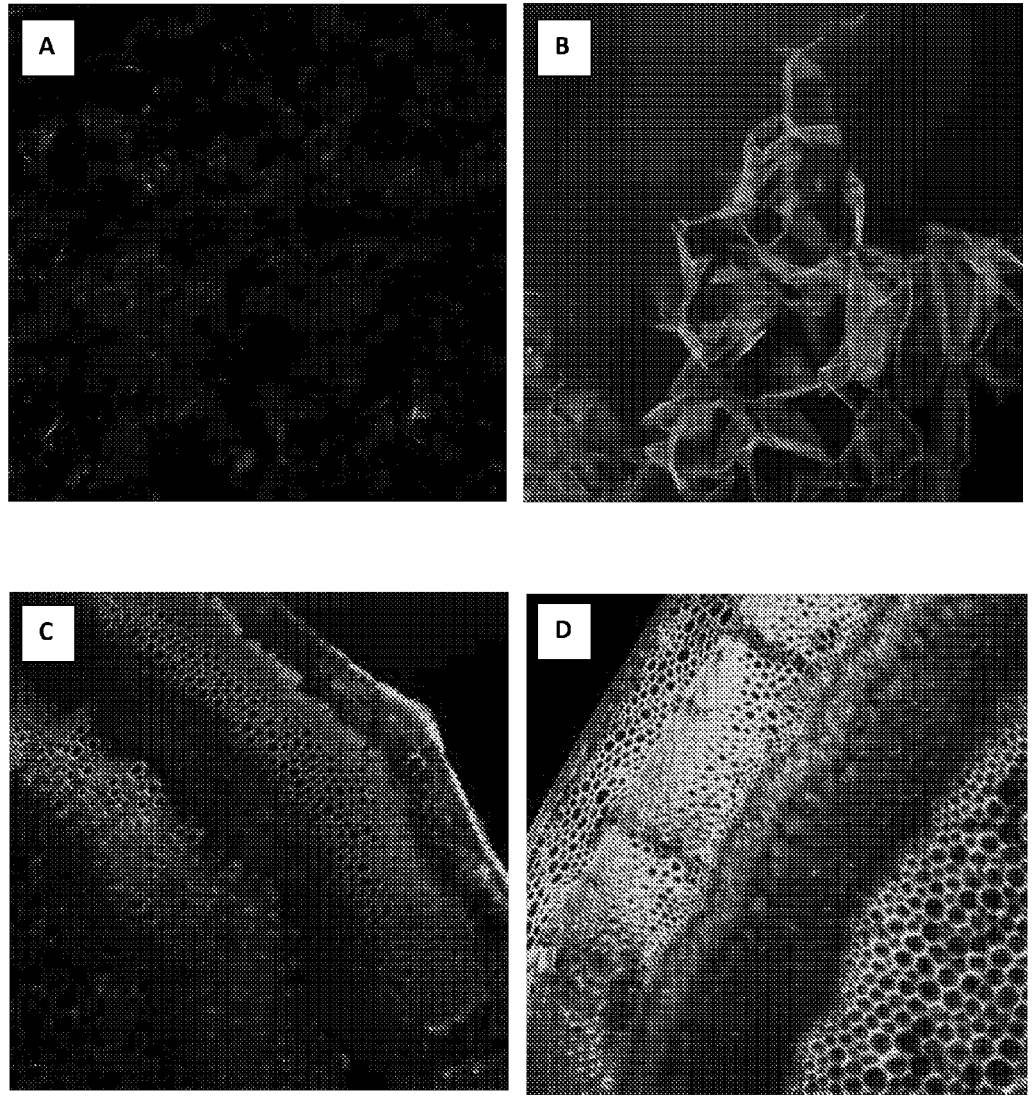
Fig. 11A, B, C, D

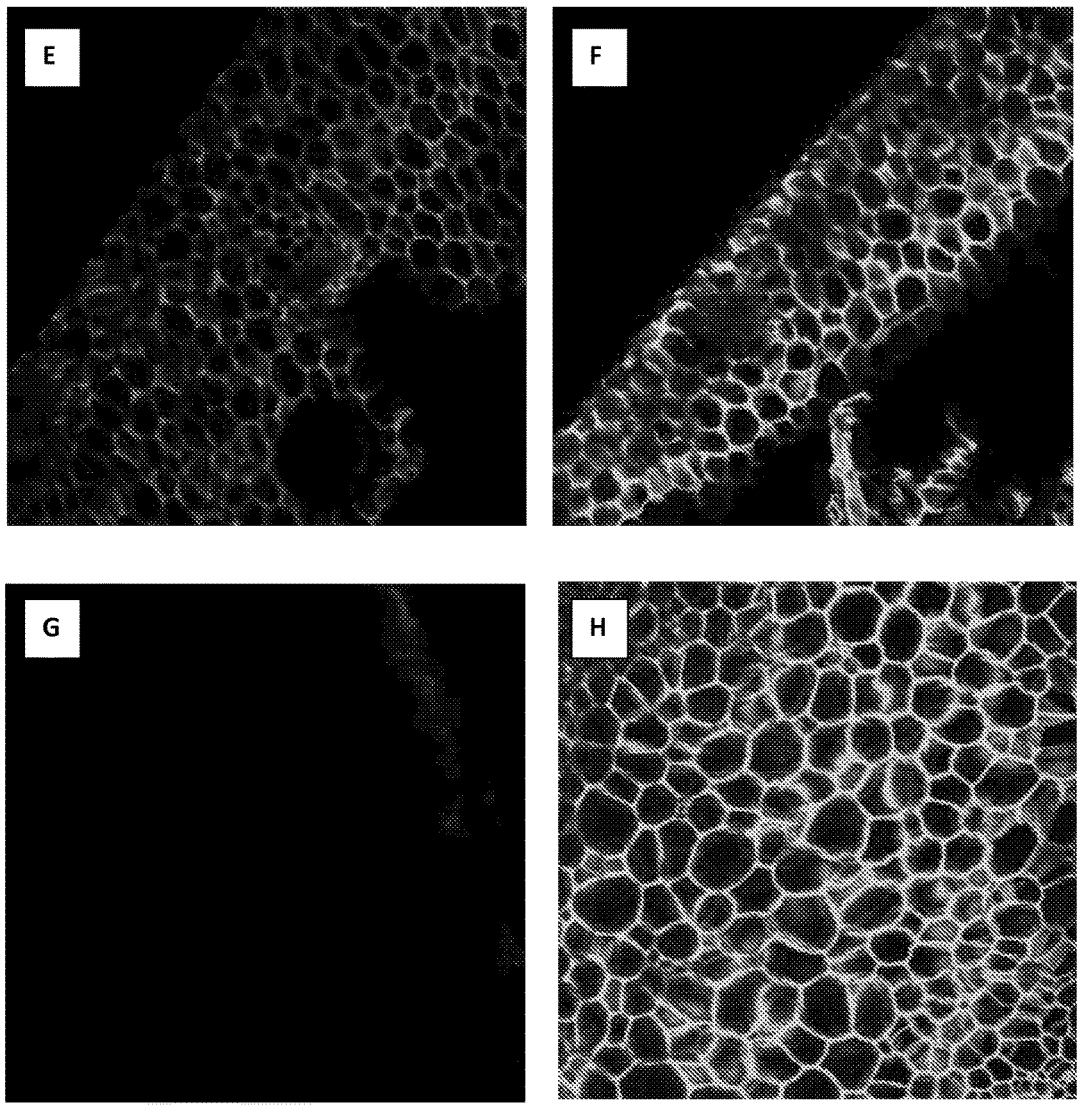
Fig. 11E, F, G, H

SEQUENCE LISTING

<160> NUMBER OF SEQ ID NOS: 22

<210> SEQ ID NO 1
<211> LENGTH: 879
<212> TYPE: DNA
<213> ORGANISM: Vigna angularis

<400> SEQUENCE: 1

```
atgggttctt ctttgtggac ttgtctgatt ctgttatcac tggcttctgc ttctttcgct      60
gccaacccaa gaactccaat tgatgtacca tttggcagaa actatgtgcc tacttgggcc     120
tttgatcata tcaaatatct caatggaggt tctgagattc agcttcatct cgataagtac     180
actggtactg gattccagtc caaagggtca tacttgtttg gtcacttcag catgtacata     240
aaattggttc ctggtgattc agctggcaca gtcactgctt tctatttatc gtccacaaac     300
gcagaacatg atgaaataga cttcgagttc ttgggaaaca gaactgggca accatacatt     360
ttacaaacaa atgtgttcac cggaggcaaa ggtgacagag agcagagaat ctacctctgg     420
tttgacccta cgactcaata ccacagatat tcagtgctat ggaacatgta ccagattgta     480
ttctatgtgg atgactaccc aataagggtg ttcaagaaca gcaatgactt gggagtgaag     540
ttccccttca atcaaccaat gaaaatatac aacagtttgt ggaatgcaga tgactgggct     600
acaaggggtg gtttggagaa aacagattgg tccaaagccc ccttcatagc ctcttacaag     660
ggcttccaca ttgatgggtg tgaggcctca gtgaatgcca agttctgtga cacacaaggc     720
aagaggtggt gggatcaacc agagtttcgt gaccttgatg ctgctcagtg caaaaactg      780
gcttgggtac gcaacaaata ccaccatctac aactactgca ctgatcgcaa acgctactct     840
caagtccctc cagagtgcac cagagaccgt gacatttaa                            879
```

<210> SEQ ID NO 2
<211> LENGTH: 876
<212> TYPE: DNA
<213> ORGANISM: Vigna angularis

<400> SEQUENCE: 2

```
atgggctcgt ccctctggac ttgtttgatc ctcctctcct tggcatcggc atccttcgca      60
gcgaaccctc gaactccgat cgatgtgcct ttcggacgga actacgtgcc gacatgggca     120
ttcgaccaca ttaagtattt gaacggaggc tcggagatcc agttgcatct cgacaagtac     180
accggcactg gtttccagtc gaagggctcc tacttgttcg acatttctc catgtacatc      240
aaattggtgc ctggtgactc ggcaggaact gtcaccgcat tctacctctc gtcgacaaac     300
gcagagcatg acgaaatcga cttcgagttc ctcggcaaca ggacaggaca gccgtacatc     360
ctccagacca cgtcttcac aggaggcaaa ggtgatcggg aacagcggat ctacttgtgg      420
ttcgatccca aacccagta ccataggtac tcggtgctct ggaacatgta tcagatcgtc      480
ttctacgtcg acgattatcc gatccgagtg ttcaagaact ccaacgactt gggcgtcaaa     540
ttccccttca accagcccat gaagatttac aactcgttgt ggaacgccga cgattgggca     600
accaggggtg gtctcgagaa gacagattgg tcgaaagcac cttcatcgc gtcgtacaag      660
ggtttccaca tcgacggatg tgaagcctcc gtgaacgcca agttctgtga cacccagggc     720
aaacgatggt gggatcagcc ggaattccgg gatttggatg cagcccagtg cagaagctc      780
gcgtgggtca ggaacaagta caccatctat aactactgta ccgatcggaa acgatattcg     840
caggtgcctc ccgagtgtac acgcgatagg gacatc                               876
```

<210> SEQ ID NO 3
<211> LENGTH: 292
<212> TYPE: PRT
<213> ORGANISM: Vigna angularis

<400> SEQUENCE: 3

Met Gly Ser Ser Leu Trp Thr Cys Leu Ile Leu Leu Ser Leu Ala Ser

```
  1               5                  10                 15
Ala Ser Phe Ala Ala Asn Pro Arg Thr Pro Ile Asp Val Pro Phe Gly
            20                  25                  30

Arg Asn Tyr Val Pro Thr Trp Ala Phe Asp His Ile Lys Tyr Leu Asn
            35                  40                  45

Gly Gly Ser Glu Ile Gln Leu His Leu Asp Lys Tyr Thr Gly Thr Gly
            50                  55                  60

Phe Gln Ser Lys Gly Ser Tyr Leu Phe Gly His Phe Ser Met Tyr Ile
 65                  70                  75                  80

Lys Leu Val Pro Gly Asp Ser Ala Gly Thr Val Thr Ala Phe Tyr Leu
                85                  90                  95

Ser Ser Thr Asn Ala Glu His Asp Glu Ile Asp Phe Glu Phe Leu Gly
            100                 105                 110

Asn Arg Thr Gly Gln Pro Tyr Ile Leu Gln Thr Asn Val Phe Thr Gly
            115                 120                 125

Gly Lys Gly Asp Arg Glu Gln Arg Ile Tyr Leu Trp Phe Asp Pro Thr
            130                 135                 140

Thr Gln Tyr His Arg Tyr Ser Val Leu Trp Asn Met Tyr Gln Ile Val
145                 150                 155                 160

Phe Tyr Val Asp Asp Tyr Pro Ile Arg Val Phe Lys Asn Ser Asn Asp
                165                 170                 175

Leu Gly Val Lys Phe Pro Phe Asn Gln Pro Met Lys Ile Tyr Asn Ser
            180                 185                 190

Leu Trp Asn Ala Asp Asp Trp Ala Thr Arg Gly Gly Leu Glu Lys Thr
            195                 200                 205

Asp Trp Ser Lys Ala Pro Phe Ile Ala Ser Tyr Lys Gly Phe His Ile
            210                 215                 220

Asp Gly Cys Glu Ala Ser Val Asn Ala Lys Phe Cys Asp Thr Gln Gly
225                 230                 235                 240

Lys Arg Trp Trp Asp Gln Pro Glu Phe Arg Asp Leu Asp Ala Ala Gln
                245                 250                 255

Trp Gln Lys Leu Ala Trp Val Arg Asn Lys Tyr Thr Ile Tyr Asn Tyr
            260                 265                 270

Cys Thr Asp Arg Lys Arg Tyr Ser Gln Val Pro Pro Glu Cys Thr Arg
            275                 280                 285

Asp Arg Asp Ile
            290

<210> SEQ ID NO 4
<211> LENGTH: 864
<212> TYPE: DNA
<213> ORGANISM: Arabidopsis thaliana

<400> SEQUENCE: 4
atggcgtgtt tcgcaaccaa acagcctctg ttgttgtctc tcctccttgc cattggcttc      60
tttgtggtgg ctgcatctgc cggaaacttc tatgagagct ttgatatcac ttggggtaat     120
ggtcgtgcca acatattcga gaatggacag cttctcactt gtactcttga caaggtctcc     180
ggctcaggtt ttcaatccaa gaggagtac ttgtttggta agatcgacat gaagctcaag      240
cttgtcgctg gaaactctgc tggcaccgtc accgcctact acctatcgtc aaaaggcacg     300
gcatgggatg agattgactt cgagtttttg ggaaatcgca caggacatcc ttacactatc     360
cacaccaatg tgttcaccgg aggtaaaggc gaccgtgaga tgcagttccg tctctggttc     420
gatcccactg cggatttcca cacctacacc gtccactgga accctgttaa catcatcttc     480
```

```
cttgtggatg ggatcccaat tcgggtgttc aagaacaacg agaaaaatgg ggtggcttac    540
cctaagaacc agccgatgag gatatactca agcctttggg aagccgatga ctgggctaca    600
gaaggcggtc gcgtgaagat cgactggagc aacgcaccat tcaaggcctc ttacagaaac    660
ttcaacgacc aaagctcatg cagcaggaca tcaagctcaa aatgggtgac ttgcgagcca    720
aacagcaact cgtggatgtg gacgactctc aatcctgccc agtacggaaa aatgatgtgg    780
gtgcaacgag acttcatgat ctacaactat tgtaccgatt ttaagagatt ccctcaaggc    840
ctccccaagg agtgtaaaact ttga                                           864
```

<210> SEQ ID NO 5
<211> LENGTH: 861
<212> TYPE: DNA
<213> ORGANISM: Arabidopsis thaliana

<400> SEQUENCE: 5

```
atggcctgtt tcgcaaccaa acagccgttg ttgctctcct tgttgctcgc catcggtttc     60
ttcgtggtgg cagcctccgc aggaaacttc tatgagtcct tcgacatcac ctggggcaac    120
ggaagggcga acatttttcga aaacggtcag ctcctcactt gtacgctcga caaggtgtcc    180
ggctccggtt tccagtcgaa gaaggagtac ttgttcggca agatcgacat gaagctcaag    240
ttggtggcag gtaactcggc aggtaccgtc acagcgtact attttgtcgtc caagggaact    300 gcgtgggacg aaatcgactt cgagttcctc ggcaaccgta caggacaccc ctacactatt    360
cacaccaacg tcttcaccgg aggcaagggt gatcgggaga tgcagttcag gctctggttc    420
gacccgacag cggatttcca tacttacacg gtgcattgga accccgtcaa catcattttc    480
ctcgtcgacg gaatccccat ccgagtcttc aagaacaacg agaagaacgg tgtggcgtat    540
cccaaaaacc agccgatgcg catctactcc tcgttgtggg aagcggacga ctgggccaca    600
gaaggcggac gcgtcaagat cgactggtcg aacgcaccgt tcaaggcgtc gtaccggaac    660
ttcaacgacc agtcgtcctg ttcgaggact tcgtcgtcca gtgggtcac ctgtgaaccc    720 aactcgaact cgtggatgtg gactactctc aaccctgccc agtacggcaa gatgatgtgg    780
gtgcagaggg acttcatgat ctacaactat tgtaccgatt tcaaacgatt ccctcagggt    840
ctccccaagg aatgtaaaact c                                              861
```

<210> SEQ ID NO 6
<211> LENGTH: 287
<212> TYPE: PRT
<213> ORGANISM: Arabidopsis thaliana

<400> SEQUENCE: 6

```
Met Ala Cys Phe Ala Thr Lys Gln Pro Leu Leu Leu Ser Leu Leu Leu
1               5                   10                  15

Ala Ile Gly Phe Phe Val Val Ala Ala Ser Ala Gly Asn Phe Tyr Glu
            20                  25                  30

Ser Phe Asp Ile Thr Trp Gly Asn Gly Arg Ala Asn Ile Phe Glu Asn
        35                  40                  45

Gly Gln Leu Leu Thr Cys Thr Leu Asp Lys Val Ser Gly Ser Gly Phe
    50                  55                  60

Gln Ser Lys Lys Glu Tyr Leu Phe Gly Lys Ile Asp Met Lys Leu Lys
65                  70                  75                  80

Leu Val Ala Gly Asn Ser Ala Gly Thr Val Thr Ala Tyr Tyr Leu Ser
                85                  90                  95
```

Ser Lys Gly Thr Ala Trp Asp Glu Ile Asp Phe Glu Phe Leu Gly Asn
100                 105                 110

Arg Thr Gly His Pro Tyr Thr Ile His Thr Asn Val Phe Thr Gly Gly
        115                 120                 125

Lys Gly Asp Arg Glu Met Gln Phe Arg Leu Trp Phe Asp Pro Thr Ala
130                 135                 140

Asp Phe His Thr Tyr Thr Val His Trp Asn Pro Val Asn Ile Ile Phe
145                 150                 155                 160

Leu Val Asp Gly Ile Pro Ile Arg Val Phe Lys Asn Asn Glu Lys Asn
                165                 170                 175

Gly Val Ala Tyr Pro Lys Asn Gln Pro Met Arg Ile Tyr Ser Ser Leu
            180                 185                 190

Trp Glu Ala Asp Asp Trp Ala Thr Glu Gly Gly Arg Val Lys Ile Asp
        195                 200                 205

Trp Ser Asn Ala Pro Phe Lys Ala Ser Tyr Arg Asn Phe Asn Asp Gln
210                 215                 220

Ser Ser Cys Ser Arg Thr Ser Ser Lys Trp Val Thr Cys Glu Pro
225                 230                 235                 240

Asn Ser Asn Ser Trp Met Trp Thr Thr Leu Asn Pro Ala Gln Tyr Gly
                245                 250                 255

Lys Met Met Trp Val Gln Arg Asp Phe Met Ile Tyr Asn Tyr Cys Thr
            260                 265                 270

Asp Phe Lys Arg Phe Pro Gln Gly Leu Pro Lys Glu Cys Lys Leu
        275                 280                 285

<210> SEQ ID NO 7
<211> LENGTH: 50
<212> TYPE: DNA
<213> ORGANISM: Artificial Sequence
<220> FEATURE:
<223> OTHER INFORMATION: ARTIFICIAL DNA PRIMER

<400> SEQUENCE: 7
ttcctcaatc tctatatac acaactggcc atgggctcgt ccctctggac             50

<210> SEQ ID NO 8
<211> LENGTH: 48
<212> TYPE: DNA
<213> ORGANISM: Artificial Sequence
<220> FEATURE:
<223> OTHER INFORMATION: ARTIFICIAL DNA PRIMER

<400> SEQUENCE: 8
tgtcagtcac ctctagttaa ttagatgtcc ctatcgcgtg tacactcg              48

<210> SEQ ID NO 9
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 9
taattaacta gaggtgactg acacctggc                                   29

<210> SEQ ID NO 10
<211> LENGTH: 31
<212> TYPE: DNA
<213> ORGANISM: Artificial Sequence
<220> FEATURE:
<223> OTHER INFORMATION: Artificial DNA Primer

```
<400> SEQUENCE: 10
catggccagt tgtgtatata gaggattgag g                              31

<210> SEQ ID NO 11
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 11
acatgtcttt gataagctag cgggccgcat catgta                        36

<210> SEQ ID NO 12
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 12
tacatgatgc ggcccgctag cttatcaaag acatgt                        36

<210> SEQ ID NO 13
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 13
ttaatcgcct tgcagcacac cgcttcctcg ctcactgact c                  41

<210> SEQ ID NO 14
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 14
acaataaccc tgataaatgc ggaacaacac tcaaccctat ctcggtc            47

<210> SEQ ID NO 15
<211> LENGTH: 53
<212> TYPE: DNA
<213> ORGANISM: Artificial Sequence
<220> FEATURE:
<223> OTHER INFORMATION: Artificial DNA Primer

<400> SEQUENCE: 15
agatagggtt gagtgttgtt ccgcatttat cagggttatt gtctcatgag cgg     53

<210> SEQ ID NO 16
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 16
ttctacacga aggaaagagg aggagagagt tgaacctgga cg                 42

<210> SEQ ID NO 17
```

```
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 17
aggttcaact ctctcctcct ctttccttcg tgtagaagac cagacag            47

<210> SEQ ID NO 18
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 18
tcagtgagcg aggaagcggt gtgctgcaag gcgattaagt tgg                43

<210> SEQ ID NO 19
<211> LENGTH: 54
<212> TYPE: DNA
<213> ORGANISM: Artificial Sequence
<220> FEATURE:
<223> OTHER INFORMATION: Artificial DNA Primer

<400> SEQUENCE: 19
ttcctcaatc ctctatatac acaactggcc atggcctgtt tcgcaaccaa acag    54

<210> SEQ ID NO 20
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 20
agctcgctag agtcgaccta gagtttacat tccttgggga gaccctg            47

<210> SEQ ID NO 21
<211> LENGTH: 27
<212> TYPE: DNA
<213> ORGANISM: Artificial Sequence
<220> FEATURE:
<223> OTHER INFORMATION: Artificial DNA Primer

<400> SEQUENCE: 21
taggtcgact ctagcgagct cgagatc                                  27

<210> SEQ ID NO 22
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 22
catggccagt tgtgtatata gaggattgag gaaggaagag                    40
```

COMPOSITIONS AND METHODS FOR IMPROVING POST-HARVEST PROPERTIES OF AGRICULTURAL CROPS

CROSS-REFERENCE TO RELATED APPLICATIONS

This application is a 35 U.S.C. § 371 national application of PCT/US2015/019011 filed Mar. 5, 2015, which claims priority or the benefit under 35 U.S.C. § 119 of U.S. Provisional Application No. 61/948,232 filed Mar. 5, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to compositions and methods for improving properties of agricultural crops.

Description of the Related Art

Xyloglucan endotransglycosylase (XET) is an enzyme that catalyzes endotransglycosylation of xyloglucan, a structural polysaccharide of plant cell walls. The enzyme is present in most plants, and in particular, land plants. XET has been extracted from dicotyledons and monocotyledons.

Xyloglucan is present in cotton, paper, or wood fibers (Hayashi et al., 1988, *Carbohydrate Research* 181: 273-277) making strong hydrogen bonds to cellulose (Carpita and Gibeaut, 1993, *The Plant Journal* 3: 1-30). Adding xyloglucan endotransglycosylase to various cellulosic materials containing xyloglucan alters the xyloglucan mediated interlinkages between cellulosic fibers improving their strength, and maintaining the cellulose-structure while permitting the cellulose fibers to move relative to one another under force.

It is known in the art that much of the agricultural crops grown in greenhouses and particularly open fields is spoiled by exposure to the environment or to agricultural pests. It is desirable in the art to form physical protection or barriers around agricultural crops without the use of chemical or biological pesticides. U.S. Pat. No. 6,027,740; U.S. Pat. No. 6,069,112; U.S. Pat. No. 6,110,867, and U.S. Pat. No. 6,156,327 disclose methods of crop protection by generating a physical barrier around produce. It is also known that much of the produce harvested from fields, gardens and greenhouses is lost to spoilage before consumption or sale. The quantity of loss is estimated from 0 to 25% in first world nations, and 0 to 50% in third world nations, depending on the crop harvested, which extrapolates to substantial economic, nutritive and sociological loss. In first world nations, the majority of post-harvest loss is termed qualitative loss; produce not spoiled remains unconsumed or unsold due to negative appearance.

There is a need in the art to preserve agricultural crops, both in appearance and from spoilage, rot, or contamination. There is also a need in the art to extend the length of time between harvest and market over which harvested crops remain fresh in appearance. There is a further need in the art to preserve or slow the onset of spoilage or the appearance of spoilage for cut or prepared produce.

The present invention provides methods for improving properties of agricultural crops.

SUMMARY OF THE INVENTION

The present invention relates to methods for modifying an agricultural crop comprising treating the agricultural crop with a composition selected from the group consisting of (a) a composition comprising a xyloglucan endotransglycosylase, a polymeric xyloglucan, and a functionalized xyloglucan oligomer comprising a chemical group; (b) a composition comprising a xyloglucan endotransglycosylase, a polymeric xyloglucan functionalized with a chemical group, and a functionalized xyloglucan oligomer comprising a chemical group; (c) a composition comprising a xyloglucan endotransglycosylase, a polymeric xyloglucan functionalized with a chemical group, and a xyloglucan oligomer; (d) a composition comprising a xyloglucan endotransglycosylase, a polymeric xyloglucan, and a xyloglucan oligomer; (e) a composition comprising a xyloglucan endotransglycosylase and a polymeric xyloglucan functionalized with a chemical group; (f) a composition comprising a xyloglucan endotransglycosylase and a polymeric xyloglucan; (g) a composition comprising a xyloglucan endotransglycosylase and a functionalized xyloglucan oligomer comprising a chemical group; (h) a composition comprising a xyloglucan endotransglycosylase and a xyloglucan oligomer, and (i) a composition of (a), (b), (c), (d), (e), (f), (g), or (h) without a xyloglucan endotransglycosylase, wherein the modified agricultural crop possesses an improved property compared to the unmodified agricultural crop.

The present invention also relates to modified agricultural crops obtained by such methods.

The present invention also relates to modified agricultural crops comprising (a) a polymeric xyloglucan and a functionalized xyloglucan oligomer comprising a chemical group; (b) a polymeric xyloglucan functionalized with a chemical group and a functionalized xyloglucan oligomer comprising a chemical group; (c) a polymeric xyloglucan functionalized with a chemical group and a xyloglucan oligomer; (d) a polymeric xyloglucan and a xyloglucan oligomer; (e) a polymeric xyloglucan functionalized with a chemical group; (f) a polymeric xyloglucan; (g) a functionalized xyloglucan oligomer comprising a chemical group; or (h) a xyloglucan oligomer, wherein the modified agricultural crop possesses an improved property compared to the unmodified agricultural crop.

The present invention further relates to a composition selected from the group consisting of (a) a composition comprising a xyloglucan endotransglycosylase, a polymeric xyloglucan, and a functionalized xyloglucan oligomer comprising a chemical group; (b) a composition comprising a xyloglucan endotransglycosylase, a polymeric xyloglucan functionalized with a chemical group, and a functionalized xyloglucan oligomer comprising a chemical group; (c) a composition comprising a xyloglucan endotransglycosylase, a polymeric xyloglucan functionalized with a chemical group, and a xyloglucan oligomer; (d) a composition comprising a xyloglucan endotransglycosylase, a polymeric xyloglucan, and a xyloglucan oligomer; (e) a composition comprising a xyloglucan endotransglycosylase and a polymeric xyloglucan functionalized with a chemical group; (f) a composition comprising a xyloglucan endotransglycosylase and a polymeric xyloglucan; (g) a composition comprising a xyloglucan endotransglycosylase and a functionalized xyloglucan oligomer comprising a chemical group; (h) a composition comprising a xyloglucan endotransglycosylase and a xyloglucan oligomer, and (i) a composition of (a), (b), (c), (d), (e), (f), (g), or (h) without a xyloglucan endotransglycosylase.

BRIEF DESCRIPTION OF THE FIGURES

FIG. 8 shows the effect of dipping discs of Granny Smith apples in 40 mM sodium citrate pH 5.5 containing 1 mg/ml tamarind seed xyloglucan with or without 1.1 µM *Vigna angularis* xyloglucan endotransglycosylase 16 (VaXET16) or 5 ml of deionized water after incubation under ambient conditions for 3, 4, and 7 days.
FIG. 9A shows a pixel intensity histogram of apple slices not dipped after 4 days of incubation.
FIG. 9B shows a pixel intensity histogram of apple slices dipped in 40 mM sodium citrate pH 5.5 after 4 days of incubation.
FIG. 9C shows a pixel intensity histogram of apple slices dipped in xyloglucan after 4 days of incubation.
FIG. 9D shows a pixel intensity histogram of apple slices dipped in xyloglucan and VaXET16 after 4 days of incubation.
FIG. 9E shows a plot of the mean intensity vs. time for the variously treated apple slices.
FIG. 11A-11H shows a series of laser scanning confocal microscope images that compare a fruit, flower, or vegetable incubated with *Arabidopsis thaliana* xyloglucan endotransglycosylase 14 (AtXET14) in 150 mM sodium chloride-20 mM phosphate pH 7.2 to incubated with AtXET14 and fluorescein isothiocyanate-labeled xyloglucan (FITC-XG) in 150 mM sodium chloride-20 mM phosphate pH 7.2 overnight at ambient temperature.
FIG. 11A shows a confocal image of a section of an apple slice incubated with AtXET14.
FIG. 11B shows a confocal image of a section of an apple slice incubated with AtXET14 and FITC-XG.
FIG. 11C shows a confocal image of a section of a carnation stem incubated with AtXET14.
FIG. 11D shows a confocal image of a section of a carnation stem incubated with AtXET14 and FITC-XG.
FIG. 11E shows a confocal image of a section of a banana stem incubated with AtXET14.
FIG. 11F shows a confocal image of a section of a banana stem incubated with AtXET14 and FITC-XG.
FIG. 11G shows a confocal image of a section of a squash stem incubated with AtXET14.
FIG. 11H shows a confocal image of a section of a squash stem incubated with AtXET14 and FITC-XG.

DEFINITIONS

Figure 1:
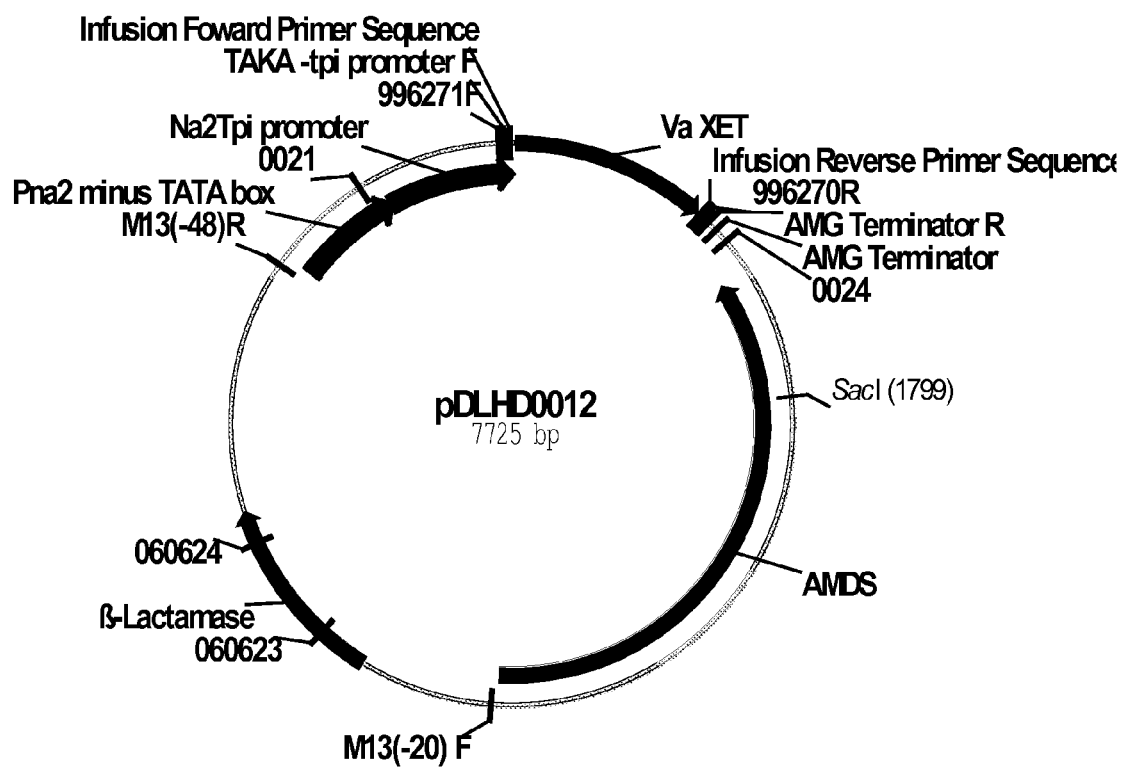
FIG. 1 shows a restriction map of pDLHD0012.

As used herein, the singular forms "a", "an", and "the" are intended to include the plural forms as well, unless the context clearly indicates otherwise.

Agricultural crop: The term "agricultural crop" means any plant or product thereof that is harvested at some point in its growth stage, such as fruits, vegetables, perishable plants, flowers, grains and other staple crops, medicinal herbs and plants, nuts or seeds, crops grown for spinning cloth or fibers, and perishable foodstuffs derived directly therefrom, for use or consumption by humans or animals.

Functionalized xyloglucan oligomer: The term "functionalized xyloglucan oligomer" means a short chain xyloglucan oligosaccharide, including single or multiple repeating units of xyloglucan, which has been modified by incorporating a chemical group. The xyloglucan oligomer is preferably 1 to 3 kDa in molecular weight, corresponding to 1 to 3 repeating xyloglucan units. The chemical group may be a compound of interest or a reactive group such as an aldehyde group, an amino group, an aromatic group, a carboxyl group, a halogen group, a hydroxyl group, a ketone group, a nitrile group, a nitro group, a sulfhydryl group, or a sulfonate group. The incorporated reactive groups can be derivatized with a compound of interest to provide a direct agricultural benefit or to coordinate metal cations and/or to bind other chemical entities that interact (e.g., covalently, hydrophobically, electrostatically, etc.) with the reactive groups. The derivatization can be performed directly on a functionalized xyloglucan oligomer comprising a reactive group or after the functionalized xyloglucan oligomer comprising a reactive group is incorporated into polymeric xyloglucan. Alternatively, the xyloglucan oligomer can be functionalized by incorporating directly a compound by using a reactive group contained in the compound, e.g., an aldehyde group, an amino group, an aromatic group, a carboxyl group, a halogen group, a hydroxyl group, a ketone group, a nitrile group, a nitro group, a sulfhydryl group, or a sulfonate group. The terms "functionalized xyloglucan oligomer" and "functionalized xyloglucan oligomer comprising a chemical group" are used interchangedly herein.

Polymeric xyloglucan: The term "polymeric xyloglucan" means short, intermediate or long chain xyloglucan oligosaccharide or polysaccharide encompassing more than one repeating unit of xyloglucan, e.g., multiple repeating units of xyloglucan. Most optimally, polymeric xyloglucan encompasses xyloglucan of 50-200 kDa number average molecular weight, corresponding to 50-200 repeating units. A repeating motif of xyloglucan is composed of a backbone of four beta-(1-4)-D-glucopyranose residues, three of which have a single alpha-D-xylopyranose residue attached at O-6. Some of the xylose residues are beta-D-galactopyranosylated at O-2, and some of the galactose residues are alpha-L-fucopyranosylated at O-2. The term "xyloglucan" herein is understood to mean polymeric xyloglucan.

Polymeric xyloglucan functionalized with a chemical group: The term "polymeric xyloglucan functionalized with a chemical group" means a polymeric xyloglucan that has been modified by incorporating a chemical group. The polymeric xyloglucan is short, intermediate or long chain xyloglucan oligosaccharide or polysaccharide encompassing more than one repeating unit of xyloglucan, e.g., multiple repeating units of xyloglucan. The polymeric xyloglucan encompasses xyloglucan of 50-200 kDa number average molecular weight, corresponding to 50-200 repeating units. A repeating motif of xyloglucan is composed of a backbone of four beta-(1-4)-D-glucopyranose residues, three of which have a single alpha-D-xylopyranose residue attached at O-6. The chemical group may be a compound of interest or a reactive group such as an aldehyde group, an amino group, an aromatic group, a carboxyl group, a halogen group, a hydroxyl group, a ketone group, a nitrile group, a nitro group, a sulfhydryl group, or a sulfonate group. The chemical group can be incorporated into a polymeric xyloglucan by reacting the polymeric xyloglucan with a functionalized xyloglucan oligomer in the presence of xyloglucan endotransglycosylase. The incorporated reactive groups can then be derivatized with a compound of interest. The derivatization can be performed directly on a functionalized polymeric xyloglucan comprising a reactive group or after a functionalized xyloglucan oligomer comprising a reactive group is incorporated into a polymeric xyloglucan. Alternatively, the polymeric xyloglucan can be functionalized by incorporating directly a compound by using a reactive group contained in the compound, e.g., an aldehyde group, an amino group, an aromatic group, a carboxyl group, a halogen group, a hydroxyl group, a ketone group, a nitrile group, a nitro group, a sulfhydryl group, or a sulfonate group.

Xyloglucan endotransglycosylase: The term "xyloglucan endotransglycosylase" means a xyloglucan:xyloglucan xyloglucanotransferase (EC 2.4.1.207) that catalyzes cleavage of a β-(1→4) bond in the backbone of a xyloglucan and transfers the xyloglucanyl segment on to O-4 of the non-reducing terminal glucose residue of an acceptor, which can be a xyloglucan or an oligosaccharide of xyloglucan. Xyloglucan endotransglycosylases are also known as xyloglucan endotransglycosylase/hydrolases or endo-xyloglucan transferases. Some xylan endotransglycosylases can possess different activities including xyloglucan and mannan endotransglycosylase activities. For example, xylan endotransglycosylase from ripe papaya fruit can use heteroxylans, such as wheat arabinoxylan, birchwood glucuronoxylan, and others as donor molecules. These xylans can potentially play a similar role as xyloglucan while being much cheaper in cost since they can be extracted, for example, from pulp mill spent liquors and/or future biomass biorefineries.

Xyloglucan endotransglycosylase activity can be assayed by those skilled in the art using any of the following methods. The reduction in the average molecular weight of a xyloglucan polymer when incubated with a molar excess of xyloglucan oligomer in the presence of xyloglucan endotransglycosylase can be determined via liquid chromatography (Sulova et al., 2003, *Plant Physiol. Biochem.* 41: 431-437) or via ethanol precipitation (Yaanaka et al., 2000, *Food Hydrocolloids* 14: 125-128) followed by gravimetric or cellulose-binding analysis (Fry et al., 1992, *Biochem. J.* 282: 821-828), or can be assessed colorimetrically by association with iodine under alkaline conditions (Sulova et al., 1995, *Analytical Biochemistry* 229: 80-85). Incorporation of a functionalized xyloglucan oligomer into a xyloglucan polymer by incubation of the functionalized oligomer with xyloglucan in the presence of xyloglucan endotransglycosylase can be assessed, e.g., by incubating a radiolabeled xyloglucan oligomer with xyloglucan and xyloglucan endotransglycosylase, followed by filter paper-binding and measurement of filter paper radioactivity, or incorporation of a fluorescently or optically functionalized xyloglucan oligomer can be assessed similarly, monitoring fluorescence or colorimetrically analyzing the filter paper.

Xyloglucan oligomer: The term "xyloglucan oligomer" means a short chain xyloglucan oligosaccharide, including single or multiple repeating units of xyloglucan. Most optimally, the xyloglucan oligomer will be 1 to 3 kDa in molecular weight, corresponding to 1 to 3 repeating xyloglucan units.

DETAILED DESCRIPTION OF THE INVENTION

The present invention relates to methods for modifying an agricultural crop comprising treating the agricultural crop with a composition selected from the group consisting of (a) a composition comprising a xyloglucan endotransglycosylase, a polymeric xyloglucan, and a functionalized xyloglucan oligomer comprising a chemical group; (b) a composition comprising a xyloglucan endotransglycosylase, a polymeric xyloglucan functionalized with a chemical group, and a functionalized xyloglucan oligomer comprising a chemical group; (c) a composition comprising a xyloglucan endotransglycosylase, a polymeric xyloglucan functionalized with a chemical group, and a xyloglucan oligomer; (d) a composition comprising a xyloglucan endotransglycosylase, a polymeric xyloglucan, and a xyloglucan oligomer; (e) a composition comprising a xyloglucan endotransglycosylase and a polymeric xyloglucan functionalized with a chemical group; (f) a composition comprising a xyloglucan endotransglycosylase and a polymeric xyloglucan; (g) a composition comprising a xyloglucan endotransglycosylase and a functionalized xyloglucan oligomer comprising a chemical group; (h) a composition comprising a xyloglucan endotransglycosylase and a xyloglucan oligomer, and (i) a composition of (a), (b), (c), (d), (e), (f), (g), or (h) without a xyloglucan endotransglycosylase, wherein the modified agricultural crop possesses an improved property compared to the unmodified agricultural crop.

The present invention also relates to modified agricultural crops obtained by such methods.

The present invention also relates to modified agricultural crops comprising (a) a polymeric xyloglucan and a functionalized xyloglucan oligomer comprising a chemical group; (b) a polymeric xyloglucan functionalized with a chemical group and a functionalized xyloglucan oligomer comprising a chemical group; (c) a polymeric xyloglucan functionalized with a chemical group and a xyloglucan oligomer; (d) a polymeric xyloglucan and a xyloglucan oligomer; (e) a polymeric xyloglucan functionalized with a chemical group; (f) a polymeric xyloglucan; (g) a functionalized xyloglucan oligomer comprising a chemical group; or (h) a xyloglucan oligomer, wherein the modified agricultural crop possesses an improved property compared to the unmodified agricultural crop.

The present invention further relates to a composition selected from the group consisting of (a) a composition comprising a xyloglucan endotransglycosylase, a polymeric xyloglucan, and a functionalized xyloglucan oligomer comprising a chemical group; (b) a composition comprising a xyloglucan endotransglycosylase, a polymeric xyloglucan functionalized with a chemical group, and a functionalized xyloglucan oligomer comprising a chemical group; (c) a composition comprising a xyloglucan endotransglycosylase, a polymeric xyloglucan functionalized with a chemical group, and a xyloglucan oligomer; (d) a composition comprising a xyloglucan endotransglycosylase, a polymeric xyloglucan, and a xyloglucan oligomer; (e) a composition comprising a xyloglucan endotransglycosylase and a polymeric xyloglucan functionalized with a chemical group; (f) a composition comprising a xyloglucan endotransglycosylase and a polymeric xyloglucan; (g) a composition comprising a xyloglucan endotransglycosylase and a functionalized xyloglucan oligomer comprising a chemical group; (h) a composition comprising a xyloglucan endotransglycosylase and a xyloglucan oligomer, and (i) a composition of (a), (b), (c), (d), (e), (f), (g), or (h) without a xyloglucan endotransglycosylase.

In one embodiment, the composition comprises a xyloglucan endotransglycosylase, a polymeric xyloglucan, and a functionalized xyloglucan oligomer comprising a chemical group. In another embodiment, the composition comprises a xyloglucan endotransglycosylase, a polymeric xyloglucan functionalized with a chemical group, and a functionalized xyloglucan oligomer comprising a chemical group. In another embodiment, the composition comprises a xyloglucan endotransglycosylase, a polymeric xyloglucan functionalized with a chemical group, and a xyloglucan oligomer. In another embodiment, the composition comprises a xyloglucan endotransglycosylase, a polymeric xyloglucan, and a xyloglucan oligomer. In another embodiment, the composition comprises a xyloglucan endotransglycosylase and a polymeric xyloglucan functionalized with a chemical group. In another embodiment, the composition comprises a xyloglucan endotransglycosylase and a polymeric xyloglucan. In another embodiment, the composition comprises a xyloglucan endotransglycosylase and a functionalized xyloglucan oligomer comprising a chemical group. In another embodiment, the composition comprises a xyloglucan endotransglycosylase and a xyloglucan oligomer.

In another embodiment, the composition comprises a polymeric xyloglucan and a functionalized xyloglucan oligomer comprising a chemical group. In another embodiment, the composition comprises a polymeric xyloglucan functionalized with a chemical group and a functionalized xyloglucan oligomer comprising a chemical group. In another embodiment, the composition comprises a polymeric xyloglucan functionalized with a chemical group and a xyloglucan oligomer. In another embodiment, the composition comprises a polymeric xyloglucan and a xyloglucan oligomer. In another embodiment, the composition comprises a polymeric xyloglucan functionalized with a chemical group. In another embodiment, the composition comprises a polymeric xyloglucan. In another embodiment, the composition comprises a functionalized xyloglucan oligomer comprising a chemical group. In another embodiment, the composition comprises a xyloglucan oligomer.

The modification of an agricultural crop with a composition of the present invention can be conducted in any useful medium. In an embodiment, the medium is an aqueous medium. In another embodiment, the medium is a partially aqueous medium. In another aspect, the medium is a slurry. In another aspect, the medium is an aqueous slurry. In another aspect, the medium is a non-aqueous slurry. In another aspect, the medium is a partially aqueous slurry. In another aspect, the medium is a waxy suspension. In another aspect, the medium is an emulsion.

In one aspect, the agricultural crop is harvested. In another aspect, the agricultural crop is not harvested.

The methods of the present invention prevent qualitative and quantitative loss of agricultural crops and processed crops thereof. Once harvested, produce rapidly undergoes senescence, degrades in appearance, nutrition value, texture, firmness, and/or desirability. In a related manner, once harvested, produce can be spoiled by microbial degradation. Once the protective skins, peels, or rinds of produce are pierced, the produce is subject to oxidative damage, dehydration, loss of desirable appearance, and potential microbial degradation. Following harvest, produce is shipped to wholesalers, dealers, and/or aggregators, and then to consumer markets. Sale must be necessarily expedited to minimize loss, thereby increasing associated costs. Treating cut flowers, fruits, vegetables or other agricultural crops with a solution of polymeric xyloglucan, a naturally occurring plant polysaccharide, or more preferably with a solution of polymeric xyloglucan and xyloglucan endotransglycosylase provides protection of the treated produce from, for example, degradation, spoilage, and the onset of negative appearance. The polymeric xyloglucan can be functionalized with a compound, for example, with preservatives or hydrophobic chemical moieties, and the presence of xyloglucan endotransglycosylase permits surface coating of the produce with the introduced functionalization having, for example, the effect of preventing loss of water and keeping the produce from drying out. Food-safe anti-microbial compounds, such as bacteriostatic or bacteriocidal compounds, can similarly be introduced in this manner.

In one aspect, the functionalization can provide any functionally useful chemical moiety.

The xyloglucan endotransglycosylase is preferably present at about 0.1 nM to about 1 mM, e.g., about 10 nM to about 100 µM or about 0.5 µM to about 5 µM, in the composition.

The polymeric xyloglucan or polymeric xyloglucan functionalized with a chemical group is preferably present at about 1 mg per g to about 1 g per g of the composition, e.g., about 10 mg to about 950 mg or about 100 mg to about 900 mg per g of the composition.

When the xyloglucan oligomer or the functionalized xyloglucan oligomer is present without polymeric xyloglucan or polymeric xyloglucan functionalized with a chemical group, the xyloglucan oligomer or the functionalized xyloglucan oligomer is preferably present at about 1 mg to about 1 g per g of the composition, e.g., about 10 mg to about 950 mg or about 100 mg to about 900 mg per g of the composition.

When present with the polymeric xyloglucan or polymeric xyloglucan functionalized with a chemical group, the xyloglucan oligomer or the functionalized xyloglucan oligomer is preferably present with the polymeric xyloglucan at about 50:1 to about 0.5:1 molar ratio of xyloglucan oligomer or functionalized xyloglucan oligomer to polymeric xyloglucan or polymeric xyloglucan functionalized with a chemical group, e.g., about 10:1 to about 1:1 or about 5:1 to about 1:1 molar ratio of xyloglucan oligomer or functionalized xyloglucan oligomer to polymeric xyloglucan or polymeric xyloglucan functionalized with a chemical group.

The polymeric xyloglucan or polymeric xyloglucan functionalized with a chemical group is preferably present at about 1 ng to about 1 g per g of the agricultural crop, e.g., about 10 µg to about 100 mg or about 1 mg to about 50 mg per g of the agricultural crop.

When the xyloglucan oligomer or the functionalized xyloglucan oligomer is present without polymeric xyloglucan or polymeric xyloglucan functionalized with a chemical group, the xyloglucan oligomer or the functionalized xyloglucan oligomer is preferably present at about 1 ng per g to about 1 g per g of the agricultural crop, e.g., about 10 µg to about 100 mg or about 1 mg to about 50 mg per g of the agricultural crop.

When present with the polymeric xyloglucan or polymeric xyloglucan functionalized with a chemical group, the xyloglucan oligomer or the functionalized xyloglucan oligomer is preferably present with the polymeric xyloglucan at about 50:1 to about 0.5:1, e.g., about 10:1 to about 1:1 or about 5:1 to about 1:1 molar ratio of xyloglucan oligomer or functionalized xyloglucan oligomer to polymeric xyloglucan or polymeric xyloglucan functionalized with a chemical group.

The xyloglucan endotransglycosylase is preferably present at about 0.1 nM to about 1 mM, e.g., about 10 nM to about 100 µM or about 0.5 µM to about 5 µM.

The concentration of polymeric xyloglucan, polymeric xyloglucan functionalized with a chemical group, xyloglucan oligomer, or functionalized xyloglucan oligomer comprising a chemical group incorporated onto or into the agricultural crop is about 1 µg to about 500 mg per g of the agricultural crop, e.g. about 0.1 µg to about 50 mg or about 1 to about 5 mg per g of the agricultural crop.

Agricultural Crops

In the methods of the present invention, the agricultural crops can be any plant, or part thereof, grown for human or animal use or consumption.

In one aspect, the agricultural crops are grown for human food. In another aspect, the agricultural crops are grown for silage. In another aspect, the agricultural crops are grown for animal or livestock feed. In another aspect, the agricultural crops are grown for seedlings, saplings, or transplant. In another aspect, the agricultural crops are ornamental. In another aspect, the agricultural crops are trees. In another aspect, the agricultural crops are trees grown for timber. In another aspect, the agricultural crops are trees grown as Christmas trees. In another aspect, the agricultural crops are trees grown for fruit, vegetable, or nut production. In another aspect, the agricultural crops are bushes or shrubs. In another aspect, the agricultural crops are grasses. In another aspect, the agricultural crops are flowers grown for the cut flower market. In another aspect, the agricultural crops are flowers grown as houseplants. In another aspect, the agricultural crops are grown for medicinal or homeopathic compounds. In another aspect, the agricultural crops are grown for fibers. In another aspect, the agricultural crop grown for fibers is cotton. In another aspect, the agricultural crop grown for fibers is hemp. In another aspect, the agricultural crop grown for fibers is flax. In another aspect, the agricultural crop grown for fibers is ramie. In another aspect, the agricultural crop grown for fibers is bamboo. In another aspect, the agricultural crops are grown for alcohol fermentation or beverage production. In another aspect, the agricultural crops are grown for dry distiller's grain.

In another aspect, the agricultural crop is a fruit. The fruit can be any type of fruit. The fruit can be apples, avocado, banana, berries, cucumbers, grape, tamarind, watermelon, cantaloupe, pumpkin, peach, plum, olive, orange, lemon, lime, pears, blackberry, pineapple, fig, mulberry, grains, sunflower, nuts, and non-botanical fruit. In one aspect, the fruit are berries, (e.g., raspberries, blueberries, grapes, lingonberries, tomatoes, eggplant, cranberries, guava, pomegranate, chillies, and cucumbers). In another aspect, the fruit are pepo (e.g., watermelon, cantaloupe, and pumpkin). In another aspect, the fruit are drupe (e.g., peach, plum, and olive). In another aspect, the fruit are follicles. In another aspect, the fruit are capsules (e.g., horse chestnut, cotton, and *eucalyptus*). In another aspect, the fruit are hesperidium (e.g., oranges, tangerines, grapefruits, lemons, and limes). In another aspect, the fruit are accessory fruit (e.g., apples and pears). In another aspect, the fruit are aggregate fruit (e.g., blackberries, pineapples, and figs). In another aspect, the fruit are multiple fruit (e.g., mulberries). In another aspect, the fruit are Achene (e.g., sunflower). In another aspect, the fruit are nuts (e.g., walnut, oak, peanut, and almond). In another aspect, the fruit are non-botanical fruit (e.g., juniper berries and rhubarb).

In another aspect, the agricultural crop is a vegetable. The vegetable can be any edible plant or part thereof. The vegetables can be artichokes, asparagus, barley, bean sprouts, beans, black mustard, broccoli, Brussel sprouts, carrots, cauliflower, celery, clover, flax, garlic, ginger, hemp, India mustard, kale, kohlrabi, leek, lentil, lettuce, maize (corn), millet, oats, onion, pea, peanut, poppy, potatoes, radish, rhubarb, rice, rye, shallots, *sorghum*, soy, spinach, sweet potato, tamarind, triticale, watercress, or wheat.

In another aspect, the vegetable arises from the flower bud of a plant (e.g., broccoli, cauliflower, and artichokes). In another aspect, the vegetable arises from plant leaves (e.g., spinach, lettuce, kale, and watercress). In another aspect, the vegetable arises from plant buds (e.g., Brussel sprouts). In another aspect, the vegetable arises from plant shoots (e.g., asparagus and bean sprouts). In another aspect, the vegetable arises from plant stems (e.g., ginger and kohlrabi). In another aspect, the vegetable arises from plant tubers (e.g., potatoes and sweet potatoes). In another aspect, the vegetable arises from leaf stems (e.g., celery and rhubarb). In another aspect, the vegetable arises from plant roots (e.g., carrots and radishes). In another aspect, the vegetable arises from plant bulbs (e.g., onions and shallots).

The vegetables can be leguminous vegetables, including the plants or seed of beans, soy, pea, lentil, clover, peanut, tamarind, and wisteria.

In another aspect, the agricultural crop is a grain. In another aspect, the grains are wheat, rice, oats, rye, triticale or barley. In another aspect, the grains are millet, *sorghum*, or maize (corn). In another aspect, the grains are mustards (e.g., black mustard and India mustard). In another aspect, the grains are grain legumes (e.g., peas, lentils, and beans). In another aspect, the grains are flax, hemp, or poppy.

In another aspect, the agricultural crop is a flower. The flower can be any flower. In one aspect, the flowers are field grown cut flowers. In another aspect, the flowers are greenhouse grown cut flowers. The flower can be *Ageratum houstonianum, Ammi majus, Antirrhinum majus, Callistephus chinensis, Celosia cristata, Centaurea cyanus, Centaurea Americana, Clarkia amoena, Consolida regalis, Dianthus barbatus, Eustoma grandiflorum, Gypsophila elegans, Helianthus debilis cucumerifolius, Iberis amara, Limonium sinuatum, Nigella damascena, Scabiosa atropurpurea, Zinnia elegans, Achillea filipendulina, Artemisia ludoviciana, Asclepias incarnate, Asclepias tuberosa, Aster novi-belgii, Aster ericoides, Astilbe, Chrysanthemum×superbum, Echinops bannaticus, Echinops exaltatus, Echinops ritro, Echinops sphaerocephalus, Eryngium amethystinum, Eryngium planum, Eryngium alpinum, Gypsophila paniculata, Liatris, Paeonia, Platycodon grandiflorum, Salvia farinacea, Scabiosa caucasica, Solidago, Allium, Gladiolus, Lilium, Rosa, Antirrhinum, Gerbera, Tulipa,* or *Gladiolus.*

In one aspect, the cut flowers are annuals. The annual flowers can be *Ageratum houstonianum, Ammi majus, Antirrhinum majus, Callistephus chinensis, Celosia cristata, Centaurea cyanus, Centaurea Americana, Clarkia amoena, Consolida regalis, Dianthus barbatus, Eustoma grandiflorum, Gypsophila elegans, Helianthus debilis cucumerifolius, Iberis amara, Limonium sinuatum, Nigella damascena, Scabiosa atropurpurea,* and *Zinnia elegans.*

In another aspect, the cut flowers are perennials. The perennial flowers can be *Achillea filipendulina, Artemisia ludoviciana, Asclepias incarnate, Asclepias tuberosa, Aster novi-belgii, Aster ericoides, Astilbe, Chrysanthemum×superbum, Echinops bannaticus, Echinops exaltatus, Echinops ritro, Echinops sphaerocephalus, Eryngium amethystinum, Eryngium planum, Eryngium alpinum, Gypsophila paniculata, Liatris, Paeonia, Platycodon grandiflorum, Salvia farinacea, Scabiosa caucasica,* and *Solidago.*

In another aspect, the cut flowers are bulbs. The flower bulbs can be *Allium, Gladiolus,* and *Lilium.* In another aspect, the cut flowers are traditionally cut flowers such as chrysanthemums, carnations, and roses. In another aspect, the cut flowers are nontraditional cut flowers such as lilies (*Lilium*), snapdragons (*Antirrhinum*), gerbera (*Gerbera*), tulips (*Tulipa*), and gladiolas (*Gladiolus*). In another aspect, the cut flowers are shipped from South America, Holland or the Caribbean. In another aspect, the cut flowers are shipped from local farms.

In another aspect, the agricultural crop is a spice. The spice can be Ajwain (*Trachyspermum ammi*), Akudjura (*Solanum centrale*), Alexanders (*Smyrnium olusatrum*), Alkanet (*Alkanna tinctoria*), Alligator pepper, Mbongo spice (*mbongochobi*), Hepper pepper (*Aframomum danielli, A. citratum, A. exscapum*), Allspice (*Pimenta dioica*), Angelica (*Angelica archangelica*), Anise (*Pimpinella anisum*), Anise Hyssop (*Agastache foeniculum*), Aniseed myrtle (*Syzygium anisatum*), Annatto (*Bixa orellana*), Apple mint (*Mentha suaveolens, Mentha×rotundifolia and Mentha×villosa*), Artemisia (*Artemisia* spp.), Asafoetida (*Ferula assafoetida*), Asarabacca (*Asarum europaeum*), Avens (*Geum urbanum*), Avocado leaf (*Peresea americana*), Barberry (*Berberis vulgaris* and other *Berberis* spp.), Sweet basil (*Ocimum basilicum*), Lemon basil (*Ocimum×citriodorum*), Thai basil (*O. basilicum* var. *thyrsiflora*), Holy Basil (*Ocimum tenuiflorum*), Bay leaf (*Laurus nobilis*), Bee balm (*Monarda didyma*), Boldo (*Peumus boldus*), Borage (*Borago officinalis*), Black cardamom (*Amomum subulatum, Amomum costatum*), Black mustard (*Brassica nigra*), Blue fenugreek, Blue melilot (*Trigonella caerulea*), Brown mustard (*Brassica juncea*), Caraway (*Carum carvi*), White mustard (*Sinapis alba*), White cardamom (*Elettaria cardamomum*), Carob (*Ceratonia siliqua*), Catnip (*Nepeta cataria*), Cassia (*Cinnamomum aromaticum*), Cayenne pepper (*Capsicum annuum*), Celery leaf (*Apium graveolens*), Celery seed (*Apium graveolens*), Chervil (*Anthriscus cerefolium*), Chicory (*Cichorium intybus*), Chili pepper (*Capsicum* spp.), Chives (*Allium schoenoprasum*), Sweet Cicely (*Myrrhis odorata*), Cilantro or coriander (*Coriandrum sativum*), Cinnamon, (*Cinnamomum burmannii, Cinnamomum loureiroi, Cinnamomum verum, Cinnamomum zeylanicum*), White Cinnamon (*Canella winterana*), Myrtle Cinnamon (*Backhousia myrtifolia*), Clary sage (*Salvia sclarea*), Clove (*Syzygium aromaticum*), Costmary (*Tanacetum balsamita*), Cuban oregano (*Plectranthus amboinicus*), Cubeb pepper (*Piper cubeba*), Cudweed (*Gnaphalium* spp.), Culantro, culangot or long coriander (*Eryngium foetidum*), Cumin (*Cuminum cyminum*), Curry leaf (*Murraya koenigii*), Curry plant (*Helichrysum italicum*), Dill (*Anethum graveolens*), Elderflower (*Sambucus* spp.), Epazote (*Dysphania ambrosioides*), Fennel (*Foeniculum vulgare*), Fenugreek (*Trigonella foenum-graecum*), File powder (*Sassafras albidum*), Fingerroot, Krachai or Temu kuntji (*Boesenbergia rotunda*), Greater Galangal (*Alpinia galanga*), Lesser Galangal (*Alpinia officinarum*), Galingale (*Cyperus* spp.), Garlic chives (*Allium tuberosum*), Garlic (*Allium sativum*), Elephant Garlic (*Allium ampeloprasum* var. *ampeloprasum*), Ginger (*Zingiber officinale*), Torch Ginger (*Etlingera elatior*), Golpar (*Heracleum persicum*), Grains of paradise (*Aframomum melegueta*), Grains of Selim, Kani pepper (*Xylopia aethiopica*), Horseradish (*Armoracia rusticana*), Houttuynia cordata, Huacatay, Mexican marigold, Mint marigold (*Tagetes minuta*), Hyssop (*Hyssopus officinalis*), Indonesian bay leaf, Daun salam (*Syzygium polyanthum*), Jasmine flowers (*Jasminum* spp.), Jimbu (*Allium hypsistum*), Juniper berry (*Juniperus communis*), Kaffir lime leaves (*Citrus hystrix*), Kala zeera (or kala jira), Black cumin (*Bunium persicum*), Kawakawa seeds (*Macropiper excelsum*), Kencur (*Kaempferia galanga*), Keluak (*Pangium edule*), Vietnamese balm (*Elsholtzia ciliata*), Kokam seed (*Garcinia indica*), Korarima, Ethiopian cardamom (*Aframomum corrorima*), Koseret leaves (*Lippia adoensis*), Lavender (*Lavandula* spp.), Lemon balm (*Melissa officinalis*), Lemongrass (*Cymbopogon*), Lemon ironbark (*Eucalyptus staigeriana*), Lemon myrtle (*Backhousia citriodora*), Lemon verbena (*Lippia citriodora*), Leptotes bicolor, Lesser calamint (*Calamintha nepeta*), nipitella, Licorice (*Glycyrrhiza glabra*), Lime flower (*Tilia* spp.), Lovage (*Levisticum officinale*), Mace (*Myristica fragrans*), St. Lucie cherry (*Prunus mahaleb*), Marjoram (*Origanum majorana*), Marsh mallow (*Althaea officinalis*), Mastic (*Pistacia lentiscus*), Mint (*Mentha* spp.), Mountain horopito (*Pseudowintera colorata*), Musk mallow, abelmosk (*Abelmoschus moschatus*), Nasturtium (*Tropaeolum majus*), Nigella (*Nigella sativa*), Njangsa (*Ricinodendron heudelotii*), Nutmeg (*Myristica fragrans*), Neem, Olida (*Eucalyptus olida*), Oregano (*Origanum*), Orris root (*Iris*), Pandan flower, kewra (*Pandanus odoratissimus*), Pandan leaf (*Pandanus amaryllifolius*), Paprika (*Capsicum annuum*), Paracress (*Spilanthes acmella, Soleracea*), Parsley (*Petroselinum crispum*), Black pepper, White pepper or Green pepper (*Piper nigrum*), Dorrigo pepper (*Tasmannia stipitata*), Long pepper (*Piper longum*) Mountain pepper (*Tasmannia lanceolata*), Peppermint (*Mentha piperata*), Peppermint gum leaf (*Eucalyptus dives*), Perilla (*Perilla* spp.), Peruvian pepper (*Schinus molle*), Pandanus amaryllifolius, Brazilian pepper (*Schinus terebinthifolius*), Quassia (*Quassia amara*), Ramsons (*Allium ursinum*), Rice paddy herb (*Limnophila aromatica*), Rosemary (*Rosmarinus officinalis*), Rue (*Ruta graveolens*), Safflower (*Carthamus tinctorius*), Saffron (*Crocus sativus*), Sage (*Salvia officinalis*), Saigon cinnamon (*Cinnamomum loureiroi*), Salad burnet (*Sanguisorba minor*), Salep (*Orchis mascula*), Sassafras (*Sassafras albidum*), Summer savory (*Satureja hortensis*), Winter savory (*Satureja montana*), Shiso (*Perilla frutescens*), Sorrel (*Rumex acetosa*), Sheep sorrel (*Rumex acetosella*), Spearmint (*Mentha spicata*), Spikenard (*Nardostachys grandiflora* or *N. jatamansi*), Star anise (*Illicium verum*), Sumac (*Rhus coriaria*), Sweet woodruff (*Galium odoratum*), Szechuan pepper (*Zanthoxylum piperitum*), Tarragon (*Artemisia dracunculus*), Thyme (*Thymus vulgaris*), Lemon thyme (*Thymus×citriodorus*), Turmeric (*Curcuma longa*), Vanilla (*Vanilla planifolia*), Vietnamese cinnamon (*Cinnamomum loureiroi*), Vietnamese coriander (*Persicaria odorata*), Voatsiperifery (*Piper borbonense*), Wasabi (*Wasabia japonica*), Water-pepper (*Polygonum hydropiper*), Watercress (*Rorippa nasturtium-aquatica*), Wattleseed (*Acacia*), Wild betel (*Piper sarmentosum*), Wild thyme (*Thymus serpyllum*), Willow herb (*Epilobium parviflorum*), Wintergreen (*Gaultheria procumbens*), Wood avens (*Geum urbanum*), Woodruff (*Galium odoratum*), absinthe (*Artemisia absinthium*), or Yerba buena.

The leaves, stems, stalks, shoots, seeds, roots, and/or fruit of an agricultural crop may be treated according to the methods of the present invention. The agricultural crop can be subsequently prepared for display or consumption, either by cutting, slicing, peeling, deseeding, dehusking, or other methods known in the art.

Improved Properties

Treatment of an agricultural crop according to the methods of the present invention imparts an improved property to the agricultural crop, e.g., prior to harvest or post-harvest.

The improved property can be one or more improvements including, but not limited to, reducing or preventing oxidative browning, dehydration, desiccation, bacterial, fungal, microbial, animal, or insect pest infestation, senescence, early ripening, and softening. The one or more improved properties can also be physical improvements including prevention of bruising, resistance to crushing, prevention or enhancement of clustering, and aggregation or association.

The improved property can also be one or more improvements including, but not limited to, appearance, e.g., enhanced color or artificial coloration. The one or more improved properties can also be resistance to adverse environmental factors, e.g., sun or UV damage. The improved property can also be improved taste, e.g., by carbohydrate, salt or food additive functionalization.

In one aspect, the improved property is reducing or preventing oxidative browning. In another aspect, the improved property is reducing or preventing dehydration. In another aspect, the improved property is reducing or preventing desiccation. In another aspect, the improved property is reducing or preventing bacterial pest infestation. In another aspect, the improved property is reducing or preventing fungal pest infestation. In another aspect, the improved property is reducing or preventing microbial pest infestation. In another aspect, the improved property is reducing or preventing animal pest infestation. In another aspect, the improved property is reducing or preventing insect pest infestation. In another aspect, the improved property is reducing or preventing senescence. In another aspect, the improved property is reducing or preventing early ripening. In another aspect, the improved property is reducing or preventing softening. In another aspect, the improved property is prevention of bruising, resistance to crushing, prevention or enhancement of clustering, and aggregation or association. In another aspect, the improved property is resistance to crushing. In another aspect, the improved property is prevention or enhancement of clustering. In another aspect, the improved property is aggregation or association. In another aspect, the improved property is improved appearance. In another aspect, the improved property is resistance to adverse environmental factors. In another aspect, the improved property is improved taste.

In one aspect, the improved property protects an agricultural crop prior to harvest. In another aspect, the improved property extends the transportation time to market. In another aspect, the improved property extends the shelf-life of an agricultural crop. In another aspect, the improved property increases nutritional value of an agricultural crop for longer periods.

Polymeric Xyloglucan

In the methods of the present invention, the polymeric xyloglucan can be any xyloglucan. In one aspect, the polymeric xyloglucan is obtained from natural sources. In another aspect, the polymeric xyloglucan is synthesized from component carbohydrates, UDP- or GDP-carbohydrates, or halogenated carbohydrates by any means used by those skilled in the art. In another aspect, the natural source of polymeric xyloglucan is tamarind seed or tamarind kernel powder, nasturtium, or plants of the genus *Tropaeolum*, particularly *Tropaeolum majus*. The natural source of polymeric xyloglucan may be seeds of various dicotyledonous plants such as *Hymenaea courbaril*, Leguminosae-Caesalpinioideae including the genera *Cynometreae, Amherstieae*, and *Sclerolobieae*. The natural source of polymeric xyloglucan may also be the seeds of plants of the families Primulales, Annonaceae, Limnanthaceae, Melianthaceae, Pedaliaceae, and Tropaeolaceae or subfamily Thunbergioideae. The natural source of polymeric xyloglucan may also be the seeds of plants of the families Balsaminaceae, Acanthaceae, Linaceae, Ranunculaceae, Sapindaceae, and Sapotaceae or non-endospermic members of family Leguminosae subfamily Faboideae. In another aspect, the natural source of polymeric xyloglucan is the primary cell walls of dicotyledonous plants. In another aspect, the natural source of polymeric xyloglucan may be the primary cell walls of nongraminaceous, monocotyledonous plants.

The natural source polymeric xyloglucan may be extracted by extensive boiling or hot water extraction, or by other methods known to those skilled in the art. In one aspect, the polymeric xyloglucan may be subsequently purified, for example, by precipitation in 80% ethanol. In another aspect, the polymeric xyloglucan is a crude or enriched preparation, for example, tamarind kernel powder. In another aspect, the synthetic xyloglucan may be generated by automated carbohydrate synthesis (Seeberger, *Chem. Commun*, 2003, 1115-1121), or by means of enzymatic polymerization, for example, using a glycosynthase (Spaduit et al., 2011, *J. Am. Chem. Soc.* 133: 10892-10900).

In one aspect, the average molecular weight of the polymeric xyloglucan ranges from about 2 kDa to about 500 kDa, e.g., about 2 kDa to about 400 kDa, about 3 kDa to about 300 kDa, about 3 kDa to about 200 kDa, about 5 kDa to about 100 kDa, about 5 kDa to about 75 kDa, about 7.5 kDa to about 50 kDa, or about 10 kDa to about 30 kDa. In another aspect, the number of repeating units is about 2 to about 500, e.g., about 2 to about 400, about 3 to about 300, about 3 to about 200, about 5 to about 100, about 7.5 to about 50, or about 10 to about 30. In another aspect, the repeating unit is any combination of G, X, L, F, S, T and J subunits, according to the nomenclature of Fry et al. (*Physiologia Plantarum*, 89: 1-3, 1993). In another aspect, the repeating unit is either fucosylated or non-fucosylated XXXG-type polymeric xyloglucan common to dicotyledons and nongraminaceous monocots. In another aspect, the polymeric xyloglucan is O-acetylated. In another aspect the polymeric xyloglucan is not O-acetylated. In another aspect, side chains of the polymeric xyloglucan may contain terminal fucosyl residues. In another aspect, side chains of the polymeric xyloglucan may contain terminal arabinosyl residues. In another aspect, side chains of the polymeric xyloglucan may contain terminal xylosyl residues.

For purposes of the present invention, references to the term xyloglucan herein refer to polymeric xyloglucan.

Xyloglucan Oligomer

In the methods of the present invention, the xyloglucan oligomer can be any xyloglucan oligomer. The xyloglucan oligomer may be obtained by degradation or hydrolysis of polymeric xyloglucan from any source. The xyloglucan oligomer may be obtained by enzymatic degradation of polymeric xyloglucan, e.g., by quantitative or partial digestion with a xyloglucanase or endoglucanase (endo-$\beta$-1-4-glucanase). The xyloglucan oligomer may be synthesized from component carbohydrates, UDP- or GDP-carbohydrates, or halogenated carbohydrates by any of the manners commonly used by those skilled in the art.

In one aspect, the average molecular weight of the xyloglucan oligomer ranges from 0.5 kDa to about 500 kDa, e.g., about 1 kDa to about 20 kDa, about 1 kDa to about 10 kDa, or about 1 kDa to about 3 kDa. In another aspect, the number of repeating units is about 1 to about 500, e.g., about 1 to about 20, about 1 to about 10, or about 1 to about 3. In the methods of the present invention, the xyloglucan oligomer is optimally as short as possible (i.e., 1 repeating unit, or about 1 kDa in molecular weight) to maximize the solubility and solution molarity per gram of dissolved xyloglucan oligomer, while maintaining substrate specificity for xyloglucan endotransglycosylase activity. In another aspect, the xyloglucan oligomer comprises any combination of G ($\beta$-D glucopyranosyl-), X ($\alpha$-D-xylopyranosyl-(1→6)-$\beta$-D-glucopyranosyl-), L ($\beta$-D-galactopyranosyl-(1→2)-$\alpha$-D-xylopyranosyl-(1→6)-$\beta$-D-glucopyranosyl-), F ($\alpha$-L-fucopyranosyl-(1→2)-β-D-galactopyranosyl-(1→2)-α-D-xylopyranosyl-(1-6)-β-D-glucopyranosyl-), S (α-L-arabinofurosyl-(1→2)-α-D-xylopyranosyl-(1→6)-β-D-glucopyranosyl-), T (α-L-arabino-furosyl-(1→3)-α-L-arabinofurosyl-(1→2)-α-D-xylopyranosyl-(1→6)-β-D-glucopyranosyl-), and J (α-L-galactopyranosyl-(1→2)-β-D-galactopyranosyl-(1→2)-α-D-xylopyranosyl-(1→6)-β-D-gluco-pyranosyl-) subunits according to the nomenclature of Fry et al. (*Physiologia Plantarum* 89: 1-3, 1993). In another aspect, the xyloglucan oligomer is the XXXG heptasaccharide common to dicotyledons and nongraminaceous monocots. In another aspect, the xyloglucan oligomer is O-acetylated. In another aspect, the xyloglucan oligomer is not O-acetylated. In another aspect, side chains of the xyloglucan oligomer may contain terminal fucosyl residues. In another aspect, side chains of the xyloglucan oligomer may contain terminal arabinosyl residues. In another aspect, side chains of the xyloglucan oligomer may contain terminal xylosyl residues.

Functionalization of Xyloglucan Oligomer and Polymeric Xyloglucan

The xyloglucan oligomer can be functionalized by incorporating any chemical group known to those skilled in the art. The chemical group may be a compound of interest or a reactive group such as an aldehyde group, an amino group, an aromatic group, a carboxyl group, a halogen group, a hydroxyl group, a ketone group, a nitrile group, a nitro group, a sulfhydryl group, or a sulfonate group.

In one aspect, the chemical group is an aldehyde group.

In another aspect, the chemical group is an amino group. The amino group can be incorporated into polymeric xyloglucan by reductive amination. Alternatively, the amino group can be an aliphatic amine or an aromatic amine (e.g., aniline). The aliphatic amine can be a primary, secondary or tertiary amine. Primary, secondary, and tertiary amines are nitrogens bound to one, two and three carbons, respectively. In one aspect, the primary amine is $C_1$-$C_8$, e.g., ethylamine. In another aspect, each carbon in the secondary amine is $C_1$-$C_8$, e.g., diethylamine. In another aspect, each carbon in the tertiary amine is $C_1$-$C_8$, e.g., triethylamine.

In another aspect, the chemical group is an aromatic group. The aromatic group can be an arene group, an aryl halide group, a phenolic group, a phenylamine group, a diazonium group, or a heterocyclic group.

In another aspect, the chemical group is a carboxyl group. The carboxyl group can be an acyl halide, an amide, a carboxylic acid, an ester, or a thioester.

In another aspect, the chemical group is a halogen group. The halogen group can be fluorine, chlorine, bromine, or iodine.

In another aspect, the chemical group is a hydroxyl group.

In another aspect, the chemical group is a ketone group.

In another aspect, the chemical group is a nitrile group.

In another aspect, the chemical group is a nitro group.

In another aspect, the chemical group is a sulfhydryl group.

In another aspect, the chemical group is a sulfonate group.

The chemical reactive group can itself be the chemical group that imparts a desired physical or chemical property to an agricultural crop.

By incorporation of chemical reactive groups in such a manner, one skilled in the art can further derivatize the incorporated reactive groups with compounds (e.g., macromolecules) that will impart a desired physical or chemical property to an agricultural crop. For example, the incorporated chemical group may react with the compound that imparts the desired property to incorporate that group into the xyloglucan oligomer via a covalent bond. Alternatively, the chemical group may bind to the compound that imparts the desired property in either a reversible or irreversible manner, and incorporate the compound via a non-covalent association. The derivatization can be performed directly on the functionalized xyloglucan oligomer or after the functionalized xyloglucan oligomer is incorporated into polymeric xyloglucan.

Alternatively, the xyloglucan oligomer can be functionalized by incorporating directly a compound that imparts a desired physical or chemical property to a material by using a reactive group contained in the compound or a reactive group incorporated into the compound, such as any of the groups described above.

On the other hand, the polymeric xyloglucan can be directly functionalized by incorporating a reactive chemical group as described above. By incorporation of reactive chemical groups directly into polymeric xyloglucan, one of skill in the art can further derivatize the incorporated reactive groups with compounds that will impart a desired physical or chemical property to a material. By incorporation of a compound directly into the polymeric xyloglucan, a desired physical or chemical property can also be directly imparted to a material.

In one aspect, the functionalization is performed by reacting the reducing end hydroxyl of the xyloglucan oligomer or the polymeric xyloglucan. In another aspect, a non-reducing hydroxyl group, other than the non-reducing hydroxyl at position 4 of the terminal glucose, can be reacted. In another aspect, the reducing end hydroxyl and a non-reducing hydroxyl, other than the non-reducing hydroxyl at position 4 of the terminal glucose, can be reacted.

The chemical functional group can be added by enzymatic modification of the xyloglucan oligomer or polymeric xyloglucan, or by a non-enzymatic chemical reaction. In one aspect, enzymatic modification is used to add the chemical functional group. In one embodiment of enzymatic modification, the enzymatic functionalization is oxidation to a ketone or carboxylate, e.g., by galactose oxidase. In another embodiment of enzymatic modification, the enzymatic functionalization is oxidation to a ketone or carboxylate by AA9 Family oxidases (formerly glycohydrolase Family 61 enzymes).

In another aspect, the chemical functional group is added by a non-enzymatic chemical reaction. In one embodiment of the non-enzymatic chemical reaction, the reaction is incorporation of a reactive amine group by reductive amination of the reducing end of the carbohydrate as described by Roy et al., 1984, *Can. J. Chem.* 62: 270-275, or Dalpathado et al., 2005, *Anal. Bioanal. Chem.* 381: 1130-1137. In another embodiment of non-enzymatic chemical reaction, the reaction is incorporation of a reactive ketone group by oxidation of the reducing end hydroxyl to a ketone, e.g., by copper (II). In another embodiment of non-enzymatic chemical reaction, the reaction is oxidation of non-reducing end hydroxyl groups (e.g., of the non-glycosidic bonded position 6 hydroxyls of glucose or galactose) by (2,2,6,6-tetramethyl-piperidin-1-yl)oxyl (TEMPO), or the oxoammonium salt thereof, to generate an aldehyde or carboxylic acid as described in Bragd et al., 2002, *Carbohydrate Polymers* 49: 397-406, or Breton et al., 2007, *Eur. J. Org. Chem.* 10: 1567-1570.

Xyloglucan oligomers or polymeric xyloglucan can be functionalized by a chemical reaction with a compound containing more than one (i.e. bifunctional or multifunctional) chemical functional group comprising at least one chemical functional group that is directly reactive with xyloglucan oligomer or polymeric xyloglucan. In one aspect, the bifunctional chemical group is a hydrocarbon containing a primary amine and a second chemical functional group. The second functional group can be any of the other groups described above. In some aspects, the two functional groups are separated by hydrocarbon chains (linkers) of various lengths as is well known in the art.

Xyloglucan oligomers or polymeric xyloglucan can be functionalized with a compound of interest by step-wise or concerted reaction wherein the xyloglucan oligomer or polymeric xyloglucan is functionalized as described above, and the compound is reactive to the functionalization introduced therein. In one aspect of coupling via a functionalized xyloglucan oligomer, an amino group is first incorporated into the xyloglucan oligomer by reductive amination and a reactive carbonyl is secondarily coupled to the introduced amino group. In another aspect of coupling via an amino-modified xyloglucan oligomer, the second coupling step incorporates a chemical group, compound or macromolecule via coupling an N-hydroxysuccinimidyl (NHS) ester or imidoester to the introduced amino group. In a preferred embodiment, the NHS ester secondarily coupled to the introduced amino group is a component of a mono or bi-functional crosslink reagent. In another aspect of coupling to a functionalized xyloglucan or xyloglucan oligomer, the first reaction step comprises functionalization with a sulfhydryl group, either via reductive amination with an alkylthioamine ($NH_2$—$(CH_2)_n$—SH) at elevated temperatures in the presence of a reducing agent (Magid et al., 1996, *J. Org. Chem.* 61: 3849-3862), or via radical coupling (Wang et al., 2009, *Arkivoc* xiv: 171-180), followed by reaction of a maleimide group to the sulfhydryl. In some aspects, the reactive group in the compound that imparts the desired property is separated from the rest of the compound by a hydrocarbon chain of an appropriate length, as is well described in the art.

Non-limiting examples of compounds of interest that can be used to functionalize polymeric xyloglucan or xyloglucan oligomers, either by direct reaction or via reaction with a xyloglucan-reactive compound, include peptides, polypeptides, proteins, hydrophobic groups, hydrophilic groups, flame retardants, dyes, color modifiers, specific affinity tags, non-specific affinity tags, metals, metal oxides, metal sulfides, minerals, fungicides, herbicides, microbicides or microbiostatics, and non-covalent linker molecules.

In one aspect, the compound is a peptide. The peptide can be an antimicrobial peptide, a "self-peptide" designed to reduce allergenicity and immunogenicity, a cyclic peptide, glutathione, or a signaling peptide (such as a tachykinin peptide, vasoactive intestinal peptide, pancreatic polypeptide related peptide, calcitonin peptide, lipopeptide, cyclic lipopeptide, or other peptide).

In another aspect, the compound is a polypeptide. The polypeptide can be a non-catalytically active protein (i.e., structural or binding protein), or a catalytically active protein (i.e., enzyme). The polypeptide can be an enzyme, an antibody, or an abzyme.

In another aspect, the compound is a compound comprising a hydrophobic group.

The hydrophobic group can be polyurethane, polytetrafluoroethylene, or polyvinylidene fluoride.

In another aspect, the compound is a compound comprising a hydrophilic group. The hydrophilic group can be methacylate, methacrylamide, or polyacrylate.

In another aspect, the compound is a flame retardant. The flame-retardant can be aluminum hydroxide or magnesium hydroxide. The flame-retardant can also be a compound comprising an organohalogen group or an organophosphorous group.

In another aspect, the compound is a dye or pigment.

In another aspect, the compound is a specific affinity tag. The specific affinity tag can be biotin, avidin, a chelating group, a crown ether, a heme group, a non-reactive substrate analog, an antibody, target antigen, or a lectin.

In another aspect, the compound is a non-specific affinity tag. The non-specific affinity tag can be a polycation group, a polyanion group, a magnetic particle (e.g., magnetite), a hydrophobic group, an aliphatic group, a metal, a metal oxide, a metal sulfide, or a molecular sieve.

In another aspect, the compound is a fungicide. The fungicide can be a compound comprising a dicarboximide group (such as vinclozolin), a phenylpyrrole group (such as fludioxonil), a chlorophenyl group (such as quintozene), a chloronitrobenzene (such as dicloran), a triadiazole group (such as etridiazole), a dithiocarbamate group (such as mancozeb or dimethyldithiocarbamate), or an inorganic molecule (such as copper or sulfur). In another aspect, the fungicide is a bacterium or bacterial spore such as *Bacillus* or a *Bacillus* spore.

In another aspect, the compound is a herbicide. The herbicide can be glyphosate, a synthetic plant hormone (such as a compound comprising a 2,4-dichlorophenoxyacetic acid group, a 2,4,5-trichlorophenoxyacetic acid group, a 2-methyl-4-chlorophenoxyacetic acid group, a 2-(2-methyl-4-chlorophenoxy)propionic acid group, a 2-(2,4-dichlorophenoxy)propionic acid group, or a (2,4-dichlorophenoxy)butyric acid group), or a compound comprising a triazine group (such as atrazine (2-chloro-4-(ethylamino)-6-isopropylamino)-s-triazine).

In another aspect, the compound is a bactericidal or bacteriostatic compound. The bactericidal or bacteriostatic compound can be a copper or copper alloy (such as brass, bronze, cupronickel, or copper-nickel-zinc alloy), a sulfonamide group (such as sulfamethoxazole, sulfisomidine, sulfacetamide or sulfadiazine), a silver or organo-silver group, $TiO_2$, $ZnO_2$, an antimicrobial peptide, or chitosan.

In another aspect, the compound is a UV resistant compound. The UV resistant compound can be zinc or $ZnO_2$, kaolin, aluminum, aluminum oxides, or other UV-resistant compounds.

In another aspect, the compound is an anti-oxidant compound. The anti-oxidant compound can be ascorbate, manganese, iodide, retinol, a terpenoid, tocopherol, a flavonoid or other anti-oxidant phenolic or polyphenolic or other anti-oxidant compounds.

In another aspect, the compound is a non-covalent linker molecule.

In another aspect, the compound is a color modifier. The color modifier can be a dye, fluorescent brightener, color modifier, or mordant (e.g., alum, chrome alum).

Preparation of Modified Agricultural Crops

In the methods of the present invention, a modified agricultural crop can be prepared by treating the agricultural crop with (a) a composition comprising a xyloglucan endotransglycosylase, a polymeric xyloglucan, and a functionalized xyloglucan oligomer comprising a chemical group; (b) a composition comprising a xyloglucan endotransglycosylase, a polymeric xyloglucan functionalized with a chemical group, and a functionalized xyloglucan oligomer comprising a chemical group; (c) a composition comprising a xyloglucan endotransglycosylase, a polymeric xyloglucan functionalized with a chemical group, and a xyloglucan oligomer; (d) a composition comprising a xyloglucan endotransglycosylase, a polymeric xyloglucan, and a xyloglucan oligomer; (e) a composition comprising a xyloglucan endotransglycosylase and a polymeric xyloglucan functionalized with a chemical group; (f) a composition comprising a xyloglucan endotransglycosylase and a polymeric xyloglucan; (g) a composition comprising a xyloglucan endotransglycosylase and a functionalized xyloglucan oligomer comprising a chemical group; (h) a composition comprising a xyloglucan endotransglycosylase and a xyloglucan oligomer, or (i) a composition of (a), (b), (c), (d), (e), (f), (g), or (h) without a xyloglucan endotransglycosylase, in a medium under conditions leading to a modified agricultural crop, wherein the modified agricultural crop possesses an improved property compared to the unmodified agricultural crop.

The methods are exemplified by, but are not limited to, improved resistance to browning of apple and potato slices by treating these agricultural crops, post harvest, with a solution comprising xyloglucan and xyloglucan endotransglycosylase. The xyloglucan can be any xyloglucan, for example, tamarind kernel xyloglucan. The xyloglucan endotransglycosylase can be, for example, *Vigna angularis* XET16 or *Arabidopsis thaliana* XET14. In the methods of the present invention, slices of fruit or vegetable (e.g., apple or potato) can be dipped in a pH-controlled solution (e.g., a buffered solution such as sodium citrate) containing xyloglucan and xyloglucan endotransglycosylase. The pH of the buffered solution can be between about 3 and about 9, e.g., about 4 to about 8 or about 5 to about 7. The concentration of sodium citrate can be about 1 mM to about 1 M, e.g., about 5 mM to about 500 mM, about 10 mM to about 100 mM, or about 20 mM to about 50 mM. The concentration of xyloglucan can be about 10 mg/L to about 100 g/L, e.g., about 100 mg/L to about 10 g/L, about 500 mg/L to about 5 g/L, or about 1 g/L to about 2 g/L. The concentration of xyloglucan endotransglycosylase can be about 1 nM to about 1 mM, e.g. about 10 nM to about 100 μM, about 100 nM to about 10 μM, or about 500 nM to about 1.5 μM. The time length of the dip can be instantaneous to about 12 hours, e.g., about 1 second to about 3 hours, about 10 seconds to about 30 minutes, or about 30 seconds to about 2 minutes. The time length of the dip can be optimized to maximize the improved property, or can be optimized to the method by one skilled in the art. The excess solution can be removed, for instance, by washing in water, by dipping in a pH-controlled solution not containing xyloglucan, xyloglucan endotransglycosylase, or both, or by touching the slice of apple or potato to the side of the container or to a paper towel or wipe. Alternatively, the excess solution can be left on the agricultural crop or left on the crop for an appropriate length of time prior to washing. In the current example, the excess solution is removed by touching the fruit or vegetable to the side of the container. In one aspect, the xyloglucan and xyloglucan endotransglycosylase can be separated into 2 solutions and the agricultural crop dipped into each independently and sequentially. In another aspect, xyloglucan oligomers or functionalized xyloglucan oligomers are added to the solution of xyloglucan and xyloglucan endotransglycosylase, or to one or the other or both solutions if the two components are separated into 2 solutions. For example, xyloglucan oligomers can be added to a solution of xyloglucan and xyloglucan endotransglycosylase at a molar ratio to xyloglucan of about $10^{-4}$ to about 100, e.g., about $10^{-3}$ to about 10 or about $10^{-2}$ to about 1. In this manner, one of skill in the art can use the transglycosylase activity of xyloglucan endotransglycosylase to optimize the size of the xyloglucan polymer and/or the degree of functionalization of the xyloglucan to affect the optimal improved property.

Sources of Xyloglucan Endotransglycosylases

Any xyloglucan endotransglycosylase that possesses suitable enzyme activity at a pH and temperature appropriate for the methods of the present invention may be used. It is preferable that the xyloglucan endotransglycosylase is active over a broad pH and temperature range. In an embodiment, the xyloglucan endotransglycosylase has a pH optimum in the range of about 3 to about 10. In another embodiment, the xyloglucan endotransglycosylase has a pH optimum in the range of about 4.5 to about 8.5. In another embodiment, the xyloglucan endotransglycosylase has a cold denaturation temperature less than or equal to about 5° C. or a melting temperature of about 100° C. or higher. In another embodiment, the xyloglucan endotransglycosylase has a cold denaturation temperature of less than or equal to 20° C. or a melting temperature greater than or equal to about 75° C.

The source of the xyloglucan endotransglycosylase used is not critical in the present invention. Accordingly, the xyloglucan endotransglycosylase may be obtained from any source such as a plant, microorganism, or animal.

In one embodiment, the xyloglucan endotransglycosylase is obtained from a plant source. Xyloglucan endotransglycosylase can be obtained from cotyledons of the family Fabaceae (synonyms: Leguminosae and Papilionaceae), preferably genus *Phaseolus*, in particular, *Phaseolus aureus*. Preferred monocotyledons are non-graminaceous monocotyledons and liliaceous monocotyledons. Xyloglucan endotransglycosylase can also be extracted from moss and liverwort, as described in Fry et al., 1992, *Biochem. J.* 282: 821-828. For example, the xyloglucan endotransglycosylase may be obtained from cotyledons, i.e., a dicotyledon or a monocotyledon, in particular a dicotyledon selected from the group consisting of azuki beans, canola, cauliflowers, cotton, poplar or hybrid aspen, potatoes, rapes, soy beans, sunflowers, thalecress, tobacco, and tomatoes, or a monocotyledon selected from the group consisting of wheat, rice, corn, and sugar cane. See, for example, WO 2003/033813 and WO 97/23683.

In another embodiment, the xyloglucan endotransglycosylase is obtained from *Arabidopsis thaliana* (GENESEQP: AOE11231, GENESEQP:AOE93420, GENESEQP: BAL03414, GENESEQP:BAL03622, or GENESEQP: AWK95154); *Carica papaya* (GENESEQP:AZR75725); *Cucumis sativus* (GENESEQP:AZV66490); *Daucus carota* (GENESEQP:AZV66139); *Festuca pratensis* (GENESEQP:AZR80321); *Glycine max* (GENESEQP:AWK95154 or GENESEQP:AYF92062); *Hordeum vulgare* (GENESEQP: AZR85056, GENESEQP:AQY12558, GENESEQP: AQY12559, or GENESEQP:AWK95180); *Lycopersicon esculentum* (GENESEQP:ATZ45232); *Medicago truncatula* (GENESEQP:ATZ48025); *Oryza sativa* (GENESEQP: ATZ42485, GENESEQP:ATZ57524, or GENESEQP: AZR76430); *Populus tremula* (GENESEQP:AWK95036); *Sagittaria pygmaea* (GENESEQP:AZV66468); *Sorghum bicolor* (GENESEQP:BAO79623 or GENESEQP: BAO79007); *Vigna angularis* (GENESEQP:ATZ61320); or *Zea mays* (GENESEQP:AWK94916).

In another embodiment, the xyloglucan endotransglycosylase is a xyloglucan endotransglucosylase/hydrolase (XTH) with both hydrolytic and transglycosylating activities. In a preferred embodiment, the ratio of transglycosylation to hydrolytic rates is at least $10^{-2}$ to $10^7$, e.g., $10^{-1}$ to $10^6$ or 10 to 1000.

Production of Xyloglucan Endotransglycosylases

Xyloglucan endotransglycosylase may be extracted from plants. Suitable methods for extracting xyloglucan endotransglycosylase from plants are described Fry et al., 1992, Biochem. J. 282: 821-828; Sulova et al., 1998, Biochem. J. 330: 1475-1480; Sulova et al., 1995, Anal. Biochem. 229: 80-85; WO 95/13384; WO 97/23683; or EP 562 836.

Xyloglucan endotransglycosylase may also be produced by cultivation of a transformed host organism containing the appropriate genetic information from a plant, microorganism, or animal. Transformants can be prepared and cultivated by methods known in the art.

Techniques used to isolate or clone a gene are known in the art and include isolation from genomic DNA or cDNA, or a combination thereof. The cloning of the gene from genomic DNA can be effected, e.g., by using the polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used.

A nucleic acid construct can be constructed to comprise a gene encoding a xyloglucan endotransglycosylase operably linked to one or more control sequences that direct the expression of the coding sequence in a suitable host cell under conditions compatible with the control sequences. The gene may be manipulated in a variety of ways to provide for expression of the xyloglucan endotransglycosylase. Manipulation of the gene prior to its insertion into a vector may be desirable or necessary depending on the expression vector. Techniques for modifying polynucleotides utilizing recombinant DNA methods are well known in the art.

The control sequence may be a promoter, a polynucleotide that is recognized by a host cell for expression of a polynucleotide encoding a xyloglucan endotransglycosylase. The promoter contains transcriptional control sequences that mediate the expression of the xyloglucan endotransglycosylase. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs in a bacterial host cell are the promoters obtained from the Bacillus amyloliquefaciens alpha-amylase gene (amyQ), Bacillus licheniformis alpha-amylase gene (amyL), Bacillus licheniformis penicillinase gene (penP), Bacillus stearothermophilus maltogenic amylase gene (amyM), Bacillus subtilis levansucrase gene (sacB), Bacillus subtilis xylA and xylB genes, Bacillus thuringiensis cryIIA gene (Agaisse and Lereclus, 1994, Molecular Microbiology 13: 97-107), E. coli lac operon, E. coli trc promoter (Egon et al., 1988, Gene 69: 301-315), Streptomyces coelicolor agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs in a filamentous fungal host cell are promoters obtained from the genes for Aspergillus nidulans acetamidase, Aspergillus niger neutral alpha-amylase, Aspergillus niger acid stable alpha-amylase, Aspergillus niger or Aspergillus awamori glucoamylase (glaA), Aspergillus oryzae TAKA amylase, Aspergillus oryzae alkaline protease, Aspergillus oryzae triose phosphate isomerase, Fusarium oxysporum trypsin-like protease (WO 96/00787), Fusarium venenatum amyloglucosidase (WO 00/56900), Fusarium venenatum Daria (WO 00/56900), Fusarium venenatum Quinn (WO 00/56900), Rhizomucor miehei lipase, Rhizomucor miehei aspartic proteinase, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor, as well as the NA2-tpi promoter (a modified promoter from an Aspergillus neutral alpha-amylase gene in which the untranslated leader has been replaced by an untranslated leader from an Aspergillus triose phosphate isomerase gene; non-limiting examples include modified promoters from an Aspergillus niger neutral alpha-amylase gene in which the untranslated leader has been replaced by an untranslated leader from an Aspergillus nidulans or Aspergillus oryzae triose phosphate isomerase gene); and mutant, truncated, and hybrid promoters thereof. Other promoters are described in U.S. Pat. No. 6,011,147.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the xyloglucan endotransglycosylase. Any terminator that is functional in the host cell may be used in the present invention.

Preferred terminators for bacterial host cells are obtained from the genes for Bacillus clausii alkaline protease (aprH), Bacillus licheniformis alpha-amylase (amyL), and Escherichia coli ribosomal RNA (rrnB).

Preferred terminators for filamentous fungal host cells are obtained from the genes for Aspergillus nidulans acetamidase, Aspergillus nidulans anthranilate synthase, Aspergillus niger glucoamylase, Aspergillus niger alpha-glucosidase, Aspergillus oryzae TAKA amylase, Fusarium oxysporum trypsin-like protease, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the xyloglucan endotransglycosylase. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a xyloglucan endotransglycosylase and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a xyloglucan endotransglycosylase. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a xyloglucan endotransglycosylase and the signal peptide sequence is positioned next to the N-terminus of the propeptide sequence.

The various nucleotide and control sequences may be joined together to produce a recombinant expression vector that may include one or more convenient restriction sites to allow for insertion or substitution of the polynucleotide encoding the xyloglucan endotransglycosylase at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated.

Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the xyloglucan endotransglycosylase or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of a xyloglucan endotransglycosylase. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

The host cell may be any cell useful in the recombinant production of a xyloglucan endotransglycosylase, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Strepto-*

*coccus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp. 182-187, Academic Press, Inc., New York; Ito et al., 1983, *J. Bacteriol.* 153: 163; and Hinnen et al., 1978, *Proc. Natl. Acad. Sci. USA* 75: 1920.

The host cells are cultivated in a nutrient medium suitable for production of the xyloglucan endotransglycosylase using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the xyloglucan endotransglycosylase to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the xyloglucan endotransglycosylase is secreted into the nutrient medium, the polypeptide can be recovered directly from the medium. If the xyloglucan endotransglycosylase is not secreted, it can be recovered from cell lysates.

The xyloglucan endotransglycosylase may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The xyloglucan endotransglycosylase may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising the polypeptide is recovered. In a preferred aspect, xyloglucan endotransglycosylase yield may be improved by subsequently washing cellular debris in buffer or in buffered detergent solution to extract biomass-associated polypeptide.

The xyloglucan endotransglycosylase may be purified by a variety of procedures known in the art including, but not limited to, chromatography (e.g., ion exchange, affinity, hydrophobic interaction, mixed mode, reverse phase, chromatofocusing, and size exclusion), electrophoretic procedures (e.g., preparative isoelectric focusing), differential solubility (e.g., ammonium sulfate precipitation), PAGE, membrane-filtration or extraction (see, e.g., *Protein Purification*, Janson and Ryden, editors, VCH Publishers, New York, 1989) to obtain substantially pure polypeptide. In a preferred aspect, xyloglucan endotransglycosylase may be purified by formation of a covalent acyl-enzyme intermediate with xyloglucan, followed by precipitation with microcrystalline cellulose or adsorption to cellulose membranes. Release of the polypeptide is then effected by addition of xyloglucan oligomers to resolve the covalent intermediate (Sulova and Farkas, 1999, *Protein Expression and Purification* 16(2): 231-235, and Steele and Fry, 1999, *Biochemical Journal* 340: 207-211).

The present invention is further described by the following examples that should not be construed as limiting the scope of the invention.

EXAMPLES

Media and Solutions

COVE agar plates were composed of 342.3 g of sucrose, 252.54 g of CsCl, 59.1 g of acetamide, 520 mg of KCl, 520 mg of $MgSO_4.7H_2O$, 1.52 g of $KH_2PO_4$, 0.04 mg of $Na_2B_4O_7.10H_2O$, 0.4 mg of $CuSO_4.5H_2O$, 1.2 mg of $FeSO_4.7H_2O$, 0.7 mg of $MnSO_4.2H_2O$, 0.8 mg of $Na_2MoO_4.2H_2O$, 10 mg of $ZnSO_4.7H_2O$, 25 g of Noble agar, and deionized water to 1 liter.

LB medium was composed of 10 g of tryptone, 5 g of yeast extract, 5 g of NaCl, and deionized water to 1 liter.

LB plates were composed of 10 g of tryptone, 5 g of yeast extract, 5 g of NaCl, 15 g of bacteriological agar, and deionized water to 1 liter.

Minimal medium agar plates were composed of 342.3 g of sucrose, 10 g of glucose, 4 g of $MgSO_4.7H_2O$, 6 g of $NaNO_3$, 0.52 g of KCl, 1.52 g of $KH_2PO_4$, 0.04 mg of $Na_2B_4O_7.10H_2O$, 0.4 mg of $CuSO_4.5H_2O$, 1.2 mg of $FeSO_4.7H_2O$, 0.7 mg of $MnSO_4.2H_2O$, 0.8 mg of $Na_2MoO_4.2H_2O$, 10 mg of $ZnSO_4.7H_2O$, 500 mg of citric acid, 4 mg of d-biotin, 20 g of Noble agar, and deionized water to 1 liter.

Synthetic defined medium lacking uridine was composed of 18 mg of adenine hemisulfate, 76 mg of alanine, 76 mg of arginine hydrochloride, 76 mg of asparagine monohydrate, 76 mg of aspartic acid, 76 mg of cysteine hydrochloride monohydrate, 76 mg of glutamic acid monosodium salt, 76 mg of glutamine, 76 mg of glycine, 76 mg of histidine, myo-76 mg of inositol, 76 mg of isoleucine, 380 mg of leucine, 76 mg of lysine monohydrochloride, 76 mg of methionine, 8 mg of p-aminobenzoic acid potassium salt, 76 mg of phenylalanine, 76 mg of proline, 76 mg of serine, 76 mg of threonine, 76 mg of tryptophan, 76 mg of tyrosine disodium salt, 76 mg of valine, and deionized water to 1 liter.

TAE buffer was composed of 4.84 g of Tris base, 1.14 ml of glacial acetic acid, 2 ml of 0.5 M EDTA pH 8.0, and deionized water to 1 liter.

TBE buffer was composed of 10.8 g of Tris base, 5.5 g of boric acid, 4 ml of 0.5 M EDTA pH 8.0, and deionized water to 1 liter.

2XYT plus ampicillin plates were composed of 16 g of tryptone, 10 g of yeast extract, 5 g of sodium chloride, 15 g of Bacto agar, and deionized water to 1 liter. One ml of a 100 mg/ml solution of ampicillin was added after the autoclaved medium was tempered to 55° C.

YP+2% glucose medium was composed of 10 g of yeast extract, 20 g of peptone, 20 g of glucose, and deionized water to 1 liter.

YP+2% maltodextrin medium was composed of 10 g of yeast extract, 20 g of peptone, 20 g of maltodextrin, and deionized water to 1 liter.

Example 1: Preparation of *Vigna angularis* Xyloglucan Endotransglycosylase 16

*Vigna angularis* xyloglucan endotransglycosylase 16 (VaXET16; SEQ ID NO: 1 [native DNA sequence], SEQ ID NO: 2 [synthetic DNA sequence], and SEQ ID NO: 3 [deduced amino acid sequence]; also referred to as XTH1) was recombinantly produced in *Aspergillus oryzae* MT3568 according to the protocol described below. *Aspergillus oryzae* MT3568 is an amdS (acetamidase) disrupted gene derivative of *Aspergillus oryzae* JaL355 (WO 2002/40694), in which pyrG auxotrophy was restored by disrupting the *A. oryzae* amdS gene with the pyrG gene.

The vector pDLHD0012 was constructed to express the VaXET16 gene in multi-copy in *Aspergillus oryzae*. Plasmid pDLHD0012 was generated by combining two DNA fragments using megaprimer cloning: Fragment 1 containing the VaXET16 ORF and flanking sequences with homology to vector pBM120 (US20090253171), and Fragment 2 consisting of an inverse PCR amplicon of vector pBM120.

Fragment 1 was amplified using primer 613788 (sense) and primer 613983 (antisense) shown below. These primers were designed to contain flanking regions of sequence homology to vector pBM120 (lower case) for ligation-free cloning between the PCR fragments.

```
Primer 613788 (sense):
                                       (SEQ ID NO: 7)
ttcctcaatcctctatatacacaactggccATGGGCTCGTCCCTCTGGAC Primer 613983 (antisense):
                                       (SEQ ID NO: 8)
tgtcagtcacctctagttaattaGATGTCCCTATCGCGTGTACACTCG
```

Fragment 1 was amplified by PCR in a reaction composed of 10 ng of a GENEART® vector μMA containing the VaXET16 synthetic gene (SEQ ID NO: 3 [synthetic DNA sequence]) cloned between the Sac I and Kpn I sites, 0.5 μl of PHUSION® DNA Polymerase (New England Biolabs, Inc., Ipswich, Mass., USA), 20 μmol of primer 613788, 20 μmol of primer 613983, 1 μl of 10 mM dNTPs, 10 μl of 5× PHUSION® HF buffer (New England Biolabs, Inc., Ipswich, Mass., USA), and 35.5 μl of water. The reaction was incubated in an EPPENDORF® MASTERCYCLER® (Eppendorf AG, Hamburg, Germany) programmed for 1 cycle at 98° C. for 30 seconds; and 30 cycles each at 98° C. for 10 seconds, 60° C. for 10 seconds, and 72° C. for 30 seconds. The resulting 0.9 kb PCR product (Fragment 1) was treated with 1 μl of Dpn I (Promega, Fitchburg, Wis., USA) to remove plasmid template DNA. The Dpn I was added directly to the PCR tube, mixed well, and incubated at 37° C. for 60 minutes, and then was column-purified using a MINELUTE® PCR Purification Kit (QIAGEN Inc., Valencia, Calif., USA) according to the manufacturer's instructions.

Fragment 2 was amplified using primers 613786 (sense) and 613787 (antisense) shown below.

```
613786 (sense):
                                (SEQ ID NO: 9)
taattaactagaggtgactgacacctggc 613787 (antisense):
                                (SEQ ID NO: 10)
catggccagttgtgtatatagaggattgagg
```

Fragment 2 was amplified by PCR in a reaction composed of 10 ng of plasmid pBM120, 0.5 µl of PHUSION® DNA Polymerase, 20 µmol of primer 613786, 20 µmol of primer 613787, 1 µl of 10 mM dNTPs, 10 µl of 5× PHUSION® HF buffer, and 35.5 µl of water. The reaction was incubated in an EPPENDORF® MASTERCYCLER® programmed for 1 cycle at 98° C. for 30 seconds; and 30 cycles each at 98° C. for 10 seconds, 60° C. for 10 seconds, and 72° C. for 4 minutes. The resulting 6.9 kb PCR product (Fragment 2) was treated with 1 µl of Dpn I to remove plasmid template DNA. The Dpn I was added directly to the PCR tube, mixed well, and incubated at 37° C. for 60 minutes, and then column-purified using a MINELUTE® PCR Purification Kit according to the manufacturer's instructions.

The following procedure was used to combine the two PCR fragments using megaprimer cloning. Fragments 1 and 2 were combined by PCR in a reaction composed of µl of each purified PCR product, 0.5 µl of PHUSION® DNA Polymerase, 1 µl of 10 mM dNTPs, 10 µl of 5× PHUSION® HF buffer, and 28.5 µl of water. The reaction was incubated in an EPPENDORF® MASTERCYCLER® programmed for 1 cycle at 98° C. for 30 seconds; and 40 cycles each at 98° C. for 10 seconds, 60° C. for 10 seconds, and 72° C. for 4 minutes. Two µl of the resulting PCR product DNA was then transformed into E. coli ONE SHOT® TOP10 electro-competent cells (Life Technologies, Grand Island, N.Y., USA) according the manufacturer's instructions. Fifty µl of transformed cells were spread onto LB plates supplemented with 100 µg of ampicillin per ml and incubated at 37° C. overnight. Individual transformants were picked into 3 ml of LB medium supplemented with 100 µg of ampicillin per ml and grown overnight at 37° C. with shaking at 250 rpm. The plasmid DNA was purified from the colonies using a QIAPREP® Spin Miniprep Kit (QIAGEN Inc., Valencia, Calif., USA). DNA sequencing using a 3130XL Genetic Analyzer (Applied Biosystems, Foster City, Calif., USA) was used to confirm the presence of each of both fragments in the final plasmid pDLHD0012 (FIG. 1).

Aspergillus oryzae strain MT3568 was transformed with plasmid pDLHD0012 comprising the VaXET16 gene according to the following protocol. Approximately 2-5×10$^7$ spores of A. oryzae strain MT3568 were inoculated into 100 ml of YP+2% glucose medium in a 500 ml shake flask and incubated at 28° C. and 110 rpm overnight. Ten ml of the overnight culture were filtered in a 125 ml sterile vacuum filter, and the mycelia were washed twice with 50 ml of 0.7 M KCl-20 mM CaCl$_2$. The remaining liquid was removed by vacuum filtration, leaving the mat on the filter. Mycelia were resuspended in 10 ml of 0.7 M KCl-20 mM CaCl$_2$ and transferred to a sterile 125 ml shake flask containing 20 mg of GLUCANEX® 200 G (Novozymes Switzerland AG, Neumatt, Switzerland) per ml and 0.2 mg of chitinase (Sigma-Aldrich, St. Louis, Mo., USA) per ml in 10 ml of 0.7 M KCl-20 mM CaCl$_2$. The mixture was incubated at 37° C. and 100 rpm for 30-90 minutes until protoplasts were generated from the mycelia. The protoplast mixture was filtered through a sterile funnel lined with MIRACLOTH® (Calbiochem, San Diego, Calif., USA) into a sterile 50 ml plastic centrifuge tube to remove mycelial debris. The debris in the MIRACLOTH® was washed thoroughly with 0.7 M KCl-20 mM CaCl$_2$, and centrifuged at 2500 rpm (537×g) for 10 minutes at 20-23° C. The supernatant was removed and the protoplast pellet was resuspended in 20 ml of 1 M sorbitol-10 mM Tris-HCl (pH 6.5)-10 mM CaCl$_2$. This step was repeated twice, and the final protoplast pellet was resuspended in 1 M sorbitol-10 mM Tris-HCl (pH 6.5)-10 mM CaCl$_2$ to obtain a final protoplast concentration of 2×10$^7$/ml.

Two micrograms of pDLHD0012 were added to the bottom of a sterile 2 ml plastic centrifuge tube. Then 100 µl of protoplasts were added to the tube followed by 300 µl of 60% PEG-4000 in 10 mM Tris-HCl (pH 6.5)-10 mM CaCl$_2$. The tube was mixed gently by hand and incubated at 37° C. for 30 minutes. Two ml of 1 M sorbitol-10 mM Tris-HCl (pH 6.5)-10 mM CaCl$_2$ were added to each transformation and the mixture was transferred onto 150 mm COVE agar plates. Transformation plates were incubated at 34° C. until colonies appeared.

Twenty-one transformant colonies were picked to fresh COVE agar plates and cultivated at 34° C. for four days until the transformants sporulated. Fresh spores were transferred to 48-well deep-well plates containing 2 ml of YP+2% maltodextrin, covered with a breathable seal, and grown for 4 days at 34° C. with no shaking. After 4 days growth samples of the culture media were assayed for xyloglucan endotransglycosylase activity using an iodine stain assay and for xyloglucan endotransglycosylase expression by SDS-PAGE.

The iodine stain assay for xyloglucan endotransglycosylase activity was performed according to the following protocol. In a 96-well plate, 5 µl of culture broth were added to a mixture of 5 µl of xyloglucan (Megazyme, Bray, United Kingdom) (5 mg/ml in water), 20 µl of xyloglucan oligomers (Megazyme, Bray, United Kingdom) (5 mg/ml in water), and 10 µl of 400 mM sodium citrate pH 5.5. The reaction mix was incubated at 37° C. for thirty minutes, quenched with 200 µl of a solution containing 14% (w/v) Na$_2$SO$_4$, 0.2% KI, 100 mM HCl, and 1% iodine (I$_2$), incubated in the dark for 30 minutes, and then the absorbance was measured in a plate reader at 620 nm. The assay demonstrated the presence of xyloglucan endotransglycosylase activity from several transformants.

SDS-PAGE was performed using a 8-16% CRITERION® Stain Free SDS-PAGE gel (Bio-Rad Laboratories, Inc., Hercules, Calif., USA), and imaging the gel with a Stain Free Imager (Bio-Rad Laboratories, Inc., Hercules, Calif., USA) using the following settings: 5-minute activation, automatic imaging exposure (intense bands), highlight saturated pixels=ON, color=Coomassie, and band detection, molecular weight analysis and reporting disabled. SDS-PAGE analysis indicated that several transformants expressed a protein of approximately 32 kDa corresponding to VaXET16.

Example 2: Construction of Plasmid pMMar27 as a Yeast Expression Plasmid Vector

Plasmid pMMar27 was constructed for expression of the T. terrestris Cel6A cellobiohydrolase II in yeast. The plasmid was generated from a lineage of yeast expression vectors: plasmid pMMar27 was constructed from plasmid pBM175b; plasmid pBM175b was constructed from plasmid pBM143b (WO 2008/008950) and plasmid pJLin201; and plasmid pJLin201 was constructed from pBM143b.

Plasmid pJLin201 is identical to pBM143b except an Xba I site immediately downstream of a *Thermomyces lanuginosus* lipase variant gene in pBM143b was mutated to a unique Nhe I site. A QUIKCHANGE® II XL Site-Directed Mutagenesis Kit (Stratagene, La Jolla, Calif., USA) was used to change the Xba I sequence (TCTAGA) to a Nhe I sequence (gCTAGc) in pBM143b. Primers employed to mutate the site are shown below.

```
Primer 999551 (sense):
                                    (SEQ ID NO: 11)
5'-ACATGTCTTTGATAAgCTAGcGGGCCGCATCATGTA-3'

Primer 999552 (antisense):
                                    (SEQ ID NO: 12)
5'-TACATGATGCGGCCCgCTAGcTTATCAAAGACATGT-3'
```

Lower Case Represents Mutated Nucleotides.

The amplification reaction was composed of 125 ng of each primer above, 20 ng of pBM143b, 1× QUIKCHANGE® Reaction Buffer (Stratagene, La Jolla, Calif., USA), 3 µl of QUIKSOLUTION® (Stratagene, La Jolla, Calif., USA), 1 µl of dNTP mix, and 1 µl of a 2.5 units/ml Pfu Ultra HF DNA polymerase in a final volume of 50 µl. The reaction was performed using an EPPENDORF® MASTERCYCLER® thermocycler programmed for 1 cycle at 95° C. for 1 minute; 18 cycles each at 95° C. for 50 seconds, 60° C. for 50 seconds, and 68° C. for 6 minutes and 6 seconds; and 1 cycle at 68° C. for 7 minutes. After the PCR, the tube was placed on ice for 2 minutes. One microliter of Dpn I was directly added to the amplification reaction and incubated at 37° C. for 1 hour. A 2 µl volume of the Dpn I digested reaction was used to transform *E. coli* XL10-GOLD® Ultracompetent Cells (Stratagene, La Jolla, Calif., USA) according to the manufacturer's instructions. *E. coli* transformants were selected on 2XYT plus ampicillin plates. Plasmid DNA was isolated from several of the transformants using a BIOROBOT® 9600. One plasmid with the desired Nhe I change was confirmed by restriction digestion and sequencing analysis and designated plasmid pJLin201. To eliminate possible PCR errors introduced by site-directed-mutagenesis, plasmid pBM175b was constructed by cloning the Nhe I site containing fragment back into plasmid pBM143b. Briefly, plasmid pJLin201 was digested with Nde I and Mlu I and the resulting fragment was cloned into pBM143b previously digested with the same enzymes using a Rapid Ligation Kit (Roche Diagnostics Corporation, Indianapolis, Ind., USA). Then, 7 µl of the Nde I/Mlu I digested pJLin201 fragment and 1 µl of the digested pBM143b were mixed with 2 µl of 5×DNA dilution buffer (Roche Diagnostics Corporation, Indianapolis, Ind., USA), 10 µl of 2× T4 DNA ligation buffer (Roche Diagnostics Corporation, Indianapolis, Ind., USA), and 1 µl of T4 DNA ligase (Roche Diagnostics Corporation, Indianapolis, Ind., USA) and incubated for 15 minutes at room temperature. Two microliters of the ligation were transformed into XL1-Blue Subcloning-Grade Competent Cells (Stratagene, La Jolla, Calif., USA) cells and spread onto 2XYT plus ampicillin plates. Plasmid DNA was purified from several transformants using a BIOROBOT® 9600 and analyzed by DNA sequencing using a 3130XL Genetic Analyzer to identify a plasmid containing the desired *A. nidulans* pyrG insert. One plasmid with the expected DNA sequence was designated pBM175b.

Figure 2:
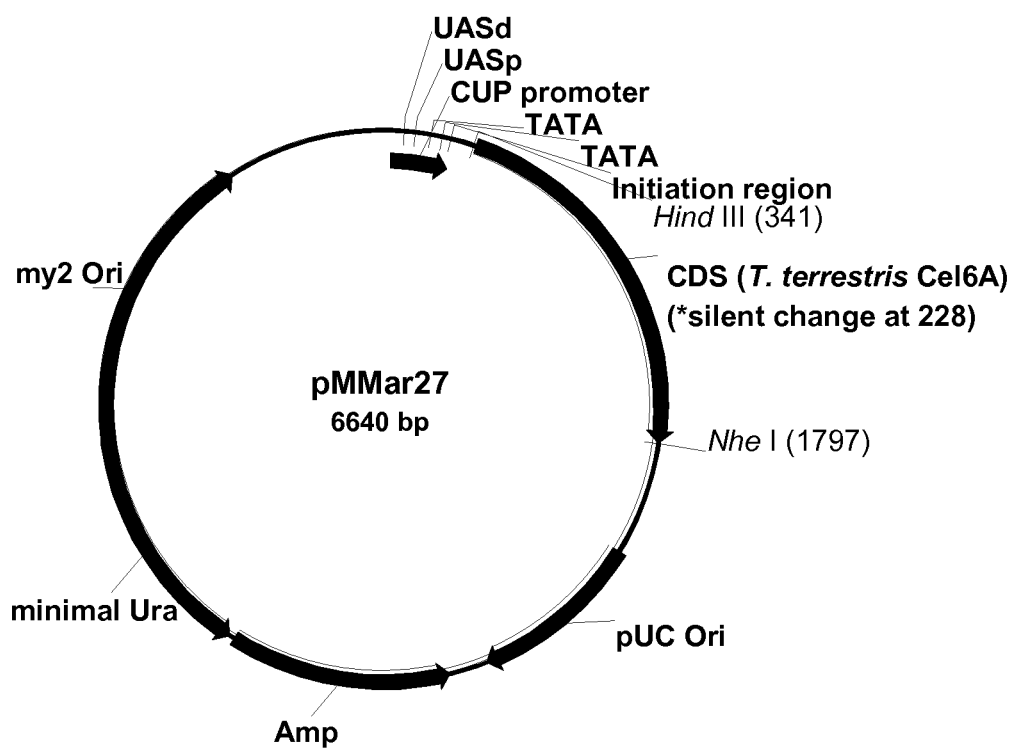
FIG. 2 shows a restriction map of pMMar27.

Plasmid pMMar27 was constructed from pBM175b and an amplified gene of *T. terrestris* Cel6A cellobiohydrolase II with overhangs designed for insertion into digested pBM175b. Plasmid pBM175b containing the *Thermomyces lanuginosus* lipase variant gene under control of the CUP I promoter contains unique Hind III and Nhe I sites to remove the lipase gene. Plasmid pBM175 was digested with these restriction enzymes to remove the lipase gene. After digestion, the empty vector was isolated by 1.0% agarose gel electrophoresis using TBE buffer where an approximately 5,215 bp fragment was excised from the gel and extracted using a QIAQUICK® Gel Extraction Kit. The ligation reaction (20 µl) was composed of 1× IN-FUSION® Buffer (BD Biosciences, Palo Alto, Calif., USA), 1× BSA (BD Biosciences, Palo Alto, Calif., USA), 1 µl of IN-FUSION® enzyme (diluted 1:10) (BD Biosciences, Palo Alto, Calif., USA), 99 ng of pBM175b digested with Hind III and Nhe I, and 36 ng of the purified *T. terrestris* Cel6A cellobiohydrolase II PCR product. The reaction was incubated at room temperature for 30 minutes. A 2 µl volume of the IN-FUSION® reaction was transformed into *E. coli* XL10-GOLD® Ultracompetent Cells. Transformants were selected on LB plates supplemented with 100 µg of ampicillin per ml. A colony was picked that contained the *T. terrestris* Cel6A inserted into the pBM175b vector in place of the lipase gene, resulting in pMMar27 (FIG. 2). The plasmid chosen contained a PCR error at position 228 from the start codon, TCT instead of TCC, but resulted in a silent change in the *T. terrestris* Cel6A cellobiohydrolase II.

Example 3: Construction of pEvFz1 Expression Vector

Expression vector pEvFz1 was constructed by modifying pBM120a (U.S. Pat. No. 8,263,824) to comprise the NA2/NA2-tpi promoter, *A. niger* amyloglucosidase terminator sequence (AMG terminator), and *Aspergillus nidulans* orotidine-5'-phosphate decarboxylase gene (pyrG) as a selectable marker.

Plasmid pEvFz1 was generated by cloning the *A. nidulans* pyrG gene from pAILo2 (WO 2004/099228) into pBM120a. Plasmids pBM120a and pAILo2 were digested with Nsi I overnight at 37° C. The resulting 4176 bp linearized pBM120a vector fragment and the 1479 bp pyrG gene insert from pAILo2 were each purified by 0.7% agarose gel electrophoresis using TAE buffer, excised from the gel, and extracted using a QIAQUICK® Gel Extraction Kit.

The 1479 bp pyrG gene insert was ligated to the Nsi I digested pBM120a fragment using a QUICK LIGATION™ Kit (New England Biolabs, Beverly, Mass., USA). The ligation reaction was composed of 1× QUICK LIGATION™ Reaction Buffer (New England Biolabs, Beverly, Mass., USA), 50 ng of Nsi I digested pBM120a vector, 54 ng of the 1479 bp Nsi I digested pyrG gene insert, and 1 µl of T4 DNA ligase in a total volume of 20 µl. The ligation mixture was incubated at 37° C. for 15 minutes followed at 50° C. for 15 minutes and then placed on ice.

Figure 3:
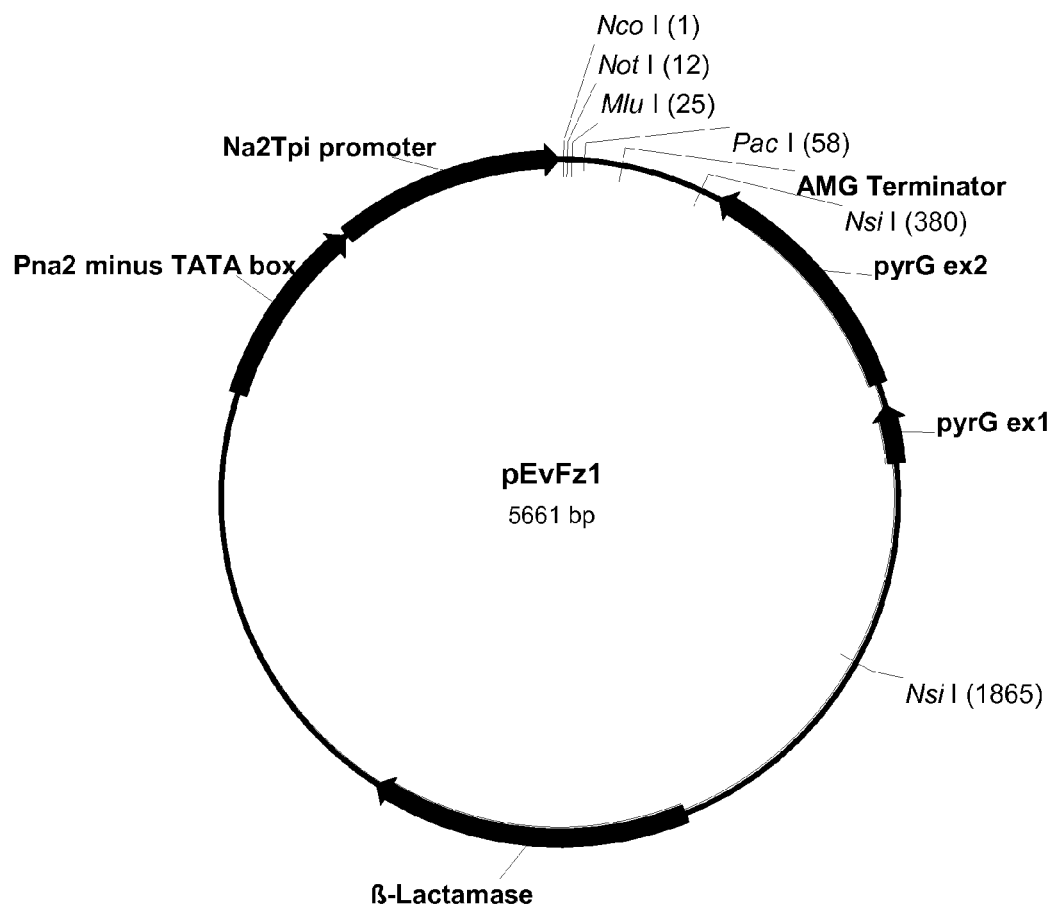
FIG. 3 shows a restriction map of pEvFz1.

One µl of the ligation mixture was transformed into ONE SHOT® TOP10 chemically competent *Escherichia coli* cells. Transformants were selected on 2XYT plus ampicillin plates. Plasmid DNA was purified from several transformants using a BIOROBOT® 9600 and analyzed by DNA sequencing using a 3130XL Genetic Analyzer to identify a plasmid containing the desired *A. nidulans* pyrG insert. One plasmid with the expected DNA sequence was designated pEvFz1 (FIG. 3).

Example 4: Construction of the Plasmid pDLHD0006 as a Yeast/*E. coli*/*A. Oryzae* Shuttle Vector Plasmid pDLHD0006 was constructed as a base vector to enable *A. oryzae* expression cassette library building using yeast recombinational cloning. Plasmid pDLHD0006 was generated by combining three DNA fragments using yeast recombinational cloning: Fragment 1 containing the *E. coli* pUC origin of replication, *E. coli* beta-lactamase (ampR) selectable marker, URA3 yeast selectable marker, and yeast 2 micron origin of replication from pMMar27 (Example 2); Fragment 2 containing the 10 amyR/NA2-tpi promoter (a hybrid of the promoters from the genes encoding *Aspergillus niger* neutral alpha-amylase and *Aspergillus oryzae* triose phosphate isomerase and including 10 repeated binding sites for the *Aspergillus oryzae* amyR transcription factor), *Thermomyces lanuginosus* lipase open reading frame (ORF), and *Aspergillus niger* glucoamylase terminator from pJaL1262 (WO 2013/178674); and Fragment 3 containing the *Aspergillus nidulans* pyrG selection marker from pEvFz1 (Example 3).

| pDLHD0006 | PCR Contents | PCR Template |
|---|---|---|
| Fragment 1 | *E. coli* ori/AmpR/URA/2 micron (4.1 kb) | pMMar27 |
| Fragment 2 | 10 amyR/NA2-tpi PR/lipase/Tamg (4.5 kb) | pJaL1262 |
| Fragment 3 | pyrG gene from pEvFz1 (1.7 kb) | pEvFz1 |

Fragment 1 was amplified using primers 613017 (sense) and 613018 (antisense) shown below. Primer 613017 was designed to contain a flanking region with sequence homology to Fragment 3 (lower case) and primer 613018 was designed to contain a flanking region with sequence homology to Fragment 2 (lower case) to enable yeast recombinational cloning between the three PCR fragments.

```
Primer 613017 (sense):
                                   (SEQ ID NO: 13)
ttaatcgccttgcagcacaCCGCTTCCTCGCTCACTGACTC 613018 (antisense):
                                   (SEQ ID NO: 14)
acaataaccctgataaatgcGGAACAACACTCAACCCTATCTCGGTC
```

Fragment 1 was amplified by PCR in a reaction composed of 10 ng of plasmid pMMar27, 0.5 µl of PHUSION® DNA Polymerase (New England Biolabs, Inc., Ipswich, Mass., USA), 20 µmol of primer 613017, 20 µmol of primer 613018, 1 µl of 10 mM dNTPs, 10 µl of 5× PHUSION® HF buffer, and 35.5 µl of water. The reaction was incubated in an EPPENDORF® MASTERCYCLER® programmed for 1 cycle at 98° C. for 30 seconds; and 30 cycles each at 98° C. for 10 seconds, 60° C. for 10 seconds, and 72° C. for 1.5 minutes. The resulting 4.1 kb PCR product (Fragment 1) was used directly for yeast recombination with Fragments 2 and 3 below.

Fragment 2 was amplified using primers 613019 (sense) and 613020 (antisense) shown below. Primer 613019 was designed to contain a flanking region of sequence homology to Fragment 1 (lower case) and primer 613020 was designed to contain a flanking region of sequence homology to Fragment 3 (lower case) to enable yeast recombinational cloning between the three PCR fragments.

```
613019 (sense):
                                   (SEQ ID NO: 15)
agatagggttgagtgttgttccGCATTTATCAGGGTTATTGT
CTCATGAGCGG 613020 (antisense):
                                   (SEQ ID NO: 16)
ttctacacgaaggaaagagGAGGAGAGAGTTGAACCTGGACG
```

Fragment 2 was amplified by PCR in a reaction composed of 10 ng of plasmid pJaL1262, 0.5 µl of PHUSION® DNA Polymerase, 20 µmol of primer 613019, 20 µmol of primer 613020, 1 µl of 10 mM dNTPs, 10 µl of 5× PHUSION® HF buffer, and 35.5 µl of water. The reaction was incubated in an EPPENDORF® MASTERCYCLER® programmed for 1 cycle at 98° C. for 30 seconds; 30 cycles each at 98° C. for 10 seconds, 60° C. for 10 seconds, and 72° C. for 2 minutes; and a 20° C. hold. The resulting 4.5 kb PCR product (Fragment 2) was used directly for yeast recombination with Fragment 1 above and Fragment 3 below.

Fragment 3 was amplified using primers 613022 (sense) and 613021 (antisense) shown below. Primer 613021 was designed to contain a flanking region of sequence homology to Fragment 2 (lower case) and primer 613022 was designed to contain a flanking region of sequence homology to Fragment 1 (lower case) to enable yeast recombinational cloning between the three PCR fragments.

```
613022 (sense):
                                   (SEQ ID NO: 17)
aggttcaactctctcctcCTCTTTCCTTCGTGTAGAAGACCAGACAG 613021 (antisense):
                                   (SEQ ID NO: 18)
tcagtgagcgaggaagcggTGTGCTGCAAGGCGATTAAGTTGG
```

Fragment 3 was amplified by PCR in a reaction composed of 10 ng of plasmid pEvFz1 (Example 3), 0.5 µl of PHUSION® DNA Polymerase, 20 µmol of primer 613021, 20 µmol of primer 613022, 1 µl of 10 mM dNTPs, 10 µl of 5× PHUSION® HF buffer, and 35.5 µl of water. The reaction was incubated in an EPPENDORF® MASTERCYCLER® programmed for 1 cycle at 98° C. for 30 seconds; 30 cycles each at 98° C. for 10 seconds, 60° C. for 10 seconds, and 72° C. for 2 minutes; and a 20° C. hold. The resulting 1.7 kb PCR product (Fragment 3) was used directly for yeast recombination with Fragments 1 and 2 above.

The following procedure was used to combine the three PCR fragments using yeast homology-based recombinational cloning. A 20 µl aliquot of each of the three PCR fragments was combined with 100 µg of single-stranded deoxyribonucleic acid from salmon testes (Sigma-Aldrich, St. Louis, Mo., USA), 100 µl of competent yeast cells of strain YNG318 (*Saccharomyces cerevisiae* ATCC 208973), and 600 µl of PLATE Buffer (Sigma Aldrich, St. Louis, Mo., USA), and mixed. The reaction was incubated at 30° C. for 30 minutes with shaking at 200 rpm. The reaction was then continued at 42° C. for 15 minutes with no shaking. The cells were pelleted by centrifugation at 5,000×g for 1 minute and the supernatant was discarded. The cell pellet was suspended in 200 µl of autoclaved water and split over two agar plates containing Synthetic defined medium lacking uridine and incubated at 30° C. for three days. The yeast colonies were isolated from the plate using 1 ml of autoclaved water. The cells were pelleted by centrifugation at 13,000×g for 30 seconds and a 100 µl aliquot of glass beads were added to the tube. The cell and bead mixture was suspended in 250 µl of P1 buffer (QIAGEN Inc., Valencia, Calif., USA) and then vortexed for 1 minute to lyse the cells.

Figure 4:
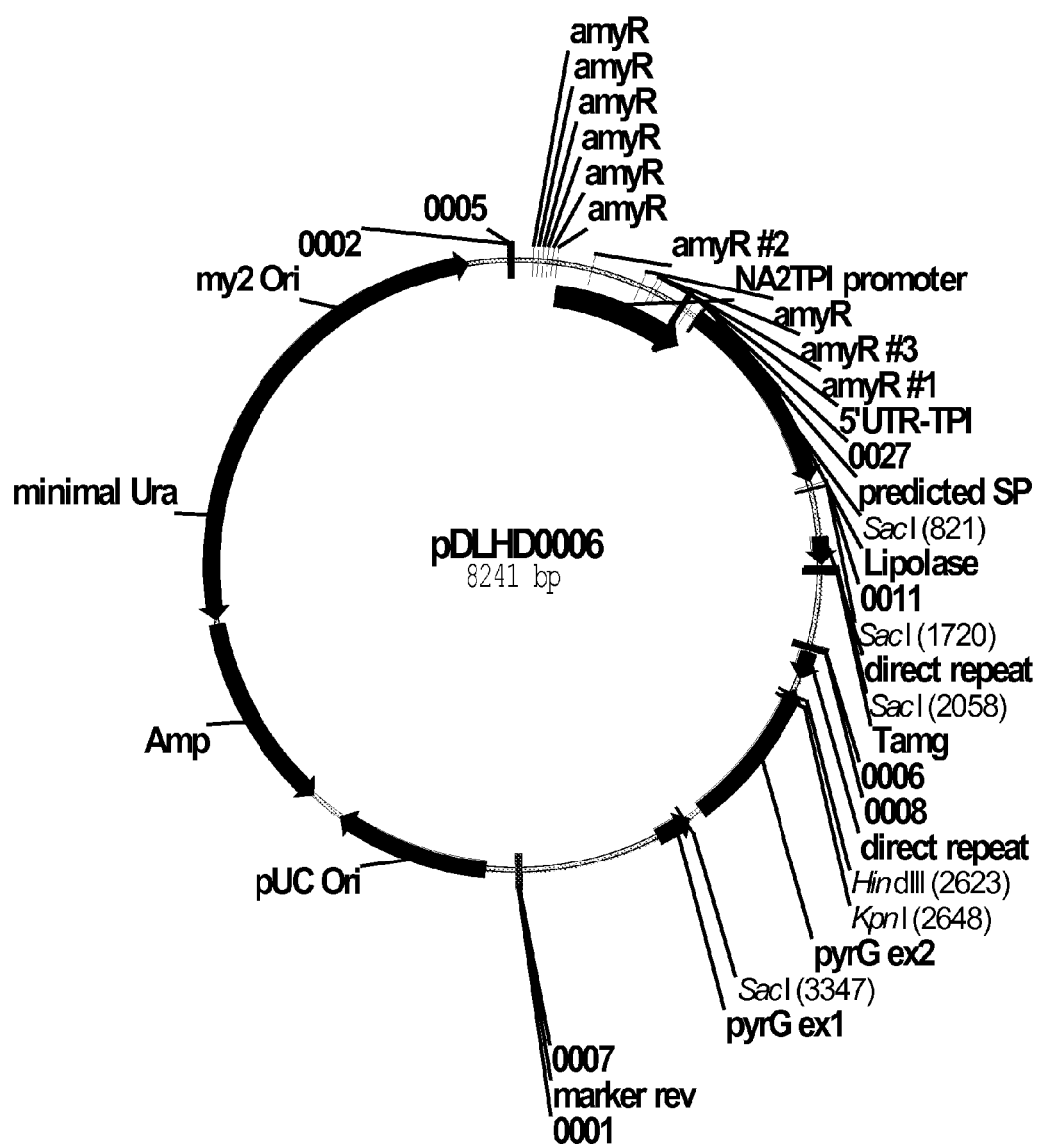
FIG. 4 shows a restriction map of pDLHD0006.

The plasmid DNA was purified using a QIAPREP® Spin Miniprep Kit. A 3 µl aliquot of the plasmid DNA was then transformed into *E. coli* ONE SHOT® TOP10 electrocompetent cells according the manufacturer's instructions. Fifty µl of transformed cells were spread onto LB plates supplemented with 100 µg of ampicillin per ml and incubated at 37° C. overnight. Transformants were each picked into 3 ml of LB medium supplemented with 100 µg of ampicillin per ml and grown overnight at 37° C. with shaking at 250 rpm. The plasmid DNA was purified from colonies using a QIAPREP® Spin Miniprep Kit. DNA sequencing with a 3130XL Genetic Analyzer was used to confirm the presence of each of the three fragments in a final plasmid designated pDLHD0006 (FIG. 4).

Example 5: Preparation of *Arabidopsis thaliana* Xyloglucan Endotransglycosylase 14

*Arabidopsis thaliana* xyloglucan endotransglycosylase (AtXET14; SEQ ID NO: 4 [native DNA sequence], SEQ ID NO: 5 [synthetic DNA sequence], and SEQ ID NO: 6 [deduced amino acid sequence]) was recombinantly produced in *Aspergillus oryzae* JaL355 (WO 2008/138835).

The vector pDLHD0039 was constructed to express the AtXET14 gene in multi-copy in *Aspergillus oryzae*. Plasmid pDLHD0039 was generated by combining two DNA fragments using restriction-free cloning: Fragment 1 containing the AtXET14 ORF and flanking sequences with homology to vector pDLHD0006 (Example 4), and Fragment 2 consisting of an inverse PCR amplicon of vector pDLHD0006.

Fragment 1 was amplified using primers AtXET14F (sense) and AtXET14R (antisense) shown below, which were designed to contain flanking regions of sequence homology to vector pDLHD0006 (lower case) for ligation-free cloning between the PCR fragments.

```
Primer AtXET14F (sense):
                                        (SEQ ID NO: 19)
ttcctcaatcctctatatacacaactggccATGGCCTGTTTCGCAAC
CAAACAG AtXET14R (antisense):
                                        (SEQ ID NO: 20)
agctcgctagagtcgacctaGAGTTTACATTCCTTGGGGAGACCCTG
```

Fragment 1 was amplified by PCR in a reaction composed of 10 ng of a GENEART® vector µMA containing the AtXET14 synthetic DNA sequence cloned between the Sac I and Kpn I sites, 0.5 µl of PHUSION® DNA Polymerase (New England Biolabs, Inc., Ipswich, Mass., USA), 20 µmol of primer AtXET14F, 20 µmol of primer AtXET14R, 1 µl of 10 mM dNTPs, 10 µl of 5× PHUSION® HF buffer, and 35.5 µl of water. The reaction was incubated in an EPPENDORF® MASTERCYCLER® programmed for 1 cycle at 98° C. for 30 seconds; and 30 cycles each at 98° C. for 10 seconds, 60° C. for 10 seconds, and 72° C. for 30 seconds. The resulting 0.9 kb PCR product (Fragment 1) was treated with 1 µl of Dpn I to remove plasmid template DNA. The Dpn I was added directly to the PCR tube, mixed well, and incubated at 37° C. for 60 minutes, and then column-purified using a MINELUTE® PCR Purification Kit.

Fragment 2 was amplified using primers 614604 (sense) and 613247 (antisense) shown below.

```
614604 (sense):
                                        (SEQ ID NO: 21)
taggtcgactctagcgagctcgagatc 613247 (antisense):
                                        (SEQ ID NO: 22)
catggccagttgtgtatatagaggattgaggaaggaagag
```

Fragment 2 was amplified by PCR in a reaction composed of 10 ng of plasmid pDLHD0006, 0.5 µl of PHUSION® DNA Polymerase, 20 µmol of primer 614604, 20 µmol of primer 613247, 1 µl of 10 mM dNTPs, 10 µl of 5× PHUSION® HF buffer, and 35.5 µl of water. The reaction was incubated in an EPPENDORF® MASTERCYCLER® programmed for 1 cycle at 98° C. for 30 seconds; and 30 cycles each at 98° C. for 10 seconds, 60° C. for 10 seconds, and 72° C. for 4 minutes. The resulting 7.3 kb PCR product (Fragment 2) was treated with 1 µl of Dpn I to remove plasmid template DNA. Dpn I was added directly to the PCR tube, mixed well, and incubated at 37° C. for 60 minutes, and then column-purified using a MINELUTE® PCR Purification Kit.

Figure 5:
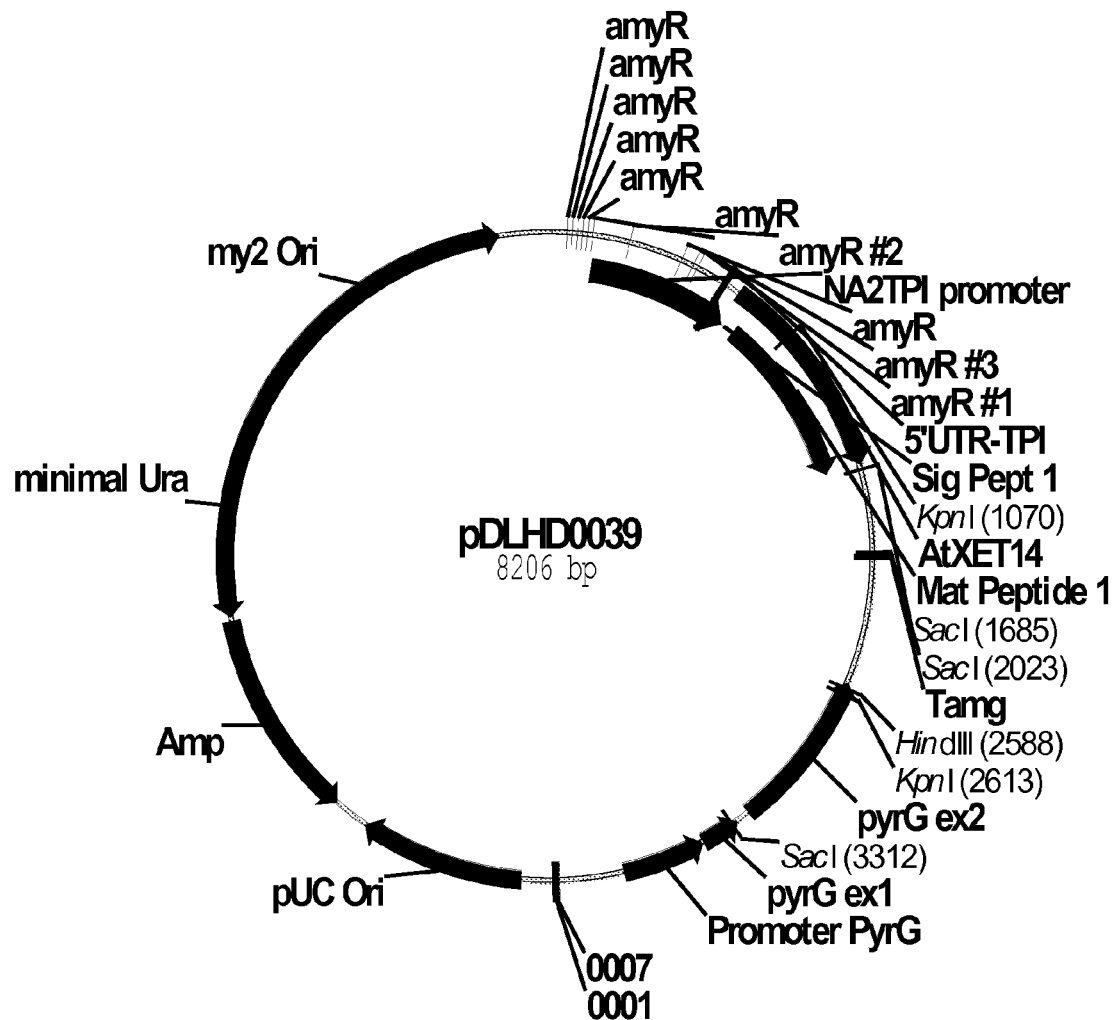
FIG. 5 shows a restriction map of pDLHD0039.

The two PCR fragments were combined using a GENEART® Seamless Cloning and Assembly Kit (Invitrogen, Carlsbad, Calif., USA) according to manufacturer's instructions. Three µl of the resulting reaction product DNA were then transformed into *E. coli* ONE SHOT® TOP10 electrocompetent cells. Fifty µl of transformed cells were spread onto LB plates supplemented with 100 µg of ampicillin per ml and incubated at 37° C. overnight. Individual transformant colonies were picked into 3 ml of LB medium supplemented with 100 µg of ampicillin per ml and grown overnight at 37° C. with shaking at 250 rpm. The plasmid DNA was purified from colonies using a QIAPREP® Spin Miniprep Kit according to the manufacturer's instructions. DNA sequencing with a 3130XL Genetic Analyzer was used to confirm the presence of each of both fragments in the final plasmid pDLHD0039 (FIG. 5).

*Aspergillus oryzae* strain JaL355 was transformed with plasmid pDLHD0039 comprising the AtXET14 gene according to the following protocol. Approximately 2-5×10$^7$ spores of *Aspergillus oryzae* JaL355 were inoculated into 100 ml of YP+2% glucose+10 mM uridine in a 500 ml shake flask and incubated at 28° C. and 110 rpm overnight. Ten ml of the overnight culture was filtered in a 125 ml sterile vacuum filter, and the mycelia were washed twice with 50 ml of 0.7 M KCl-20 mM CaCl$_2$. The remaining liquid was removed by vacuum filtration, leaving the mat on the filter. Mycelia were resuspended in 10 ml of 0.7 M KCl-20 mM CaCl$_2$ and transferred to a sterile 125 ml shake flask containing 20 mg of GLUCANEX® 200 G per ml and 0.2 mg of chitinase per ml in 10 ml of 0.7 M KCl-20 mM CaCl$_2$. The mixture was incubated at 37° C. and 100 rpm for 30-90 minutes until protoplasts were generated from the mycelia. The protoplast mixture was filtered through a sterile funnel lined with MIRACLOTH® into a sterile 50 ml plastic centrifuge tube to remove mycelial debris. The debris in the MIRACLOTH® was washed thoroughly with 0.7 M KCl-20 mM CaCl$_2$, and centrifuged at 2500 rpm (537×g) for 10 minutes at 20-23° C. The supernatant was removed and the protoplast pellet was resuspended in 20 ml of 1 M sorbitol-10 mM Tris-HCl (pH 6.5)-10 mM CaCl$_2$. This step was repeated twice, and the final protoplast pellet was resuspended in 1 M sorbitol-10 mM Tris-HCl (pH 6.5)-10 mM $CaCl_2$ to obtain a final protoplast concentration of $2\times10^7$/ml.

Two micrograms of pDLHD0039 were added to the bottom of a sterile 2 ml plastic centrifuge tube. Then 100 μl of protoplasts were added to the tube followed by 300 μl of 60% PEG-4000 in 10 mM Tris-HCl (pH 6.5)-10 mM $CaCl_2$. The tube was mixed gently by hand and incubated at 37° C. for 30 minutes. Two ml of 1 M sorbitol-10 mM Tris-HCl (pH 6.5)-10 mM $CaCl_2$ were added to each transformation and the mixture was transferred onto 150 mm Minimal medium agar plates. Transformation plates were incubated at 34° C. until colonies appeared.

Thirty-five transformant colonies were picked to fresh Minimal medium agar plates and cultivated at 34° C. for four days until the strains sporulated. Fresh spores were transferred to 48-well deep-well plates containing 2 ml of YP+2% maltodextrin, covered with a breathable seal, and grown for 4 days at 28° C. with no shaking. After 4 days growth the culture medium was assayed for xyloglucan endotransglycosylase activity and for xyloglucan endotransglycosylase expression by SDS-PAGE.

Xyloglucan endotransglycosylase activity was measured using the iodine stain assay described in Example 1. The assay demonstrated the presence of xyloglucan endotransglycosylase activity in several transformants.

SDS-PAGE was performed as described in Example 1. SDS-PAGE analysis indicated that several transformants expressed a protein of approximately 32 kDa corresponding to AtXET14.

Example 6: Generation of Fluorescein Isothiocyanate-Labeled Xyloglucan

Fluorescein isothiocyanate-labeled xyloglucan oligomers (FITC-XGOs) were generated by reductive amination of the reducing ends of xyloglucan oligomers (XGOs) according to the procedure described by Zhou et al., 2006, *Biocatalysis and Biotransformation* 24: 107-120), followed by conjugation of the amino groups of the XGOs to fluorescein isothiocyanate isomer I (Sigma Aldrich, St. Louis, Mo., USA) in 100 mM sodium bicarbonate pH 9.0 for 24 hours at room temperature. Conjugation reaction products were concentrated to dryness in vacuo, dissolved in 0.5 ml of deionized water, and purified by silica gel chromatography, eluting with a gradient from 100:0:0.04 to 70:30:1 acetonitrile:water:acetic acid as mobile phase. Purity and product identity were confirmed by evaporating the buffer, dissolving in $D_2O$ (Sigma Aldrich, St. Louis, Mo., USA), and analysis by $^1H$ NMR using a Varian 400 MHz MercuryVx (Agilent, Santa Clara, Calif., USA). Dried FITC-XGOs were stored at −20° C. in the dark, and were desiccated during thaw.

Twenty-four ml of 10 mg of tamarind seed xyloglucan (Megazyme, Bray, UK) per ml of deionized water, 217 μl of 7.9 mg of FITC-XGOs per ml of deionized water, 1.2 ml of 400 mM sodium citrate pH 5.5, and 600 μl of 1.4 mg of VaXET16 per ml of 20 mM sodium citrate pH 5.5 were mixed thoroughly and incubated overnight at room temperature. Following overnight incubation, FITC-XG was precipitated by addition of ice cold ethanol to a final volume of 110 ml, mixed thoroughly, and incubated at 4° C. overnight. The precipitated FITC-XG was washed with water and then transferred to Erlenmeyer bulbs. Residual water and ethanol were removed by evaporation using an EZ-2 Elite evaporator (SP Scientific/Genevac, Stone Ridge, N.Y., USA) for 4 hours. Dried samples were dissolved in water, and the volume was adjusted to 48 ml with deionized water to generate a final FITC-XG concentration of 5 mg per ml with an expected average molecular weight of 100 kDa.

Example 7: Fluorescence Polarization Assay for Xyloglucan Endotransglycosylation Activity Xyloglucan endotransglycosylation activity was assessed using the following assay. Reactions of 200 μl containing 1 mg of tamarind seed xyloglucan per ml, 0.01 mg/ml FITC-XGOs prepared as described in Example 6, and 10 μl of appropriately diluted XET were incubated for 10 minutes at 25° C. in 20 mM sodium citrate pH 5.5 in opaque 96-well microtiter plates. Fluorescence polarization was monitored continuously over this time period, using a SPECTRAMAX® M5 microplate reader (Molecular Devices, Sunnyvale, Calif., USA) in top-read orientation with an excitation wavelength of 490 nm, an emission wavelength of 520 nm, a 495 cutoff filter in the excitation path, high precision (100 reads), and medium photomultiplier tube sensitivity. XET-dependent incorporation of fluorescent XGOs into non-fluorescent xyloglucan (XG) results in increasing fluorescence polarization over time. The slope of the linear regions of the polarization time progress curves was used to determine the activity.

Example 8: Purification of *Vigna angularis* Xyloglucan Endotransglycosylase 16

One liter solutions of crude fermentation broth of *Vigna angularis* were filtered using a 0.22 μm STERICUP® filter (Millipore, Bedford, Mass., USA) and the filtrates were stored at 4° C. Cell debris was resuspended in 1 liter of 0.25% TRITON® X-100 (4-(1,1,3,3-tetramethylbutyl)phenyl-polyethylene glycol; Sigma Aldrich, St. Louis, Mo., USA)-20 mM sodium citrate pH 5.5, incubated at least 30 minutes at room temperature, and then filtered using a 0.22 μm STERICUP® filter. The filtrates containing *Vigna angularis* xyloglucan endotransglycosylase 16 (VaXET16) were pooled and concentrated to a volume between 500 and 1500 ml using a VIVAFLOW® 200 tangential flow concentrator (Millipore, Bedford, Mass., USA) equipped with a 10 kDa molecular weight cutoff membrane.

The concentrated filtrates were loaded onto a 150 ml Q SEPHAROSE® Big Beads column (GE Healthcare Lifesciences, Piscataway, N.J., USA), pre-equilibrated with 20 mM sodium citrate pH 5.5, and eluted isocratically with the same buffer. The eluent was loaded onto a 75 ml Phenyl SEPHAROSE® HP column (GE Healthcare Lifesciences, Piscataway, N.J., USA) pre-equilibrated in 20% ethylene glycol-20 mM sodium citrate pH 5.5. VaXET16 was eluted using a linear gradient from 20% to 50% of 70% ethylene glycol in 20 mM sodium citrate pH 5.5 over 4 column volumes.

Purified VaXET16 was quantified using a BCA assay (Pierce, Rockford, Ill., USA) in a 96-well plate format with bovine serum albumin (Pierce, Rockford, Ill., USA) as a protein standard at concentrations between 0 and 2 mg/ml and was determined to be 1.40 mg/ml. VaXET16 homogeneity was confirmed by the presence of a single band at approximately 32 kDa using a 8-16% gradient CRITERION® Stain Free SDS-PAGE gel, and imaging the gel with a Stain Free Imager using the following settings: 5-minute activation, automatic imaging exposure (intense bands), highlight saturated pixels=ON, color=Coomassie, and band detection, molecular weight analysis and reporting disabled.

The activity of the purified VaXET16 was determined by measuring the rate of incorporation of fluorescein isothiocyanate-labeled xyloglucan oligomers into tamarind seed xyloglucan (Megazyme, Bray, UK) by fluorescence polarization (as described in Example 7).

The apparent activity was 18.5±1.2 P s$^{-1}$ mg$^{-1}$. The purified VaXET16 preparation was tested for background enzyme activities including xylanase, amylase, cellulase, beta-glucosidase, protease, amyloglucosidase, and lipase using standard assays as shown below.

Xylanase activity was assayed using wheat arabinoxylan as substrate at pH 6.0 and 50° C. Xylan hydrolysis was assessed colorimetrically at 405 nm by addition of alkaline solution containing PHBAH. One FXU(S) is defined as the endoxylanase activity using Shearzyme® (Novozymes AIS) as a standard.

Amylase activity was assayed using starch as substrate at pH 2.5 and 37° C. Starch hydrolysis was assessed by measuring the residual starch colorimetrically at 600 nm by addition of iodine solution. One FAU(A) is defined as the acid alpha-amylase activity using acid fungal alpha-amylase (available from Novozymes AIS) as a standard.

Amylase activity was assayed using (4,6-ethylidene(G7)-p-nitrophenyl(G1)-α,D-maltoheptaoside (4,6-ethylidene-G7-pNP) as substrate at pH 7 and 37° C. Hydrolysis of the substrate produces p-nitrophenol, and was assessed colorimetrically at 405 nm. One FAU(F) is defined as fungal alpha-amylase units using Fungamyl® (Novozymes AIS) as a standard.

Cellulase activity was assayed using carboxymethylcellulose (CMC) as substrate at pH 5.0 and 50° C. CMC hydrolysis was assessed colorimetrically at 405 nm by addition of an alkaline solution containing para-hydroxybenzoic acid hydrazide (PHBAH). One CNU(B) is defined as the cellulase activity using NS22084 enzyme (Novozymes AIS) as a standard.

Beta-glucosidase activity was assayed using cellobiose as substrate at pH 5.0 and 50° C. Production of glucose from cellobiose was assessed using a coupled enzyme assay with hexokinase and glucose-6-phosphate dehydrogenase converting glucose to 6-phosphoglucanate following reduction of NAD to NADH at 340 nm. One CBU(B) is defined as the amount of enzyme which releases 2 μmole of glucose per minute using cellobiase as a standard.

The protease assay was performed using an EnzChek® Protease Assay Kit (green fluorescence) (Life Technologies, Inc., Grand Island, N.Y., USA) with casein as substrate at pH 6 or 9 and ambient temperature. One KMTU is defined as a kilo microbial trypsin unit related to the amount of enzyme that produces 1 μmole of p-nitroaniline per minute.

Amyloglucosidase activity was assayed using maltose as substrate at pH 4.3 and 37° C. Conversion of maltose to glucose was assessed using a coupled enzyme assay with hexokinase and glucose-6-phosphate dehydrogenase converting glucose to 6-phosphoglucanate following reduction of NAD to NADH at 340 nm. One AGU is defined as amyloglucosidase units using AMG® (Novozymes A/S) as a standard.

The 4-methylumbelliferyl beta-D-lactoside (MUL) assay was performed at pH 7 and ambient temperature and measured fluorometrically at 360 nm excitation and 465 nm emission.

Lipase activity was assayed using 4-nitropenyl butyrate (pNP-butyrate) as substrate at pH 7.5 and ambient temperature. pNP-butyrate hydrolysis was assessed colorimetrically following p-nitrophenol release at 405 nm. One LU is defined as the amount of enzyme which releases 1 μmole of titratable butyric acid using LIPOLASE® (Novozymes A/S) as a standard.

| Assay | Substrate | Additional Assay Dilution | Activity Units | Activity Units/ml |
|---|---|---|---|---|
| Xylanase FXU(S) | Wheat arabinoxylan | 4-fold | FXU(S) | ND |
| Amylase FAU(A) | Starch | 4-fold | FAU(A) | ND |
| Amylase FAU(F) | Ethylidene-G7-pNp | 4-fold | FAU(F) | ND |
| Cellulase CNU(B) | CMC | 4-fold | CNU(B) | ND |
| Beta-glucosidase CBU(B) | Cellobiose | 4-fold | CBU(B) | ND |
| Protease, pH 6 (EnzCheck) | Casein | none | KMTU | 740 |
| Protease, pH 9 (EnzCheck) | Casein | none | KMTU | 332 |
| Amyloglucosidase AGU | Maltose | 4-fold | AGU | ND |
| MUL | MUL | none | Unitless | ND |
| Lipase | pNP-Butyrate | none | LU | 0.02 |

Example 9: Purification of *Arabidopsis thaliana* Xyloglucan Endotransglycosylase 14

The purification and quantification of the *Arabidopsis thaliana* xyloglucan endotransglycosylase 14 (AtXET14) was performed as described for VaXET16 in Example 8, except that elution from the Phenyl SEPHAROSE® HP column was performed using a linear gradient from 40% to 90% of 70% ethylene glycol in 20 mM sodium citrate pH 5.5 over 4 column volumes.

AtXET14 homogeneity was confirmed by the presence of a single band at approximately 32 kDa using a 8-16% CRITERION® Stain Free SDS-PAGE gel, and imaging the gel with a Stain Free Imager using the following settings: 5-minute activation, automatic imaging exposure (intense bands), highlight saturated pixels=ON, color=Coomassie, and band detection, molecular weight analysis and reporting disabled.

Purified AtXET14 was quantified using a BCA assay in a 96-well plate format with bovine serum albumin as a protein standard at concentrations between 0 and 2 mg/ml and was determined to be 1.49 mg/ml.

The activity of the purified AtXET14 was determined as described in Example 7. The apparent activity was 34.7±0.9 P s$^{-1}$ mg$^{-1}$.

The purified AtXET14 preparation was tested for background activities including xylanase, amylase, cellulase, beta-glucosidase, protease, amyloglucosidase, and lipase using standard assays as shown below. The standard assays are described in Example 8.

| Assay | Substrate | Additional Assay Dilution | Activity Units | Activity Units/mL |
|---|---|---|---|---|
| Xylanase FXU(S) | Wheat arabinoxylan | 4-fold | FXU(S) | ND |
| Amylase FAU(A) | Starch | 4-fold | FAU(A) | ND |
| Amylase FAU(F) | Ethylidene-G7-pNp | 4-fold | FAU(F) | ND |
| Cellulase CNU(B) | CMC | 4-fold | CNU(B) | ND |
| Beta-glucosidase CBU(B) | Cellobiose | 4-fold | CBU(B) | ND |
| Protease, pH 6 (EnzCheck) | Casein | none | KMTU | 82 |
| Protease, pH 9 (EnzCheck) | Casein | none | KMTU | 53 |
| Amyloglucosidase AGU | Maltose | 4-fold | AGU | ND |

-continued

| Assay | Substrate | Additional Assay Dilution | Activity Units | Activity Units/mL |
|---|---|---|---|---|
| MUL | MUL | none | Unitless | ND |
| Lipase | pNP-Butyrate | none | LU | 0.24 |

Example 10: Prevention of Fruit Dehydration by Xyloglucan and Xyloglucan with *Arabidopsis thaliana* Xyloglucan Endotransglycosylase 14

Carnation stems and banana stems (Chiquita organic) were cut into thin sections and Granny Smith apples (Yakima Fresh) were cut into small slices using a razor blade. A 0.5 cm length at the end of each stem was discarded, and the remaining sections were either dipped in a solution of 5 mg of tamarind seed xyloglucan (Megazyme, Bray, UK) per ml of 20 mM sodium citrate pH 5.5 and the excess xyloglucan removed by touching the stem to the side of the container, or were not dipped. Several flower stems were used, and sections from each stem were divided into both dipped and not-dipped groups to control for stem to stem variation. Each section was then incubated on its side, cut ends not touching the bottom of the well, in either a CoStar 3513 12-well or CoStar 3524 24-well, flat bottomed, covered cell culture plate (Corning, Tewksbury, Mass., USA). The samples were incubated at room temperature for 5 days. Photographs were taken at 1, 2, and 5 days to illustrate the extent of desiccation/oxidation.

Figure 6:
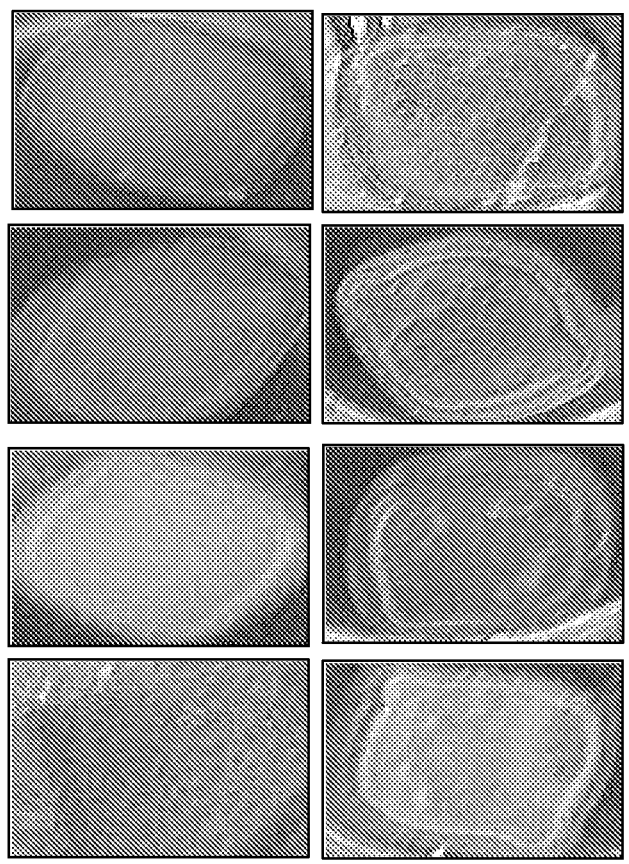
FIG. 6 shows carnation stems dipped in tamarind seed xyloglucan in the upper row, or not dipped in the lower row, following 1 day of incubation at room temperature.

FIG. 6 shows carnation stems dipped in xyloglucan in the upper row, or not dipped in the lower row, following 1 day of incubation at room temperature. The xyloglucan dipped carnation stems appeared smooth and hydrated, whereas the carnation stems that were not dipped appeared desiccated, with white, scaly, dry patches. After 1 day of incubation, carnation stems that had been dipped in xyloglucan appeared substantially more hydrated than those that had not been dipped. By 2 days of incubation, both dipped and not dipped stem slices appeared similarly dry, thus the xyloglucan reduced the rate of carnation stem dehydration. No qualitative differences between banana stems dipped and not dipped were observed, though these were cut more thickly than the carnations.

Figure 7A:
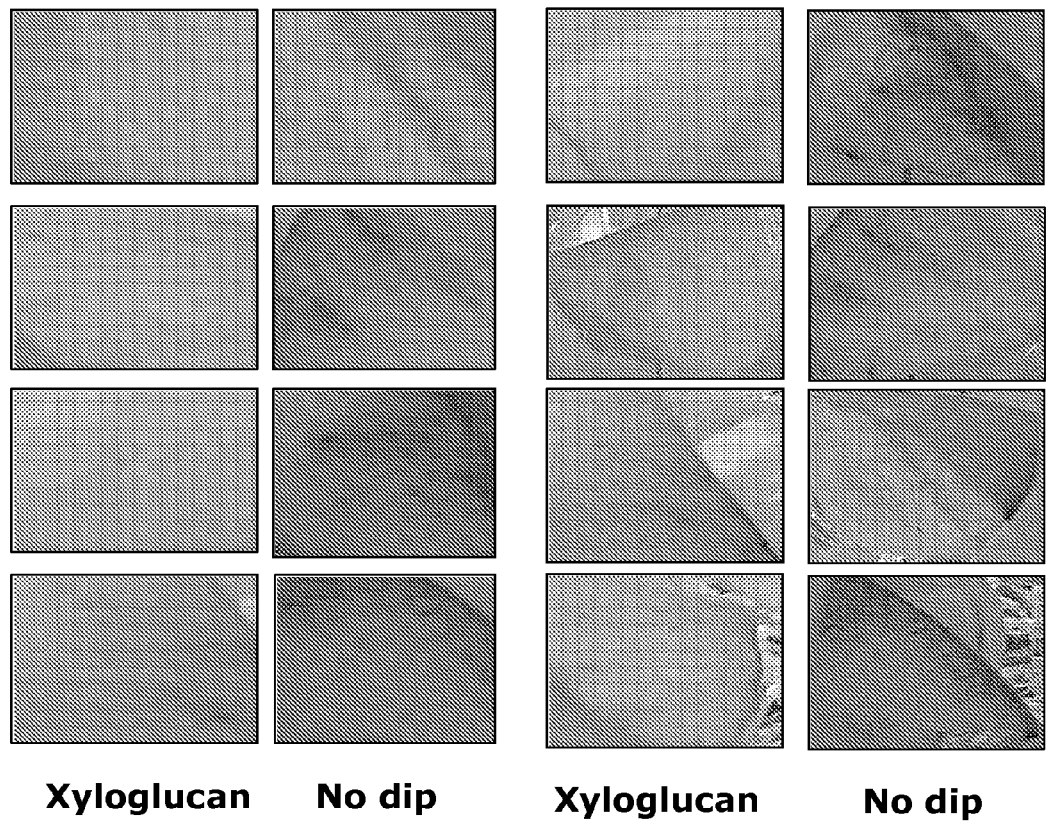
FIG. 7A shows apple slices dipped in tamarind seed xyloglucan in the upper row, or not dipped in the lower row, after 2 days of incubation.
Figure 7B:
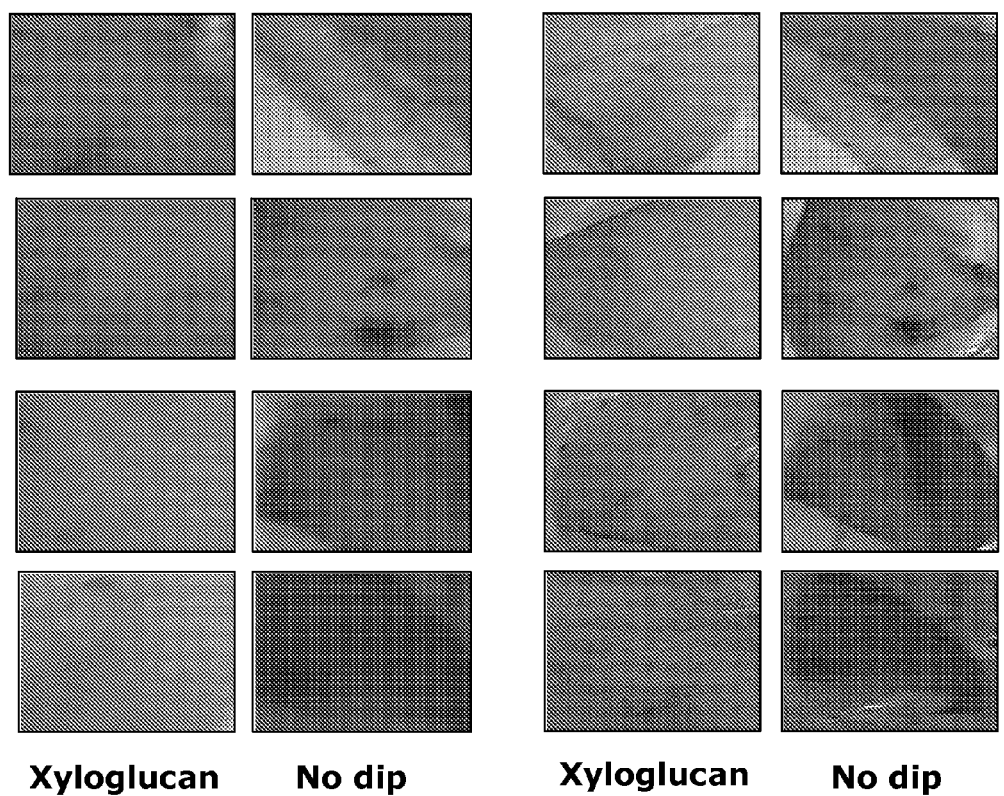
FIG. 7B shows the same slices after 5 days of incubation.

FIG. 7A shows apple slices dipped in xyloglucan in the upper row, or not dipped in the lower row, after 2 days of incubation; FIG. 7B shows the same slices after 5 days of incubation. A clear reduction in the extent to which apple flesh was browned or oxidized was observed in the slices dipped in xyloglucan after 2 days of incubation. By 5 days of incubation, the apple slices not dipped showed indications of mold and substantial oxidation, whereas xyloglucan dipped slices showed only modest oxidation. By comparison, the extent of oxidation was similar between the dipped apple slices at 5 days of incubation and the slices that were not dipped at 2 days of incubation. These images indicate that xyloglucan substantially slowed or prevented the oxidative damage of cut fruit, and prevented the growth of microorganisms that contribute to produce rot.

Example 11: Preservation of Apple Freshness by Xyloglucan and Xyloglucan with *Vigna angularis* Xyloglucan Endotransglycosylase 16

To generate uniformly-sized apple slices without skins, Granny Smith apples were pierced with a size 7 rubber stopper boring tool. The apple inside was removed from the boring tool and then sectioned into 1-2 mm thick discs with a razor blade. Six to eight discs were then dipped into 5 ml of 40 mM sodium citrate pH 5.5 containing either 4.5 mg of xyloglucan per ml with 35 µg of VaXET16 per ml, 4.5 mg of xyloglucan per ml without VaXET16, or 5 ml of deionized water. The excess solution was removed from each apple slice by touching the slice to the side of the container, and the apple discs were transferred to CoStar #3513 12-well, flat bottomed, covered cell culture plates using tweezers. The sample plates were covered and incubated under ambient conditions. Images of the slices were taken after 3, 4, and 7 days by inverting the plates and photographing the slices through the bottom of the plate.

Figure 8A:
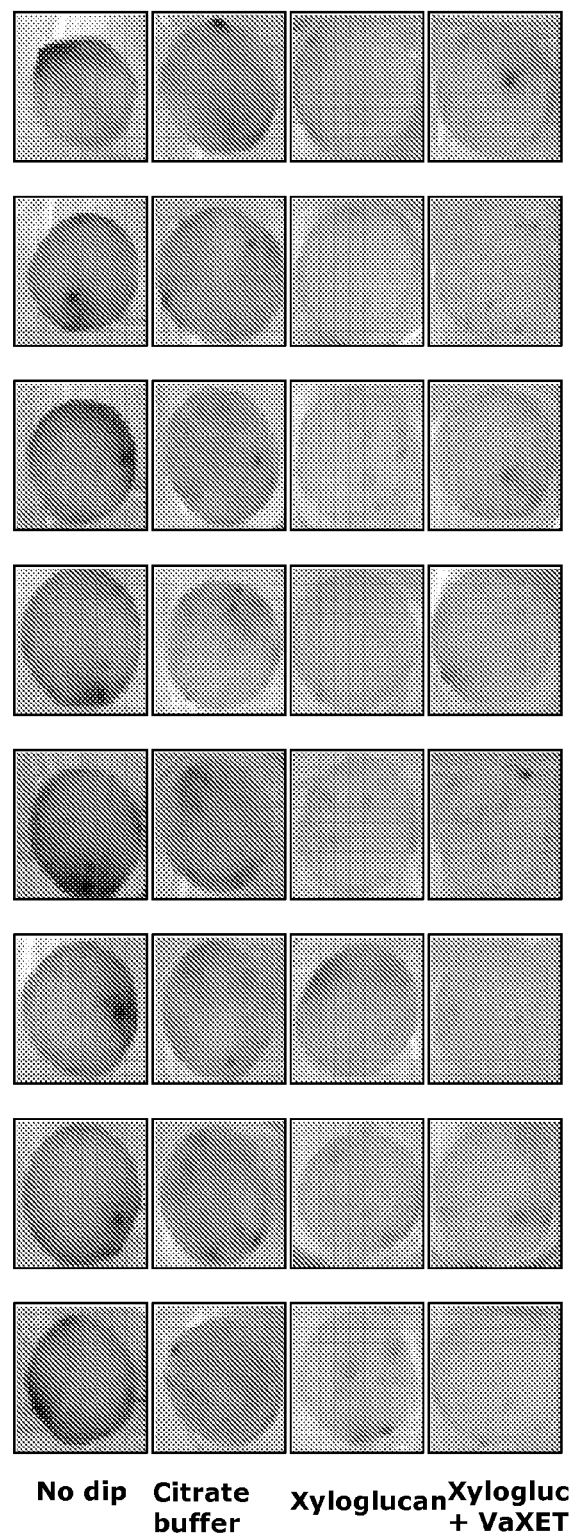
FIG. 8A shows the apple slices after 3 days of incubation.
Figure 8B:
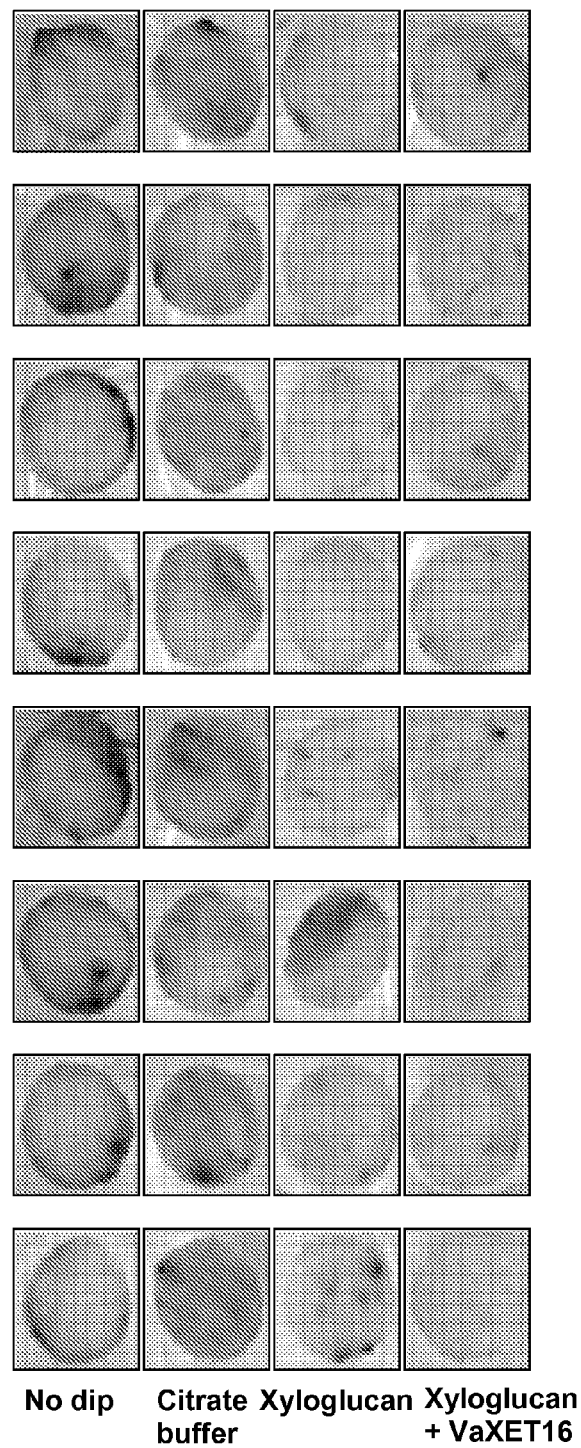
FIG. 8B shows the apple slices after 4 days of incubation.
Figure 8C:
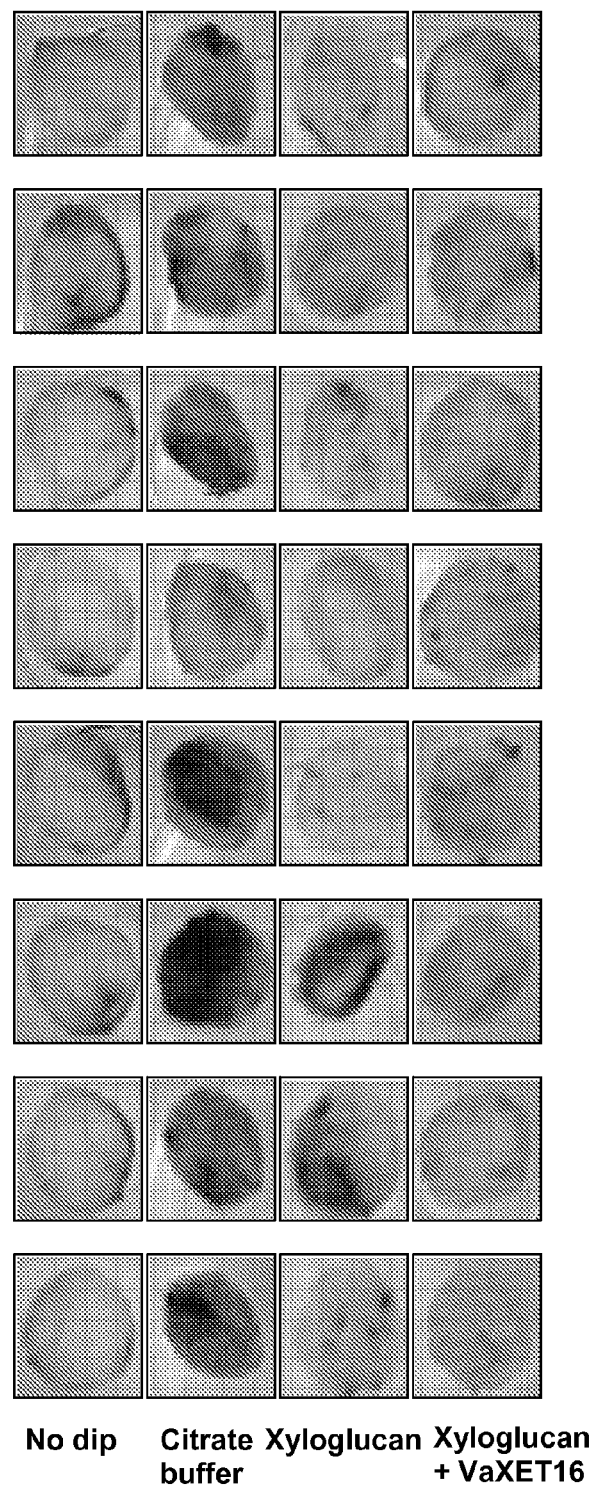
FIG. 8C shows the apple slices after 7 days of incubation.

FIG. 8A shows the apple slices after 3 days of incubation.
FIG. 8B shows the apple slices after 4 days of incubation.
FIG. 8C shows the apple slices after 7 days of incubation.

By 3-4 days of incubation under ambient conditions after the apple slices were prepared, substantial differences were apparent. Apple slices, initially white, had browned and oxidized surfaces in all cases and dark brown spots were evident on all slices to various degrees. The apple slices dipped in a solution of xyloglucan and VaXET16 showed the smallest extent of oxidation or browning of the apple flesh, whereas the sodium citrate buffer dipped and not dipped apple slices were most oxidized. The apples not dipped appeared smaller in diameter than the other samples, indicating that they were more dehydrated than the dipped samples.

By 7 days of incubation, all slices appeared smaller in diameter indicating they had dried out. The dark brown spots covered most of the surface area of the xyloglucan dipped apple slices, the buffer dipped slices appeared to be moldy, and the slices that were not dipped appeared less oxidized than at previous time points but highly desiccated. The xyloglucan and VaXET16 dipped apple slices, by comparison, were oxidized, but less so than the xyloglucan or buffer dipped samples.

These images indicate that over 3 to 4 days, xyloglucan or particularly xyloglucan and VaXET16 reduced the rate of apple oxidation. Over longer time periods, xyloglucan or xyloglucan and VaXET16 delayed spoilage of cut produce.

Example 12: Quantitative Analysis of Apple Slice Images to Determine the Extent to which Xyloglucan and *Vigna angularis* Xyloglucan Endotransglycosylase 16 Prevent Apple Oxidation Photographs of the apple slices shown in FIGS. 9A, 9B, and 9C were quantitatively analyzed using MATLAB® (The Mathworks, Natick, Mass., USA) to differentiate between the extent of oxidation in the apple slices dipped in xyloglucan, xyloglucan with VaXET16, 40 mM sodium citrate pH 5.5, or not dipped. Browning or oxidation of the apple samples was apparent as both a time-dependent browning of the white apple slice overall, and as an increase in the number or size of much darker brown spots. Additionally, in several of the images, particularly day 7 for sodium citrate dipped apples, additional blackening was observed. The extent of browning and its prevention by xyloglucan and VaXET16 were quantified according to the following protocol. Individual color channels of the image files were examined, and the blue channel was determined to have the greatest differences in intensity between both the dark brown spots and the lighter regions of the slices and the samples from the plates. Subsequent analysis was performed using the blue channel only. Photographs were reduced to blue channel intensity values and were inverted by subtraction of the maximum pixel intensity over the image. Regions of interest containing each apple sample were selected, and a threshold filter was applied to remove non-sample pixels from the region of interest. Threshold filters were held constant across all samples in a single plate image, but were varied between images. For each filtered region of interest, histograms of the threshold-subtracted, non-zero pixel intensities were generated and maximum likelihood estimations of best-fit parameters to single and double normal distributions were determined. All non-zero pixel intensities for the 8 apple slices treated in the same way were combined, to generate a global intensity histogram for each treatment. These histograms were similarly fit by maximum likelihood estimation to single and double normal distributions. The extent of browning was then determined in 2 ways. First, as the samples show a tendency to darken or yellow overall, the mean of the single normal distribution was used to determine the average darkness in color of all the sample pixels above the threshold. Second, to quantify the extent to which dark spots cover the surface of the apple slices, the relative areas of dark spots to total surface areas were determined. The probability distribution was integrated over all intensities $>1 \times \sigma$ above the mean of the distribution to determine the relative surface area of the darkest spots.

FIG. 9A shows the pixel intensity histogram of the apple slices not dipped after 4 days of incubation. The histogram is fit to a double normal distribution.

FIG. 9B shows the pixel intensity histogram of the apple slices dipped in 40 mM sodium citrate pH 5.5 after 4 days of incubation. The histogram is fit to a double normal distribution.

FIG. 9C shows the pixel intensity histogram of the apple slices dipped in xyloglucan after 4 days of incubation. The histogram is fit to a double normal distribution.

FIG. 9D shows the pixel intensity histogram of the apple slices dipped in xyloglucan and VaXET16 after 4 days of incubation. The histogram is fit to a double normal distribution.

Figure 9:
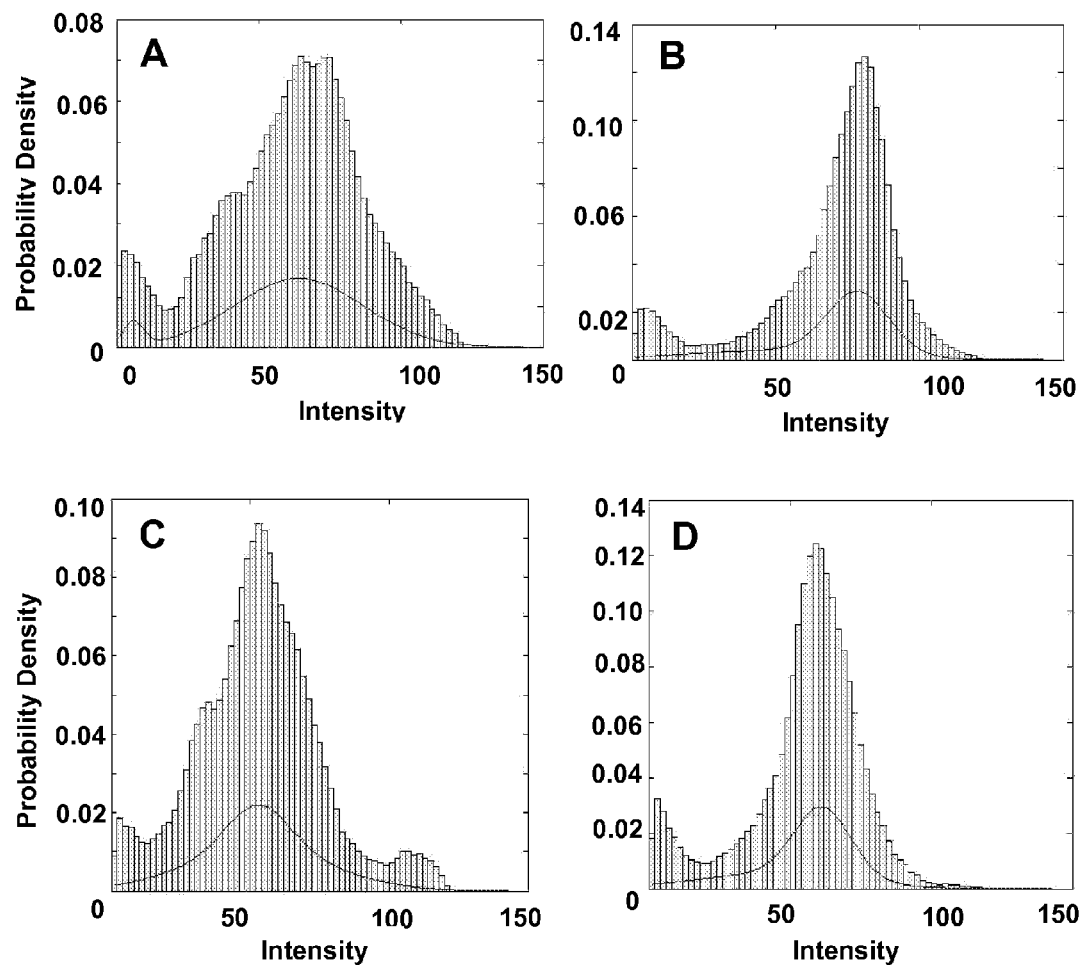
FIG. 9 shows quantitative analysis of apple slice images to determine the extent to which xyloglucan and VaXET16 prevent apple oxidation.

Comparing the histograms in FIG. 9, the samples treated with xyloglucan and VaXET16 had a distribution of intensities that peaked at the lowest intensity, hence were the least yellowed. It was also evident that a substantial fraction of pixels had intensities greater than 100 units in all samples except for those dipped in xyloglucan and VaXET16; for the xyloglucan-dipped and not-dipped apples these appeared as an additional overlapped distribution. By 7 days, this additional distribution was more evident, and was attributed to the onset of very dark spots, which were most apparent in the buffer and xyloglucan-dipped samples (FIG. 9C). This distribution was not present in the xyloglucan and VaXET16-dipped apples, consistent with the lack of dark brown spots on these apple slices.

FIG. 9E shows a plot of the mean of the single Gaussian distribution as a function of time for the variously treated apple slices. Apple slices not dipped are shown as circles, apple slices dipped in 40 mM sodium citrate pH 5.5 are shown as squares, apple slices dipped in xyloglucan are shown as diamonds, and apple slices dipped in xyloglucan and VaXET16 are shown as triangles. With the exception of the slices not dipped, the means increased over time, indicating that the slices became darker in color with time. At the 3 day time point, the means of the sodium citrate dipped and not dipped slices were much higher than were the xyloglucan and xyloglucan with VaXET16 dipped slices. The mean intensities were 68.91±0.0666 for not dipped slices, 69.48±0.0526 for buffer dipped slices, 47.57±0.0436 for the xyloglucan dipped slices, and 50.10±0.0451 for xyloglucan and VaXET16 dipped slices. Thus dipping in either xyloglucan or xyloglucan and VaXET16 reduced the extent of browning by 45% and 38%, respectively.

From the fits of the double normal distributions, apple slices treated in all manners had an intensity distribution mean between 50-65 units and a standard deviation of 20-25. Thus pixel intensities >90 were considered to be outliers or to belong to the high-intensity distribution; they were attributed to the dark brown spots. The total number of pixels exceeding this intensity relative to the total number of pixels exceeding the threshold filter gave the relative proportion of surface area covered by dark brown oxidation spots. This was determined by integration of the intensity distribution over those values of intensity, relative to the integral over all intensities and the values are provided in Table 1.

From the quantification of the dark brown spots, it is clear that xyloglucan and particularly xyloglucan with VaXET16 prevented the formation of dark brown oxidation spots. The relative surface area covered with these spots was approximately 14-fold lower at 3 days, 17-fold lower at 4 days, and 7-fold lower at 7 days between the xyloglucan+VaXET16 dipped apple slices and the average of the buffer-dipped and not-dipped apple slices.

TABLE 1

Relative surface areas of dark brown oxidation spots

|  | Day 3 (%) | Day 4 (%) | Day 7 (%) |
| --- | --- | --- | --- |
| Not dipped | 12.63 | 20.29 | 1.51 |
| Citrate dipped | 14.17 | 17.36 | 28.61 |
| XG dipped | 6.42 | 2.92 | 15.66 |
| XG + XET dipped | 1.77 | 2.03 | 1.87 |

Example 13: Preservation of Potato and Avocado Slices by Xyloglucan and Xyloglucan with *Arabidopsis thaliana* Xyloglucan Endotransglycosylase 14

Preservation of various fruits and vegetables was assessed as described in Example 11 with the following exceptions. *Arabidopsis thaliana* endotransglycosylase 14 (AtXET14) was purified as described in Example 9. Eight replicate samples were dipped into either 20 mM sodium citrate pH 5.5, 1 mg of tamarind seed xyloglucan per ml in 20 mM sodium citrate pH 5.5, or 1 mg of tamarind seed xyloglucan per ml with 1 µM AtXET14 in 20 mM sodium citrate pH 5.5. A size 7 rubber stopper boring tool was used to generate uniformly sized cylinders of the fruit or vegetable examined; potatoes were pierced through the entire thickness of the potato, avocados had their pits removed and were pierced from the pit hole to the skin. Cylinders were removed from the boring tool and potatoes were sectioned into approximately 1 mm thick discs, excluding the outer 1 cm of each cylinder. Avocado slices from equivalent depths within the fruit were generated in the following manner. Three cylinders of equivalent length were positioned together aligned by distance from the pit, and sectioned concurrently into 2 mm thick discs. The resulting 3 slices from each depth were dipped differently and compared with each other to account for potential differences in oxidation, browning, or desiccation that may arise from differences in the fruit. At 0, 2.5, 5, 21 and 70 hours of incubation under ambient conditions, culture plates were photographed to document the degree to which the avocado and potato slices had oxidized.

Figure 10A:
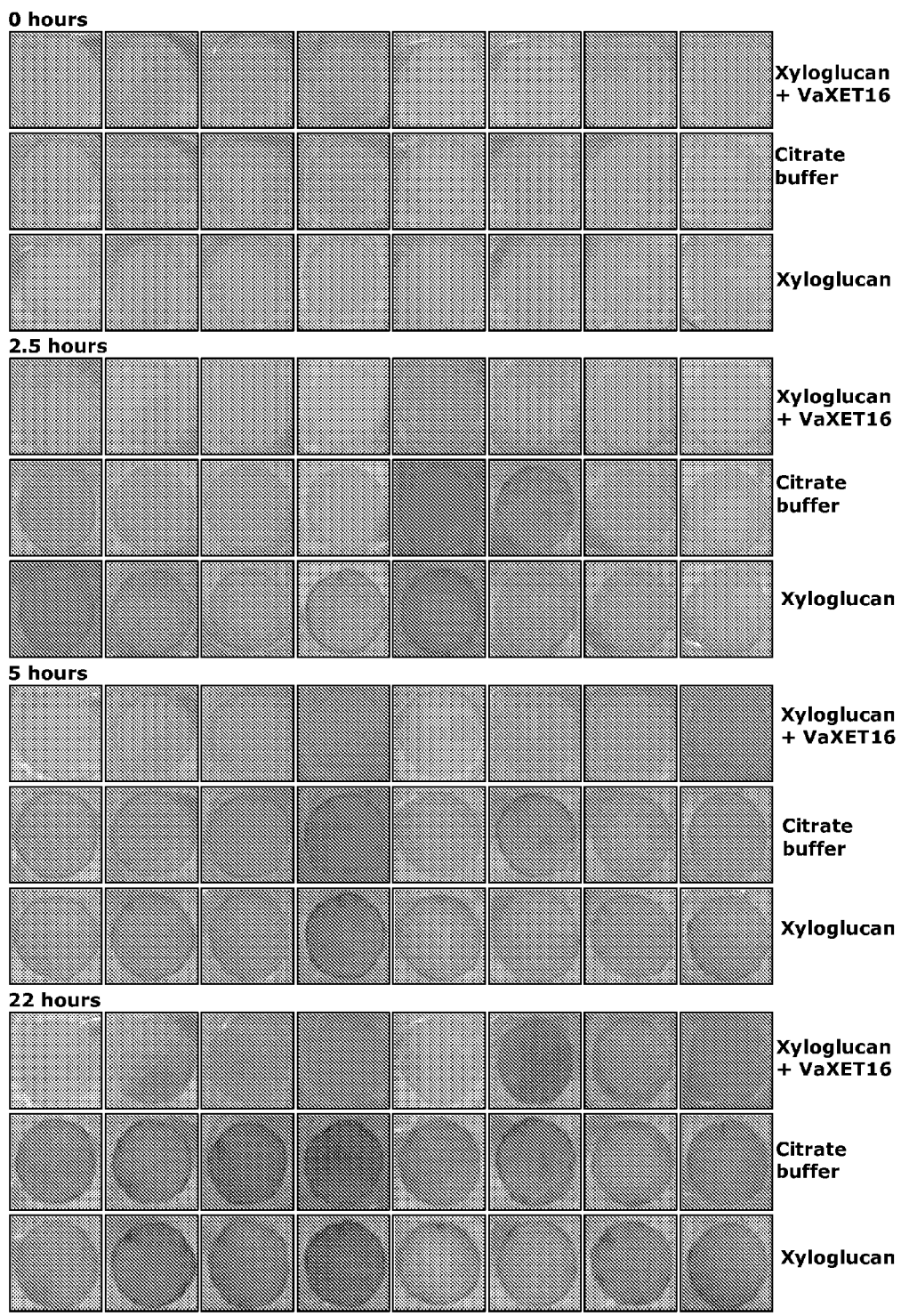
FIG. 10A shows photographs of culture plates containing potato slices dipped in the indicated solutions. Photographs are taken at 0, 2.5, 5, and 22 hours of incubation.

FIG. 10A shows variously treated potato slices after 0, 2.5, 5 and 21 hours of incubation. From the photographs, it is evident that at the beginning of the incubation (time=0 hour), all slices are white. Within the first few hours, potato slices begin to turn brown or oxidize and become increasingly darker in color with time. The slices that were dipped in xyloglucan and AtXET14 show the latest onset of browning, and the smallest extent of browning at the longer incubation times.

Figure 10B:
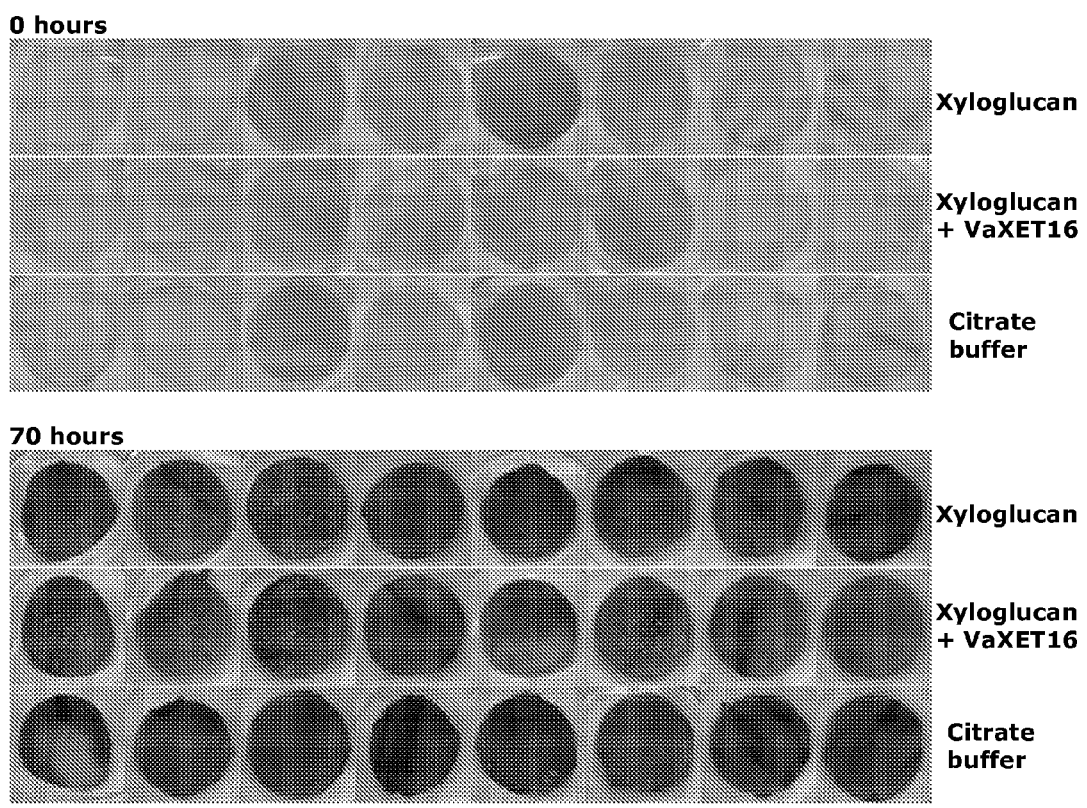
FIG. 10B shows photographs of culture plates containing avocado slices dipped in the indicated solutions. Photographs were taken at 0 and 70 hours of incubation.

FIG. 10B shows variously treated avocado slices after 0 and 70 hours of incubation. The avocado fruit transitions in color from green through yellow at increasing depths from the skin to the pit. Consequently, slices are compared at equivalent depths and hence equivalent initial colors as is evident in the images taken at the beginning of the incubation (time=0). After 70 hours of incubation, the avocado slices have all browned and darkened; those dipped in xyloglucan and particularly xyloglucan with AtXET14 are less browned.

Example 14: Fluorescein Isothiocyanate-Labeled Xyloglucan Confirms Association of Xyloglucan with Cut Fruit and Vegetables To confirm that xyloglucan was associating with cut fruit, 20 µl of FITC-XG or 40 mM sodium citrate pH 5.5 were applied to carnation stem, banana stem, squash stem, or apple slices, prepared as described in Example 6. Samples were incubated at room temperature for 30 minutes and imaged using a hand-held UV lamp. By visual inspection, fluorescence could only be delineated for the squash stem that had FITC-XG applied. The other samples were too reflective, too autofluorescent, or had insufficiently concentrated fluorescent xyloglucan to differentiate FITC-XG fluorescence from background.

Samples were each covered with 500 µl of 40 mM sodium citrate pH 5.5 and 10 µl of 1.5 mg of AtXET14 per ml of 40 mM sodium citrate pH 5.5 were added to each, generating 30 µg per ml final AtXET14 concentration. Samples were incubated overnight at room temperature with shaking. Following overnight incubation, samples were washed 3 times in 2 ml of 150 mM sodium chloride in 20 mM phosphate pH 7.2, over a period of 8 hours. Samples were then incubated overnight in a minimum volume of 150 mM sodium chloride in 20 mM phosphate pH 7.0.

Thin sections of each sample were cut using a razor blade and laid onto a FisherFinest Premium 3"×1"×1 mm microscope slide (Fisher Scientific, Inc., Pittsburgh, Pa., USA). Approximately 20 µl of deionized water were applied to the slide around the sample and the sample was covered with a Fisherbrand 22×22-1.5 microscope coverslip (Fisher Scientific, Inc., Pittsburgh, Pa., USA) before sealing the coverslip to the slide using nail polish.

Laser scanning confocal microscopy was performed using an Olympus FV1000 laser scanning confocal microscope (Olympus, Center Valley, Pa., USA). Data were acquired utilizing the 488 nm line of an argon ion laser excitation source with either a 10× air gap or a 40× oil immersion objective lens. All images were obtained using the same excitation intensity and PMT voltage; hence relative fluorescence intensities were comparable between images.

FIG. 11 shows a series of laser scanning confocal microscope images that compare a fruit, flower, or vegetable incubated with AtXET14 in 150 mM sodium chloride in 20 mM phosphate pH 7.2 to incubation with AtXET14 and FITC-XG in 150 mM sodium chloride in 20 mM phosphate pH 7.2. In each case, FITC-XG and AtXET14 incubated samples showed much higher fluorescence intensity than did the samples incubated with only AtXET14, indicating substantial FITC-XG binding.

FIG. 11A shows a confocal image of a section of an apple slice incubated with AtXET14.

FIG. 11B shows a confocal image of a section of an apple slice incubated with AtXET14 with FITC-XG.

FIG. 11C shows a confocal image of a section of a carnation stem incubated with AtXET14.

FIG. 11D shows a confocal image of a section of a carnation stem incubated with AtXET14 with FITC-XG.

FIG. 11E shows a confocal image of a section of a banana stem incubated with AtXET14.

FIG. 11F shows a confocal image of a section of a banana stem incubated with AtXET14 with FITC-XG.

FIG. 11G shows a confocal image of a section of a squash stem incubated with AtXET14.

FIG. 11H shows a confocal image of a section of a squash stem incubated with AtXET14 and FITC-XG.

In each case the confocal microscopy image indicates that the fluorescein isothiocyanate-labeled xyloglucan associated with the cut fruit, flower or vegetable in the presence of AtXET14.

The present invention is further described by the following numbered paragraphs:

[1] A method for modifying an agricultural crop comprising treating the agricultural crop with a composition selected from the group consisting of (a) a composition comprising a xyloglucan endotransglycosylase, a polymeric xyloglucan, and a functionalized xyloglucan oligomer comprising a chemical group; (b) a composition comprising a xyloglucan endotransglycosylase, a polymeric xyloglucan functionalized with a chemical group, and a functionalized xyloglucan oligomer comprising a chemical group; (c) a composition comprising a xyloglucan endotransglycosylase, a polymeric xyloglucan functionalized with a chemical group, and a xyloglucan oligomer; (d) a composition comprising a xyloglucan endotransglycosylase, a polymeric xyloglucan, and a xyloglucan oligomer; (e) a composition comprising a xyloglucan endotransglycosylase and a polymeric xyloglucan functionalized with a chemical group; (f) a composition comprising a xyloglucan endotransglycosylase and a polymeric xyloglucan; (g) a composition comprising a xyloglucan endotransglycosylase and a functionalized xyloglucan oligomer comprising a chemical group; (h) a composition comprising a xyloglucan endotransglycosylase and a xyloglucan oligomer, and (i) a composition of (a), (b), (c), (d), (e), (f), (g), or (h) without a xyloglucan endotransglycosylase, in a medium under conditions leading to a modified agricultural crop possessing an improved property compared to the unmodified agricultural crop.

[2] The method of paragraph 1, wherein the agricultural crop is harvested.

[3] The method of paragraph 1, wherein the agricultural crop is not harvested.

[4] The method of any of paragraphs 1-3, wherein the agricultural crop is a fruit.

[5] The method of any of paragraphs 1-3, wherein the agricultural crop is a vegetable.

[6] The method of any of paragraphs 1-3, wherein the agricultural crop is a flower.

[7] The method of any of paragraphs 1-3, wherein the agricultural crop is a spice.

[8] The method of any of paragraphs 1-7, wherein the improved property is one or more improvements selected from the group consisting of reducing or preventing oxidative browning, dehydration, desiccation, bacterial, fungal, microbial, animal, or insect pest infestation, senescence, early ripening, and softening; prevention of bruising, resistance to crushing, prevention or enhancement of clustering, aggregation, or association; resistance to adverse environmental factors; appearance, and taste, and resistance to sun or UV damage.

[9] The method of any of paragraphs 1-8, wherein the average molecular weight of the polymeric xyloglucan or the polymeric xyloglucan functionalized with a chemical group ranges from 2 kDa to about 500 kDa.

[10] The method of any of paragraphs 1-9, wherein the average molecular weight of the xyloglucan oligomer or the functionalized xyloglucan oligomer comprising a chemical group ranges from 0.5 kDa to about 500 kDa

[11] The method of any of paragraphs 1-10, wherein the xyloglucan endotransglycosylase is present at a concentration of about 0.1 nM to about 1 mM.

[12] The method of any of paragraphs 1-11, wherein the polymeric xyloglucan or the polymeric xyloglucan functionalized with a chemical group is present at about 1 ng per g of the agricultural crop to about 1 g per g of the agricultural crop.

[13] The method of any of paragraphs 1-12, wherein the xyloglucan oligomer or the functionalized xyloglucan oligomer is present with the polymeric xyloglucan at about 50:1 molar ratio to about 0.5:1 xyloglucan oligomer or functionalized xyloglucan oligomer to polymeric xyloglucan.

[14] The method of any of paragraphs 1-13, wherein the concentration of polymeric xyloglucan, the polymeric xyloglucan functionalized with a chemical group, the xyloglucan oligomer, or the functionalized xyloglucan oligomer comprising a chemical group incorporated into the material is about 0.01 g to about 500 mg per g of the agricultural crop.

[15] The method of any of paragraphs 1-14, wherein the xyloglucan oligomer or the functionalized xyloglucan oligomer is present without polymeric xyloglucan or polymeric xyloglucan functionalized with a chemical group at about 1 ng per g of the material to about 1 g per g of the agricultural crop.

[16] The method of any of paragraphs 1-15, wherein the chemical group is a compound of interest or a reactive group such as an aldehyde group, an amino group, an aromatic group, a carboxyl group, a halogen group, a hydroxyl group, a ketone group, a nitrile group, a nitro group, a sulfhydryl group, or a sulfonate group.

[17] The method of any of paragraphs 1-16, wherein the xyloglucan endotransglycosylase is obtainable from a plant.

[18] The method of paragraph 17, wherein the plant is selected from the group consisting of a dicotyledon and a monocotyledon.

[19] The method of paragraph 18, wherein the dicotyledon is selected from the group consisting of azuki beans, cauliflowers, cotton, poplar or hybrid aspen, potatoes, rapes, soy beans, sunflowers, thalecress, tobacco, and tomatoes.

[20] The method of paragraph 18, wherein the monocotyledon is selected from the group consisting of wheat, rice, corn and sugar cane.

[21] The method of any of paragraphs 1-20, wherein the xyloglucan endotransglycosylase is produced by aerobic cultivation of a transformed host organism containing the appropriate genetic information from a plant.

[22] A modified agricultural crop obtained by the method of any of paragraphs 1-21.

[23] A modified agricultural crop comprising (a) a polymeric xyloglucan, and a functionalized xyloglucan oligomer comprising a chemical group; (b) a polymeric xyloglucan functionalized with a chemical group and a functionalized xyloglucan oligomer comprising a chemical group; (c) a polymeric xyloglucan functionalized with a chemical group, and a xyloglucan oligomer; (d) a polymeric xyloglucan, and a xyloglucan oligomer; (e) a polymeric xyloglucan functionalized with a chemical group; (f) a polymeric xyloglucan; (g) a functionalized xyloglucan oligomer comprising a chemical group; or (h) a xyloglucan oligomer, wherein the modified agricultural crop possesses an improved property compared to the unmodified agricultural crop.

[24] A composition selected from the group consisting of (a) a composition comprising a xyloglucan endotransglycosylase, a polymeric xyloglucan, and a functionalized xyloglucan oligomer comprising a chemical group; (b) a composition comprising a xyloglucan endotransglycosylase, a polymeric xyloglucan functionalized with a chemical group, and a functionalized xyloglucan oligomer comprising a chemical group; (c) a composition comprising a xyloglucan endotransglycosylase, a polymeric xyloglucan functionalized with a chemical group, and a xyloglucan oligomer; (d) a composition comprising a xyloglucan endotransglycosylase, a polymeric xyloglucan, and a xyloglucan oligomer; (e) a composition comprising a xyloglucan endotransglycosylase and a polymeric xyloglucan functionalized with a chemical group; (f) a composition comprising a xyloglucan endotransglycosylase and a polymeric xyloglucan; (g) a composition comprising a xyloglucan endotransglycosylase and a functionalized xyloglucan oligomer comprising a chemical group; (h) a composition comprising a xyloglucan endotransglycosylase and a xyloglucan oligomer, and (i) a composition of (a), (b), (c), (d), (e), (f), (g), or (h) without a xyloglucan endotransglycosylase.

The inventions described and claimed herein are not to be limited in scope by the specific aspects herein disclosed, since these aspects are intended as illustrations of several aspects of the invention. Any equivalent aspects are intended to be within the scope of the inventions. Indeed, various modifications of the inventions in addition to those shown and described herein will become apparent to those skilled in the art from the foregoing description. Such modifications are also intended to fall within the scope of the appended claims. In the case of conflict, the present disclosure including definitions will control.

What is claimed is:

1. A method for modifying an agricultural crop comprising treating the agricultural crop with a composition selected from the group consisting of (a) a composition comprising a xyloglucan endotransglycosylase, a polymeric xyloglucan, and a functionalized xyloglucan oligomer comprising a chemical group; (b) a composition comprising a xyloglucan endotransglycosylase, a polymeric xyloglucan functionalized with a chemical group, and a functionalized xyloglucan oligomer comprising a chemical group; (c) a composition comprising a xyloglucan endotransglycosylase, a polymeric xyloglucan functionalized with a chemical group, and a xyloglucan oligomer; (d) a composition comprising a xyloglucan endotransglycosylase, a polymeric xyloglucan, and a xyloglucan oligomer; (e) a composition comprising a xyloglucan endotransglycosylase and a polymeric xyloglucan functionalized with a chemical group; (f) a composition comprising a xyloglucan endotransglycosylase and a polymeric xyloglucan; (g) a composition comprising a xyloglucan endotransglycosylase and a functionalized xyloglucan oligomer comprising a chemical group; and (h) a composition comprising a xyloglucan endotransglycosylase and a xyloglucan oligomer, wherein the treating of the agricultural crop with the composition is in a medium under conditions leading to a modified agricultural crop possessing an improved property compared to the unmodified agricultural crop, wherein the agricultural crop is a fruit, a vegetable, a grain, a flower, or a spice.

2. The method of claim 1, wherein the treating of the agricultural crop is after harvest.

3. The method of claim 1, wherein the treating of the agricultural crop is before harvest.

4. The method of claim 1, wherein the improved property is one or more improvements selected from the group consisting of reducing or preventing oxidative browning, dehydration, desiccation, bacterial, fungal, microbial, animal, or insect pest infestation, senescence, early ripening, and softening; prevention of bruising, resistance to crushing, prevention or enhancement of clustering, aggregation, or association; resistance to adverse environmental factors; appearance, and taste, and resistance to sun or UV damage.

5. The method of claim 1, wherein the average molecular weight of the polymeric xyloglucan or the polymeric xyloglucan functionalized with a chemical group ranges from 2 kDa to about 500 kDa.

6. The method of claim 1, wherein the average molecular weight of the xyloglucan oligomer or the functionalized xyloglucan oligomer comprising a chemical group ranges from 0.5 kDa to about 500 kDa.

7. The method of claim 1, wherein the xyloglucan endotransglycosylase is present at a concentration of about 0.1 nM to about 1 mM.

8. The method of claim 1, wherein the polymeric xyloglucan or the polymeric xyloglucan functionalized with a chemical group is present at about 1 ng per g of the agricultural crop to about 1 g per g of the agricultural crop.

9. The method of claim 1, wherein the xyloglucan oligomer or the functionalized xyloglucan oligomer is present with the polymeric xyloglucan at about 50:1 molar ratio to about 0.5:1 xyloglucan oligomer or functionalized xyloglucan oligomer to polymeric xyloglucan.

10. The method of claim 1, wherein the concentration of polymeric xyloglucan, the polymeric xyloglucan functionalized with a chemical group, the xyloglucan oligomer, or the functionalized xyloglucan oligomer comprising a chemical group is about 0.01 g to about 500 mg per g of the agricultural crop.

11. The method of claim 1, wherein the xyloglucan oligomer or the functionalized xyloglucan oligomer is present without polymeric xyloglucan or polymeric xyloglucan functionalized with a chemical group at about 1 ng per g to about 1 g per g of the agricultural crop.

12. The method of claim 1, wherein the chemical group is a compound of interest or a reactive group.

13. The method of claim 12, wherein the reactive group is selected from the group consisting of an aldehyde group, an amino group, an aromatic group, a carboxyl group, a halogen group, a hydroxyl group, a ketone group, a nitrile group, a nitro group, a sulfhydryl group, and a sulfonate group.

* * * * *